United States Patent
Fader et al.

(10) Patent No.: US 9,284,310 B2
(45) Date of Patent: Mar. 15, 2016

(54) INHIBITORS OF CYTOMEGALOVIRUS

(71) Applicant: Boehringer Ingelheim International GmbH, Ingelheim am Rhein (DE)

(72) Inventors: Lee Fader, New Milford, CT (US); Francois Bilodeau, Laval (CA); Mathieu Parisien, Laval (CA); Maude Poirier, Pennington, NJ (US); Cyrille Kuhn, Danbury, CT (US); Carl Thibeault, Mascouche (CA); Thao Trinh, St-Colomban (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/440,086

(22) PCT Filed: Oct. 31, 2013

(86) PCT No.: PCT/US2013/067673
§ 371 (c)(1),
(2) Date: May 1, 2015

(87) PCT Pub. No.: WO2014/070978
PCT Pub. Date: May 8, 2014

(65) Prior Publication Data
US 2015/0315180 A1    Nov. 5, 2015

Related U.S. Application Data

(60) Provisional application No. 61/722,151, filed on Nov. 3, 2012.

(51) Int. Cl.
| C07D 417/14 | (2006.01) |
| C07D 417/12 | (2006.01) |
| C07D 413/12 | (2006.01) |

(52) U.S. Cl.
CPC ............ *C07D 417/14* (2013.01); *C07D 413/12* (2013.01); *C07D 417/12* (2013.01)

(58) Field of Classification Search
None
See application file for complete search history.

(56) References Cited

U.S. PATENT DOCUMENTS 6,166,028 A    12/2000    Bloom et al.

FOREIGN PATENT DOCUMENTS

| SE | WO2004/052880 | * | 6/2004 |
| WO | 0034238 | | 6/2000 |
| WO | 0034258 A2 | | 6/2000 |
| WO | 0034261 A2 | | 6/2000 |
| WO | 02085869 A1 | | 10/2002 |
| WO | 2004041789 A1 | | 5/2004 |
| WO | 2004071426 A2 | | 8/2004 |
| WO | 2006010637 A2 | | 2/2006 |
| WO | 2007005668 A2 | | 1/2007 |
| WO | 2009011850 A2 | | 1/2009 |
| WO | 2010029300 | | 3/2010 |
| WO | 2010043377 A1 | | 4/2010 |
| WO | 2010077582 A1 | | 7/2010 |
| WO | 2012004217 A1 | | 1/2012 |

OTHER PUBLICATIONS

International Search report and Written Opinion PCT ISA 220 mailed Dec. 18, 2014 for PCT 2013067673.

* cited by examiner

*Primary Examiner* — Timothy R Rozof
(74) *Attorney, Agent, or Firm* — Michael P. Morris; Edward S. Lazer

(57) ABSTRACT

Compounds of Formula (I) wherein n, $R^1$, $R^{1-4}$, $R^2$, $R^3$, Y and Z are defined herein, are useful for the treatment of cytomegalovirus disease and/or infection.

17 Claims, No Drawings

INHIBITORS OF CYTOMEGALOVIRUS

SEQUENCE LISTING

The instant application contains a Sequence Listing which has been submitted electronically in ASCII format and is hereby incorporated by reference in its entirety. Said ASCII copy, created on Oct. 15, 2013, is named 13-0181_SL.txt and is 1,701 bytes in size.

FIELD OF THE INVENTION

The present invention relates to N-biaryl amide analogs and their use as inhibitors of cytomegalovirus (CMV) replication, pharmaceutical compositions containing such analogs, and methods of using these analogs in the treatment and prevention of CMV disease and/or infection.

BACKGROUND OF THE INVENTION

CMV, a β-herpes virus, is a frequent and ubiquitous virus that affects all populations, worldwide, including adults and children with normal or compromised immune systems. CMV replication in the immunosuppressed host, if left unchecked, results in severe morbidity, mortality and other complications such as predisposition to bacterial and fungal infections, graft versus host disease and potential graft failure. CMV infection is the most common infection in patients undergoing hematopoietic stem cell transplantation (HCT) or solid organ transplantation (SOT). CMV is prevalent in 50-80% adult transplant candidates and found at lower prevalence in children. The current Gold Standard (Valganciclovir, Ganciclovir) is myelotoxic, and interferes with bone marrow engraftment in HCT. Therefore, its use in this population is limited to pre-emptive therapy, and the duration of its administration and the size of dose are often limited by its toxicity. This toxicity also limits the duration of prophylactic use and the dose in SOT. As a result, a new agent without the toxicities of Valganciclovir, Ganciclovir that allows for more effective prevention of CMV disease and transplant engraftment, and that substantially reduces treatment-related complications would represent a major break-through.

SUMMARY OF THE INVENTION

The present invention provides a novel series of compounds having inhibitory activity against CMV replication.

Further objects of this invention arise for the one skilled in the art from the following description and the examples.

An embodiment of the invention provides a compound of Formula (I) or racemate, enantiomer, diastereomer or tautomer thereof:

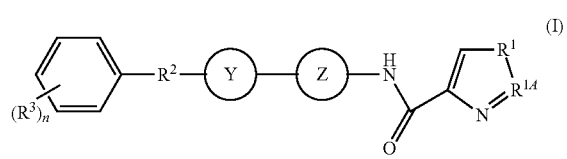

(I)

wherein
$R^1$ is S or O;
$R^{1A}$ is CH or N;
Ring Z is selected from the group consisting of phenyl, pyridine and pyridinone, wherein said phenyl, pyridine and pyridinone are each optionally mono-, di- or tri-substituted with $(C_{1-6})$alkyl or —O—$(C_{1-6})$alkyl;

Ring Y is selected from the group consisting of imidazole, triazole and pyridine, wherein said imidazole, triazole and pyridine are each optionally mono-, di- or tri-substituted with halo, —CN, OH, —O—$(C_{1-6})$alkyl, —C(=O)NH$_2$, $(C_{1-6})$haloalkyl, $(C_{2-6})$alkenyl, $(C_{2-6})$alkynyl or $(C_{1-6})$alkyl optionally mono- or di-substituted with OH, —C(=O)NH$_2$, —C(=O)OH, $Y^1$, —O—$(C_{1-6})$alkyl-$Y^1$ or —N(H)—$(C_{1-6})$alkyl)-$Y^1$;

$Y^1$ is aryl, heterocycle or heteroaryl, wherein said aryl, heterocycle or heteroaryl are each optionally mono-, di- or tri-substituted with halo, —CN, OH, —O—$(C_{1-6})$alkyl, $(C_{1-6})$haloalkyl or $(C_{1-6})$alkyl;

$R^2$ is absent, $(C_{1-6})$alkyl, $(C_{3-7})$cycloalkyl, —O, —N($R^{2A}$), *—N($R^{2A}$)—C(=O)—§, *—N($R^{2A}$)—C(=O)—$(C_{3-7})$cycloalkyl-§, *—N($R^{2A}$)—C(=O)—$(C_{1-6})$alkyl-§ (wherein, when necessary, the site of attachment to the Y ring is indicated with an * and the site of attachment to the phenyl ring is indicated with a §);

wherein each said alkyl is optionally mono-, di- or tri-substituted with substituents independently selected from the group consisting of OH, —O—$(C_{1-6})$alkyl, —O-aryl and —O—$(C_{1-6})$alkyl-aryl;

$R^{2A}$ is H or $(C_{1-6})$alkyl;

$R^3$ is halo, $(C_{1-6})$haloalkyl, —CN, OH, —O—$(C_{1-6})$alkyl or $(C_{1-6})$alkyl, wherein each said alkyl is optionally mono- or di-substituted with OH, C(=O)OH, aryl, heterocycle or heteroaryl;

n is 0, 1, 2 or 3;

or a salt thereof.

Another embodiment of the invention provides a compound having the formula:

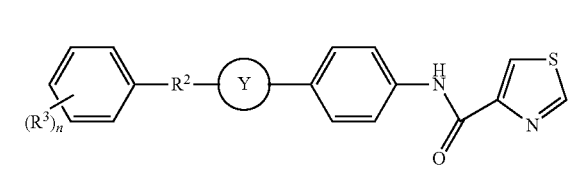

wherein Ring Y, $R^2$, $R^3$ and n are as defined above, or a pharmaceutically acceptable salt thereof.

Another embodiment of the invention provides a compound having the formula:

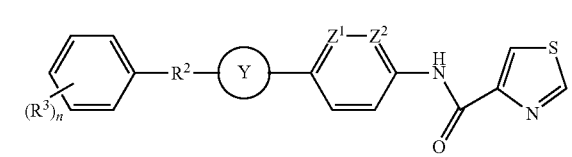

wherein Ring Y, $R^2$, $R^3$ and n are as defined above, and one of $Z^1$ and $Z^2$ is CH and the other of $Z^1$ and $Z^2$ is N; or a pharmaceutically acceptable salt thereof.

Another embodiment of the invention provides a compound having the formula:

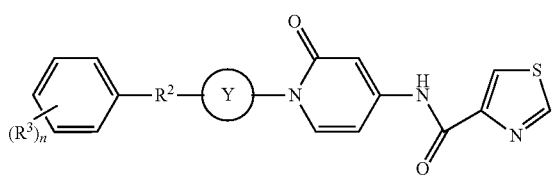

wherein Ring Y, R², R³ and n are as defined above, or a pharmaceutically acceptable salt thereof.

Another embodiment of this invention provides a compound of the invention, or a pharmaceutically acceptable salt thereof, as a medicament.

Also within the scope of this invention is the use of a compound of the invention, or a pharmaceutically acceptable salt thereof, for the manufacture of a medicament for the treatment or prevention of CMV disease and/or infection in a human being.

Included within the scope of this invention is a pharmaceutical composition comprising a compound of the invention, or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a CMV infection in a human being having or at risk of having the infection.

The invention also provides the use of a pharmaceutical composition as described hereinabove for the treatment of CMV disease in a human being having or at risk of having the disease.

Another aspect of the invention involves a method of treating or preventing CMV disease and/or infection in a human being by administering to the human being an anti-CMV virally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat CMV disease and/or infection; and packaging material comprising a label which indicates that the composition can be used to treat disease and/or infection by CMV; wherein the composition comprises a compound of the invention according to this invention or a pharmaceutically acceptable salt thereof.

Still another aspect of this invention relates to a method of inhibiting the replication of CMV comprising exposing the virus to an effective amount of the compound of the invention, or a salt thereof, under conditions where replication of CMV is inhibited.

Further included in the scope of the invention is the use of a compound of the invention, or a salt thereof, to inhibit the replication of CMV.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, with the $C_{1-3}$-alkyl group bound to the core. Unless specifically stated otherwise, for groups comprising two or more subgroups, the substituent may be attached to either subgroup.

In case a compound of the present invention is depicted in the form of a chemical name and as a formula in case of any discrepancy the formula shall prevail. An asterisk or the designation, - - - -, may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-3}$-alkyl embraces the radicals $H_3C$—, $H_3C$—$CH_2$—, $H_3C$—$CH_2$—$CH_2$— and $H_3C$—$CH(CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "carbocyclyl" or "carbocycle" as used herein, either alone or in combination with another radical, means a mono-, bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms. Thus, the term "heterocyclyl" or "heterocyclyl" includes the following exemplary structures which are not depicted as radicals as each form may be attached through a covalent bond to any atom so long as appropriate valences are maintained:

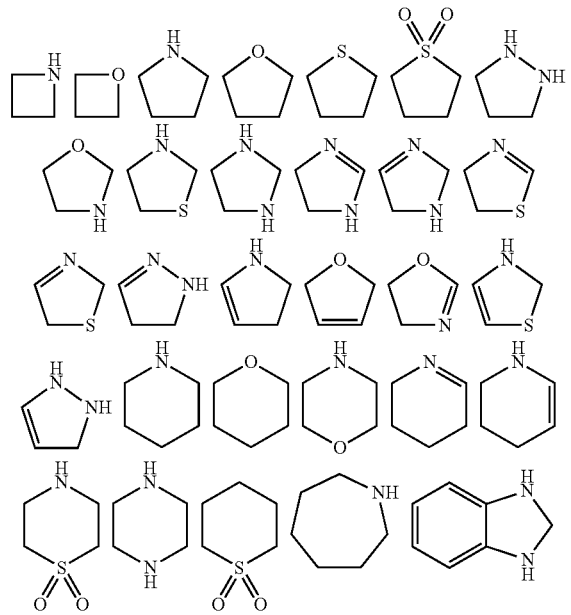

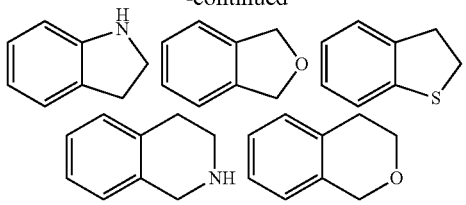

The term "heteroaryl" means a mono- or polycyclic-ring system containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms. Thus, the term "heteroaryl" includes the following exemplary structures which are not depicted as radicals as each form may be attached through a covalent bond to any atom so long as appropriate valences are maintained:

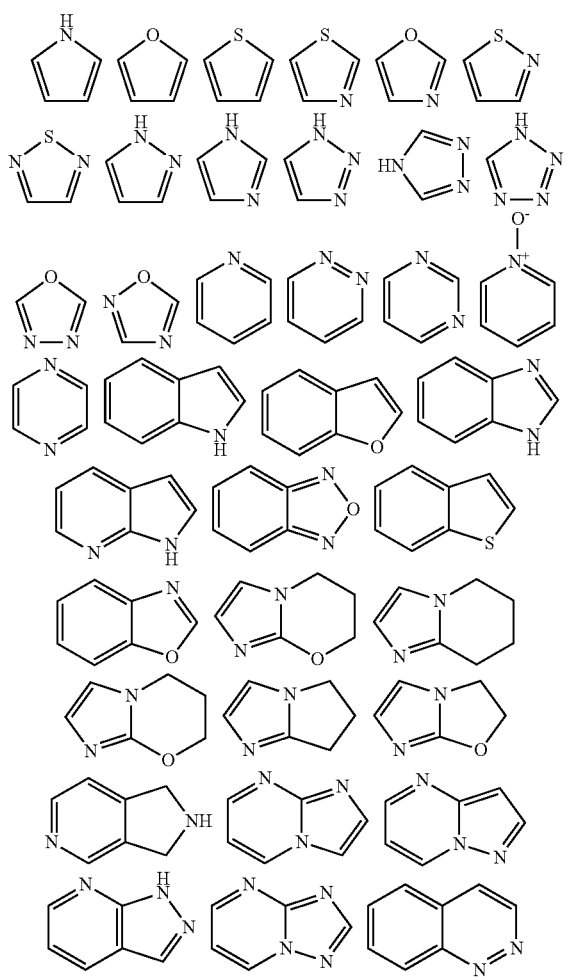

Many of the terms given above may be used repeatedly in the definition of a formula or group and in each case have one of the meanings given above, independently of one another.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

As used herein, the term "treatment" means the administration of a compound or composition according to the present invention to alleviate or eliminate symptoms of CMV disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Further Embodiments

In the following preferred embodiments, groups and substituents of the compounds of Formula (I) according to this invention are described in detail.

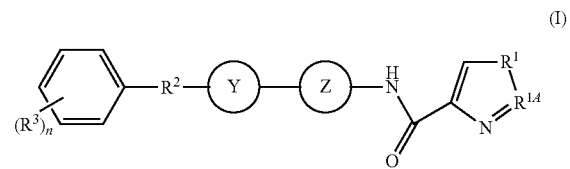

(I)

Any and each of the definitions below may be combined with each other.

$R^1$:
$R^1$-A: $R^1$ is O or S.
$R^1$-B: $R^1$ is O.
$R^1$-C: $R^1$ is S.
$R^{1A}$:
$R^{1A}$-A: $R^{1A}$ is CH or N.
$R^{1A}$-B: $R^{1A}$ is N.
$R^{1A}$-C: $R^{1A}$ is CH.

Ring Z:
Ring Z-A: Ring Z is selected from the group consisting of phenyl, pyridine and pyridinone, wherein each said phenyl, pyridine and pyridinone are optionally mono-, di- or tri-substituted with $(C_{1-6})$alkyl or —O—$(C_{1-6})$alkyl.
Ring Z-B: Ring Z is selected from the group consisting of phenyl, pyridine and pyridinone.
Ring Z-C: Ring Z is phenyl.
Ring Z-D: Ring Z is pyridine.
Ring Z-E: Ring Z is pyridinone.

Ring Y:
Ring Y-A: Ring Y is selected from the group consisting of imidazole, triazole and pyridine, wherein said imidazole, triazole and pyridine are each optionally mono-, di- or tri-substituted with halo, —CN, OH, —O—$(C_{1-6})$alkyl, —C(=O)NH$_2$, $(C_{1-6})$haloalkyl, $(C_{2-6})$alkenyl, $(C_{2-6})$alkynyl or $(C_{1-6})$alkyl optionally mono- or di-substituted with OH, —C(=O)NH$_2$, —C(=O)OH, $Y^1$, —O—$(C_{1-6})$alkyl-$Y^1$ or —N(H)—$(C_{1-6})$alkyl)-$Y^1$;

$Y^1$ is aryl, heterocycle or heteroaryl, wherein said aryl, heterocycle or heteroaryl are each optionally mono-, di- or tri-substituted with halo, —CN, OH, —O—$(C_{1-6})$alkyl, $(C_{1-6})$haloalkyl or $(C_{1-6})$alkyl.

Ring Y-B: Ring Y is selected from the group consisting of imidazole, triazole and pyridine.
Ring Y-C: Ring Y is imidazole.
Ring Y-D: Ring Y is triazole.
Ring Y-E: Ring Y is pyridine.

$R^2$:
$R^2$-A: $R^2$ is absent, $(C_{1-6})$alkyl, $(C_{3-7})$cycloalkyl, —O, —N($R^{2A}$), *—N($R^{2A}$)—C(=O)—§, *—N($R^{2A}$)—C(=O)—$(C_{3-7})$cycloalkyl-§, *—N($R^{2A}$)—C(=O)—$(C_{1-6})$alkyl-§ (wherein, when necessary, the site of attachment to the Y ring is indicated with an * and the site of attachment to the phenyl ring is indicated with a §);

wherein each said alkyl is optionally mono-, di- or tri-substituted with substituents independently selected from the group consisting of OH, —O—($C_{1-6}$)alkyl, —O-aryl and —O—($C_{1-6}$)alkyl-aryl;

$R^{2,4}$ is H or ($C_{1-6}$)alkyl.

$R^2$-B: $R^2$ is absent or ($C_{1-6}$)alkyl, optionally mono-, di- or tri-substituted with substituents independently selected from the group consisting of OH, —O—($C_{1-6}$)alkyl, —O-aryl and —O—($C_{1-6}$)alkyl-aryl.

$R^2$-C: $R^2$ is absent.

$R^3$:

$R^3$-A: $R^3$ is halo, ($C_{1-6}$)haloalkyl, —CN, OH, —O—($C_{1-6}$)alkyl or ($C_{1-6}$)alkyl,
wherein each said alkyl is optionally mono- or di-substituted with OH, C(=O)OH, aryl, heterocycle or heteroaryl.

$R^3$-B: $R^3$ is halo, ($C_{1-6}$)haloalkyl, —CN or ($C_{1-6}$)alkyl.

$R^3$-C: $R^3$ is halo or ($C_{1-6}$)haloalkyl.

n:

n-A: n is 0, 1, 2 or 3.

n-B: n is 0, 1 or 2.

n-C: n is 1 or 2.

Further subgeneric embodiments of the present invention are set forth in the following table, wherein each substituent group of each embodiment is defined according to the definitions set forth above:

| Embodiment | $R^1$ | $R^{1,4}$ | $R^2$ | $R^3$ | Y | Z | n |
|---|---|---|---|---|---|---|---|
| E-1 | $R^1$-C | $R^{1,4}$-C | $R^2$-C | $R^4$-C | Y-B | Z-B | n-C |
| E-2 | $R^1$-C | $R^{1,4}$-C | $R^2$-C | $R^4$-B | Y-B | Z-B | n-B |
| E-3 | $R^1$-C | $R^{1,4}$-C | $R^2$-B | $R^4$-C | Y-D | Z-B | n-C |
| E-4 | $R^1$-B | $R^{1,4}$-C | $R^2$-B | $R^4$-B | Y-C | Z-C | n-B |
| E-5 | $R^1$-A | $R^{1,4}$-B | $R^2$-C | $R^4$-B | Y-A | Z-D | n-B |
| E-6 | $R^1$-A | $R^{1,4}$-A | $R^2$-B | $R^4$-B | Y-A | Z-E | n-A |

Examples of most preferred compounds according to this invention are each single compound in Table 1.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

Suitable injectables may be obtained, for example, by mixing one or more compounds according to the invention with known excipients, for example inert diluents, carriers, co-solvent, adjuvants, surfactants and/or cyclodextrin complex. The injectable formulation may be an emulsion or suspension.

Combination Therapy

Combination therapy is contemplated wherein a compound of the invention, or a pharmaceutically acceptable salt thereof, is co-administered with at least one additional agent selected from: a CMV entry inhibitor, a CMV early transcription event inhibitor, a CMV helicase-primase inhibitor, a CMV DNA polymerase inhibitor, an inhibitor of UL97 kinase, a CMV protease inhibitor, a CMV terminase inhibitor, a CMV maturation inhibitor, an inhibitor of another target in the CMV life cycle, a CMV vaccine and a CMV biological agent.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

Antiviral agents contemplated for use in such combination therapy include agents (compounds or biologicals) that are effective to inhibit the production and/or replication of a virus in a human being, including but not limited to agents that interfere with either host or viral mechanisms necessary for the production and/or replication of a virus in a human being. Such agents can be selected from: a CMV entry inhibitor; a CMV early transcription event inhibitor; a CMV helicase-primase inhibitor; a CMV DNA polymerase inhibitor such as Ganciclovir (Cytovene), Valganciclovir (Valcyte; Cymeval), Cidofovir (Vistide), Foscarnet (Foscavir), CMX001, cyclopropavir (MBX-400) and Valaciclovir (Valtrex; Zelitrex); an inhibitor of UL97 kinase such as Maribavir; a CMV protease inhibitor; a CMV terminase inhibitor such as AIC246 (Letermovir); a CMV maturation inhibitor; other inhibitors such as Artesunate; a CMV vaccine such as TransVax and a CMV biological agent such as Cytogam (Cytotect), TCN-202 and CMV IgG.

EXAMPLES

Other features of the present invention will become apparent from the following non-limiting examples which illustrate the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. The reactants used in the examples below may be obtained either as described herein, or if not described herein, are themselves either commercially available or may be prepared from commercially available materials by methods known in the art. Mass spectral analyses may be recorded using an electrospray mass spectrometer.

Compounds and intermediates can be purified by a Teledyne ISCO Combiflash $R_f$ System at 254 nm using commercial normal phase silica 4-120 g Redisep $R_f$ or Silicycle columns at a flow rate of 18-85 mL/min depending on column size. Mass spectral analyses may be recorded using flow injection analysis mass spectrometry or Waters Acquity Ultraperformance LC System consisting of a sample organizer, PDA detector, column manager, sample manager, binary solvent manager and SQ detector.

Reactions performed in microwave conditions are conducted in a Biotage Initiator 2.0 microwave synthesizer equipped with a Robot Sixty for vial manipulations. The temperature range is from 40-250° C. The pressure range is from 0-20 bar and the power range is from 0-400 Watts at 2.45 GHz. The vial size varies from 0.5 mL to 20 mL. The solvent absorption level is high by default. Specific reaction times and temperatures are given in the experimental section when applicable.

Preparative RP-HPLC is performed under standard conditions using one of the following specific measuring conditions:

A) Waters SunFire Prep OBD C18 column (5 μm, 19×50 mm) eluting firstly with a hold period of 1 min in initial gradient condition then eluting with a linear MeOH gradient containing 10 mM Ammonium Formate (pH 3.8) over 10 min at 30 mL/min. Fractions containing the desired product are pooled, concentrated and lyophilized.

B) Waters XBridge Prep OBD C18 column (5 μm, 19×50 mm) eluting firstly with a hold period of 1 min in initial gradient condition then eluting with a linear MeOH gradient containing 10 mM Ammonium Bicarbonate (pH 10.0) over 10 min at 30 mL/min. Fractions containing the desired product are pooled, concentrated and lyophilized.

C) Waters SunFire Prep OBD C18 column (5 μm, 19×50 mm) eluting firstly with a hold period of 1 min in initial gradient condition then eluting with a linear MeCN gradient containing 0.06% TFA (v/v) over 10 min at 30 mL/min. Fractions containing the desired product are pooled and lyophilized.

D) Waters XBridge Prep OBD C18 column (5 μm, 19×50 mm) eluting firstly with a hold period of 1 min in initial gradient condition then eluting with a linear MeCN gradient containing 10 mM Ammonium Bicarbonate (pH 10.0) over 10 min at 30 mL/min. Fractions containing the desired product are pooled and lyophilized.

E) Waters Sun Fire Prep OBD C18 column (5 μm, 19×50 mm) eluting firstly with a hold period of 0.5 min in initial gradient condition then eluting with a linear MeCN gradient containing 10 mM Ammonium Formate (pH 3.8) over 6.9 min at 45 mL/min. The eluents are warmed at 45° C. using a Timberline Instrument TL600 Mobile Phase Heater during the whole run. Fractions containing the desired product are pooled and lyophilized.

F) Waters XSelect Prep CSH OBD C18 column (5 μm, 30×75 mm) eluting firstly with a hold period of 0.5 min in initial gradient condition then eluting with a linear MeCN gradient containing 0.1% formic acid (v/v) over 6.4 min at 60 mL/min. The eluents are warmed at 45° C. using a Timberline Instrument TL600 Mobile Phase Heater during the whole run. Fractions containing the desired product are pooled and lyophilized.

Analytical UPLC is performed under standard conditions using one of the following specific measuring conditions:

A) Waters ACQUITY UPLC BEH C18 column (1.7 μm, 2.1×30 mm) eluting with a linear MeOH gradient containing 10 mM Ammonium Bicarbonate (pH 10) over 2.2 min at 0.75 mL/min.

B) Waters ACQUITY UPLC HSS C18 column (1.8 μm, 2.1×30 mm) eluting with a linear MeOH gradient containing 10 mM Ammonium Formate (pH 3.8) over 2.3 min at 0.8 mL/min.

C) Waters ACQUITY UPLC HSS C18 column (1.8 μm, 2.1×30 mm) eluting with a linear MeCN gradient containing 0.06% TFA (v/v) over 2.2 min at 0.9 mL/min.

D) Waters ACQUITY UPLC BEH C18 column (1.7 μm, 2.1×30 mm) eluting with a linear MeCN gradient containing 10 mM Ammonium Bicarbonate (pH 10) over 2.2 min at 0.75 mL/min.

E) Waters ACQUITY UPLC HSS C18 column (1.8 μm, 2.1×30 mm) eluting with a linear MeCN gradient containing 10 mM Ammonium Formate (pH 3.8) over 2.3 min at 0.8 mL/min. The eluents are warmed at 45° C. using a column preheater during the whole run.

F) Waters XSelect UPLC CSH C18 column (1.7 μm, 2.1×30 mm) eluting with a linear MeCN gradient containing 0.1% formic acid (v/v) over 2.0 min at 0.9 mL/min. The eluents are warmed at 45° C. using a column preheater during the whole run.

Abbreviations used in the examples include:

Ac: acetyl; AcOH: acetic acid; BEH: ethylene bridged hybrid; BOC or Boc: tert-butyloxycarbonyl; Bu: butyl; dba: dibenzylideneacetone; DCE: 1,2-dichloroethane; DCM: dichloromethane; DIPEA: diisopropylethylamine; DMEM: Dulbecco's modified Eagle's medium; DMF: N,N-dimethylformamide; DMSO: dimethylsulfoxide; dppf: 1,1'-diphenylphosphinylferrocene; eq or equiv: equivalents; Et: ethyl; $Et_2O$: diethyl ether; EtOAc: ethyl acetate; EtOH: ethanol; HATU: [O-(7-azabenzotriazol-1-yl)-1,1,3,3-tetramethyluronium hexafluorophosphate]; Hex: hexanes; HPLC: high performance liquid chromatography; HSS: high strength silica; $^i$Pr or i-Pr: 1-methylethyl(iso-propyl); iPrOH: isopropanol; Me: methyl; MeCN: acetonitrile; MeOH: methanol; MS: mass spectrometry; [M+H]$^+$: protonated molecular ion; MTBE or t-MBE: tert-butylmethyl ether; OBD: optimum bed density; PDA: photodiode array; Ph: phenyl; Pr: propyl; RP: reverse phase; RT: room temperature (18 to 22 PC); tert-butyl or t-butyl: 1,1-dimethylethyl; TEA: triethylamine; TFA: trifluoroacetic acid; THF: tetrahydrofuran; $t_R$: retention time and UPLC: ultraperformance liquid chromatography; Xantphos: 4,5-bis(diphenylphosphino)-9,9-dimethylxanthene Example A1

Preparation of Compound A1b

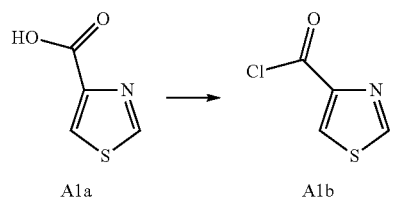 [SMILES: O=C(O)c1cscn1 ; O=C(Cl)c1cscn1]

A1a          A1b

A1a (10.0 g, 77.4 mmol, Combi Blocks) in DCM (100 mL) is treated with oxalyl chloride (66.0 mL, 619.5 mmol). DMF (599.6 μL, 7.7 mmol) is then added dropwise causing gas evolution. The reaction mixture is stirred overnight at RT, and then concentrated under reduced pressure, azeotroped with toluene (150 mL) and dried under high vacuum for 1 h to afford A1b which is used as is in subsequent reactions.

Example A2

Preparation of Compound 1018

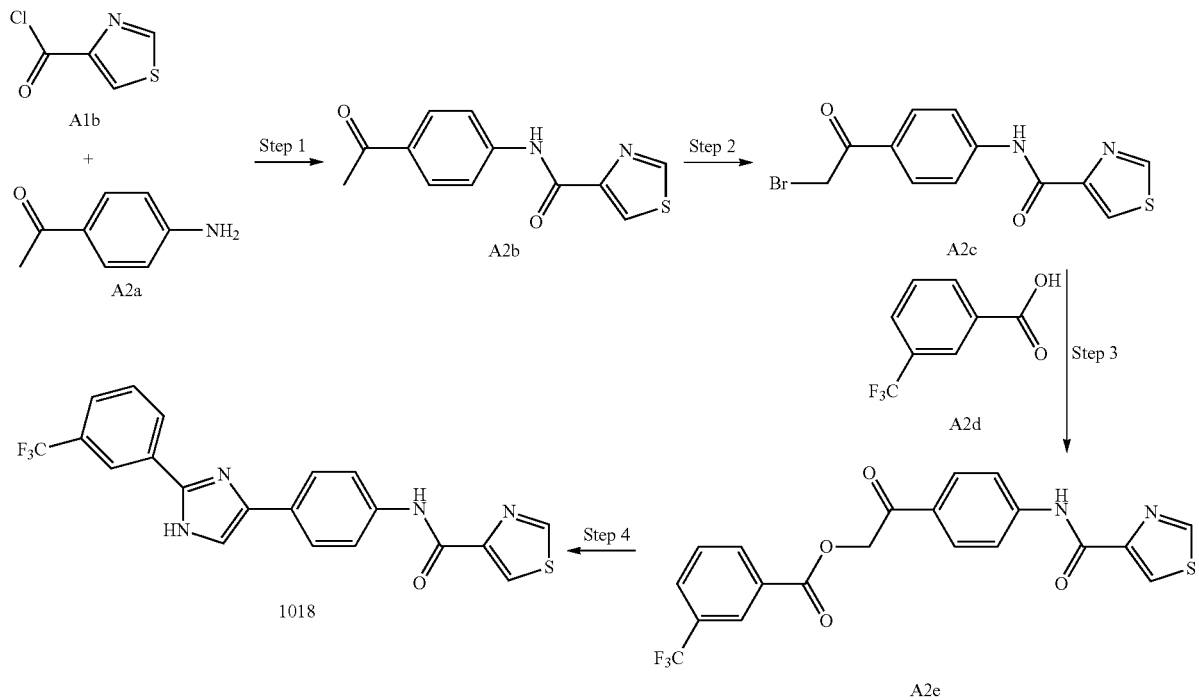

Step 1:
The aniline A2a (Aldrich, 4.0 g, 29 mmol) is dissolved in DCM (140 mL). The acid chloride A1b (4.4 g, 29 mmol) is added and the mixture is cooled to 0° C. DIPEA (6.2 mL, 36 mmol) is added. The reaction mixture is allowed to warm to RT and is stirred for 10 min. The reaction mixture is partitioned between DCM and a saturated aqueous solution of sodium bicarbonate. The organic layer is washed with water and brine, dried over $MgSO_4$, filtered and concentrated to give A2b.

Step 2:
To a solution of A2b (14 g, 57 mmol) in anhydrous THF (400 mL) is added phenyl trimethylammonium tribromide (22 g, 57 mmol). The mixture is stirred at RT for 4 h, then the resulting mixture is dissolved in EtOAc (1 L) and rinsed with water. The organic phase is separated and further washed with brine, dried over anhydrous $Na_2SO_4$, filtered, concentrated under reduced pressure and purified by flash column chromatography (0-6% EtOAc in $CH_2Cl_2$) to afford A2c.

Step 3:
A2c (300 mg, 0.92 mmol) and A2d (Alfa Aesar, 180 mg, 0.94 mmol) are dissolved in MeCN (4 mL) and are treated with DIPEA (0.2 mL, 1.2 mmol). The reaction mixture is stirred overnight and is then concentrated to dryness to give crude A2e, which is used as is in the next step.

Step 4:
In a sealable vessel, crude A2e and $NH_4OAc$ (650 mg, 8.5 mmol) are suspended in xylenes (8 mL) and the mixture is sealed and heated to 140° C. After 2 h, the reaction mixture is cooled to ~60° C. and is rotovapped to dryness. The residue is taken up in AcOH (6 mL) and purified by preparative HPLC (three injections, Sunfire column, TFA in MeCN/water). The fractions containing pure product are combined, frozen and lyophilized to give compound 1018.

Example A3

Preparation of Compound 1016

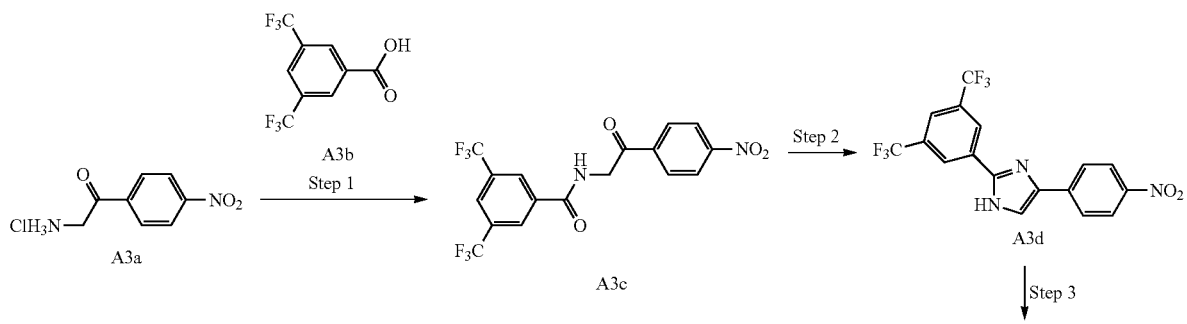

Step 1:

A solution of DIPEA (0.66 mL, 3.8 mmol), A3a (250 mg, 1.2 mmol) and A3b (Astatech) (300 mg, 1.2 mmol) in DMF (13 mL) is treated with HATU (540 mg, 1.4 mmol). The reaction mixture is stirred for 1 h and then is diluted with water and EtOAc. The organic layer is separated, washed with water (2×) and passed through a phase separator. The filtrate is evaporated to dryness and the residue is purified by Combiflash to give A3c.

Step 2:

In a sealable vessel, A3c (40 mg, 0.95 mmol) and NH$_4$OAc (40 mg, 0.52 mmol) are suspended in xylenes (1 mL) and the mixture is sealed and heated to 140° C. After 1 h, the reaction mixture is cooled to RT and partitioned between water and EtOAc. The organic layer is dried over Na$_2$SO$_4$ and concentrated to give A3d.

Step 3:

To solution of A3d (25 mg, 0.062 mmol) dissolved in THF (0.3 mL) and HCl (1N, 0.3 mL) is added Sn powder (18 mg, 0.16 mmol). The reaction mixture is stirred for 1 h and then is diluted with NaOH (1N, 0.35 uL) and water (10 mL). This mixture is stirred for 30 min and then is extracted with EtOAc. The organic layer is dried over Na$_2$SO$_4$ and concentrated to give A3e.

Step 4:

A solution of DIPEA (0.050 mL, 0.29 mmol), A1a (10 mg, 0.077 mmol) and A3e (20 mg, 0.54 mmol) in DMF (1 mL) at RT is treated with HATU (36 mg, 0.095 mmol). The reaction mixture is stirred for 2 h. In a separate reaction vessel, a solution of DIPEA (0.050 mL, 0.29 mmol) and A1a (10 mg, 0.077 mmol) in DMF (1 mL) at RT is treated with HATU (36 mg, 0.095 mmol). This mixture is stirred for 5 min before being added to the original reaction mixture. The reaction mixture is stirred for 30 min and then is diluted with AcOH (500 µL). The residue is purified by preparative HPLC to give compound 1016.

Example A4

Preparation of Compound A4b

To a solution of 4-aminophenylboronic acid pinacol ester A4a (500 mg, 2.3 mmol, Oakwood) in DMF (5 mL) is added 1,3-thiazole-4-carboxylic acid A1a (383.1 mg, 3.0 mmol, Combi Blocks), DIPEA (993.8 µL, 5.7 mmol) and HATU (1.2 g, 3.2 mmol). The reaction mixture is stirred for 45 min, and then water (15 mL) is added and the suspension is stirred overnight. The precipitate is filtered and rinsed with water (10 mL) and DCM (10 mL). The residue is dried under high vacuum and nitrogen flow for 15 min to afford A4b which is used as such in subsequent steps.

Example A5

Preparation of compound A5b

A solution of A4a (1.0 g, 4.6 mmol, Oakwood) in DMF (10 mL) is treated with A1a (766.3 mg, 6.0 mmol, Combi Blocks), DIPEA (2.0 mL, 11.4 mmol) and HATU (2.4 g, 6.4 mmol). The reaction mixture is stirred for 30 min, and then partitioned between water (30 mL) and EtOAc (50 mL). The layers are separated and the organic layer is washed with brine, dried over MgSO$_4$ and concentrated. The crude residue is triturated in water (40 mL) by sonication for 15 min. The suspension is filtered and rinsed with water (25 mL). The residue is dried under high vacuum and nitrogen flow for 1 h to provide A5b.

Example A6

Preparation of Compound A6c

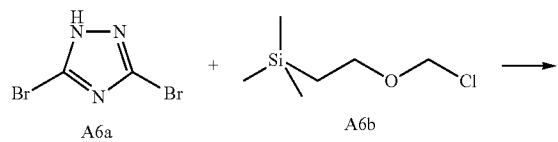

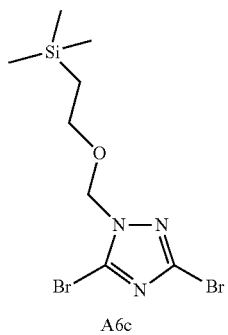

To a suspension of NaH (60% in mineral oil, 387.9 mg, 9.7 mmol) in THF (20 mL) at 0° C. is added a solution of A6a (2.0 g, 8.8 mmol, Matrix) in THF (20 mL). The reaction mixture is allowed to warm to RT and is stirred for 30 min. It is then cooled again to 0° C. and A6b (1.9 mL, 10.6 mmol, Combi Blocks) is added. The reaction mixture is stirred overnight at RT and diluted with EtOAc (50 mL). The organic layer is washed with water (30 mL) and brine (30 mL), dried over MgSO$_4$, and filtered. The filtrate is concentrated to give A6c which is used without further purification.

Example A7

Preparation of Compound 1070

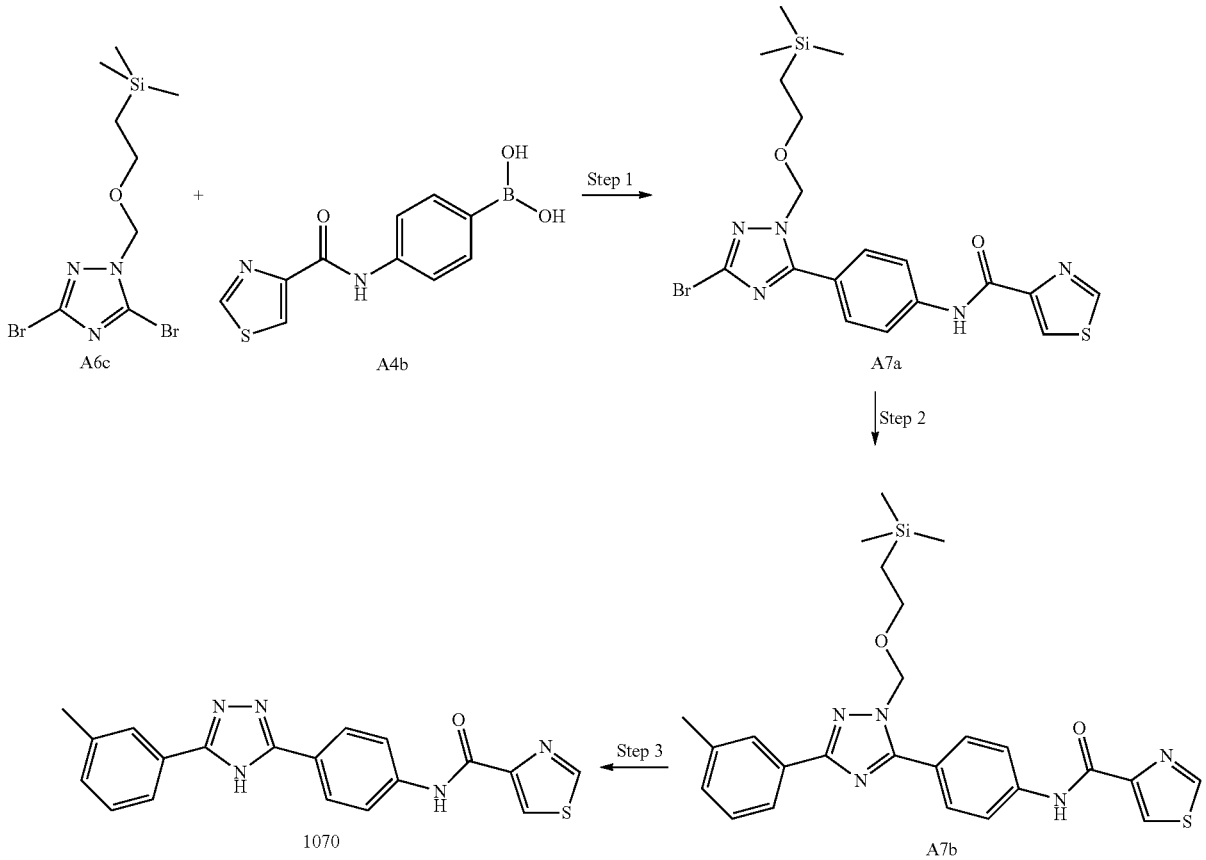

Step 1:

Intermediates A6c (620.0 mg, 1.7 mmol) and A4b (516.8 mg, 2.1 mmol), potassium carbonate (480.0 mg, 3.5 mmol), dioxane (7.5 mL) and water (2.5 mL) are charged in a microwave vial. The reaction mixture is degassed with argon for 5 min and Pd(PPh$_3$)$_4$ (200.6 mg, 0.17 mmol) is added. The vial is capped and heated in a microwave at 120° C. for 20 min. After cooling at RT, the reaction mixture is diluted with water (20 mL) and extracted with EtOAc (2×30 mL). The organic layers are combined, washed with brine, dried over MgSO$_4$, filtered and concentrated. The crude product is purified by CombiFlash (50% EtOAc/hexanes) to provide A7a.

Step 2:

Intermediate A7a (53.0 mg, 0.11 mmol), m-tolylboronic acid (18.0 mg, 0.13 mmol, Acros), potassium carbonate (30.5 mg, 0.22 mmol), dioxane (1.5 mL) and water (0.5 mL) are charged in a microwave vial. The reaction mixture is degassed with argon for 5 min and Pd(PPh$_3$)$_4$ (12.7 mg, 0.011 mmol) is added. The vial is capped and heated in a microwave at 120° C. for 20 min. After cooling at RT, the reaction mixture is partitioned between water (10 mL) and EtOAc (2×20 mL). The organic layers are combined, washed with brine, dried over MgSO$_4$, filtered and concentrated to provide the crude product A7b, which is taken to the next step as is.

Step 3:

Crude intermediate A7b (54.2 mg, 0.11 mmol) is dissolved in a mixture of DCM (2 mL) and TFA (2 mL). The reaction mixture is stirred at RT overnight. After completion, the solvents are removed in vacuo to give the crude product which is triturated in DCM (5 mL). The residue is filtered and rinsed with DCM (5 mL). MeCN and water are added and the mixture is frozen and lyophilized to afford compound 1070.

Example A8

Preparation of Compound 1034

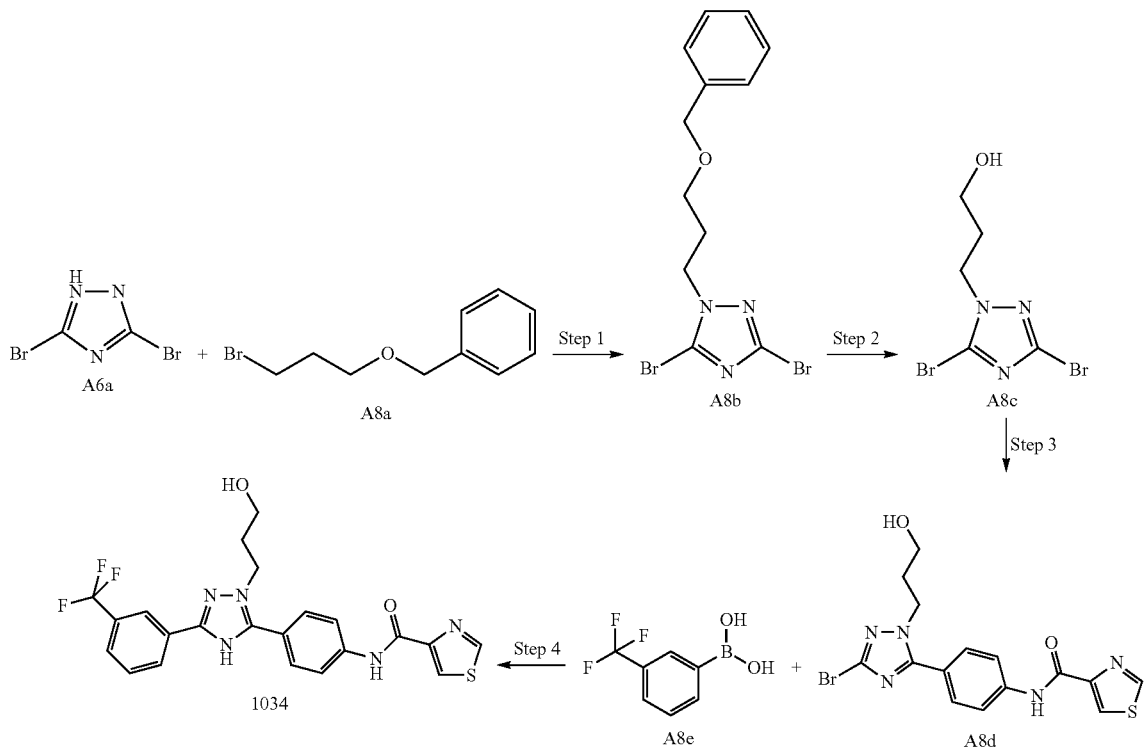

Step 1:

A solution of triazole A6a (5.0 g, 22.0 mmol, Matrix) in DMF (100 mL) at RT is treated with potassium carbonate (7.6 g, 55.1 mmol) and potassium iodide (365.9 mg, 2.2 mmol) before the addition of benzyl 3-bromopropyl ether A8a (4.3 mL, 24.2 mmol, Aldrich). The resulting mixture is heated to 75° C. overnight, allowed to cool to RT, and then EtOAc (400 ml) is added. The organic layer is washed with brine, water then again with brine and dried over MgSO$_4$. Solvent evaporation affords the crude product that is purified using the CombiFlash (20% EtOAc/hexanes) to afford A8b.

Step 2:

A solution of intermediate A8b (1.9 g, 5.1 mmol) in DCM (30 mL) at 0° C. is treated with boron tribromide (1.0 M in DCM, 16.9 mL, 16.9 mmol). The mixture is allowed to warm to RT and is stirred overnight. The mixture is cooled to 0° C., quenched with water, and then extracted with EtOAc (3×75 mL). The organic layers are combined, washed with brine and filtered using a phase separator. The crude product is purified using the CombiFlash (20% EtOAc/hexanes) to give intermediate A8c.

Step 3:

Intermediates A8c (500.0 mg, 1.8 mmol) and A4b (695.3 mg, 2.1 mmol), potassium carbonate (485.0 mg, 3.5 mmol), DMF (15 mL) and water (1.5 mL) are charged in a microwave vial. Pd(PPh$_3$)$_4$ (202.8 mg, 0.18 mmol) is added then the vial is capped and heated in microwave at 120° C. for 20 min. After cooling at RT, the reaction mixture is diluted with EtOAc (150 mL), washed with brine (3×75 mL) and filtered through a phase separator. The intermediate A8d is obtained by CombiFlash (100% EtOAc).

Step 4:

Intermediate A8d (300.0 mg, 0.74 mmol), 3-(trifluoromethyl)phenylboronic acid A8e (167.5 mg, 0.88 mmol, Frontier Scientific), potassium carbonate (203.1 mg, 1.5 mmol), dioxane (9 mL) and water (3 mL) are charged in a microwave vial. The reaction mixture is degassed with argon for 5 min and Pd(PPh$_3$)$_4$ (84.9 mg, 0.073 mmol) is added. The vial is capped and heated in a microwave at 120° C. for 20 min. After cooling at RT, the reaction mixture is diluted with water (25 mL) and extracted with EtOAc (2×45 mL). The organic layers are combined, washed with brine, dried over MgSO$_4$, filtered and concentrated. The crude product is purified by preparative HPLC. The pure fractions are pooled, frozen and lyophilized to afford compound 1034.

Example A9

Preparation of Compound 1121

Step 2:

A solution of intermediate A9b (863.4 mg, 3.2 mmol) in a mixture of acetone (65 mL) and water (10 mL) is treated with osmium tetraoxide (2.5 wt % in t-BuOH, 8.1 mL, 0.65 mmol) and 4-methylmorpholine N-oxide (454.7 mg, 3.9 mmol). The reaction mixture is stirred at RT overnight, concentrated, and then partitioned between water (60 mL) and 2-Me-THF (2×75 mL). The organic layers are combined, washed with 10% aqueous sodium thiosulfate and water, dried over MgSO$_4$, filtered and concentrated to provide intermediate A9c which is used without further purification.

Step 3:

Intermediates A9c (486.7 mg, 1.6 mmol) and A4b (640.8 mg, 1.9 mmol), potassium carbonate (447.0 mg, 3.2 mmol), dioxane (12 mL) and water (4 mL) are charged in a microwave vial. The reaction mixture is degassed with argon for 5 min and Pd(PPh$_3$)$_4$ (186.9 mg, 0.16 mmol) is added. The vial is capped and heated in a microwave at 120° C. for 20 min. After cooling at RT, the reaction mixture is diluted with water (35 mL) and extracted with EtOAc (2×60 mL). The organic layers are combined, washed with brine, dried over MgSO$_4$, filtered and concentrated. The crude product is purified by CombiFlash (100% EtOAc) to afford intermediate A9d.

Step 4:

Intermediate A9d (96.5 mg, 0.23 mmol), 3-chlorophenylboronic acid A9e (42.7 mg, 0.27 mmol, Frontier Scientific),

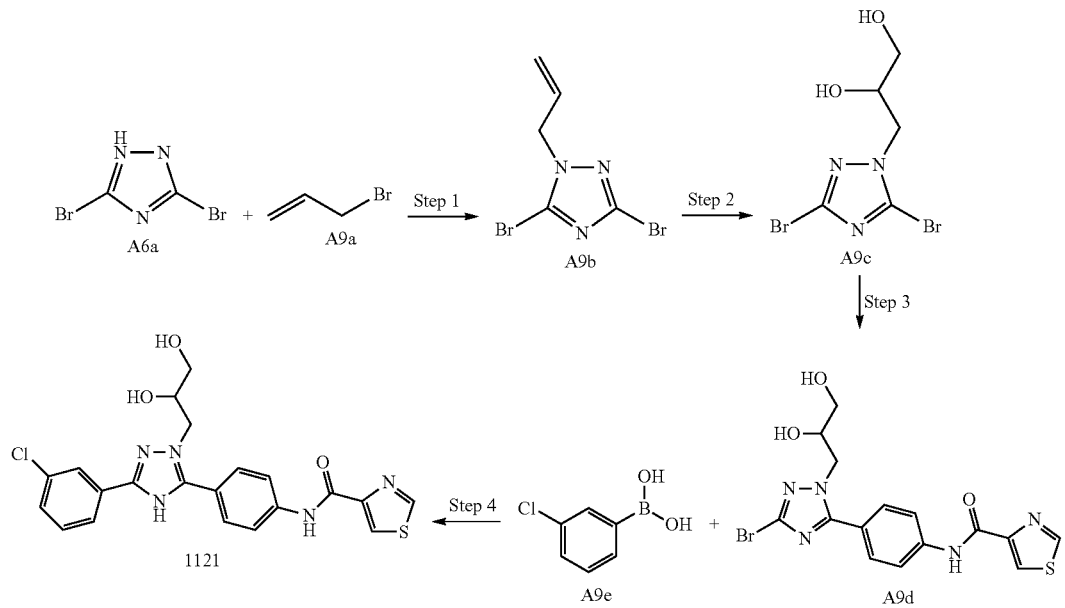

Step 1:

To a suspension of NaH (60% in mineral oil, 194.0 mg, 4.8 mmol) in THF (20 mL) at 0° C. is added a solution of triazole A6a (1.0 g, 4.4 mmol, Matrix) in THF (20 mL). The reaction mixture is allowed to warm to RT and is stirred for 30 min. It is then cooled again to 0° C. and allyl bromide A9a (762.9 µL, 8.8 mmol, Aldrich) is added. The reaction mixture is stirred overnight at RT and diluted with EtOAc (50 mL). The organic layer is washed with water (25 mL) and brine (25 mL), dried over MgSO$_4$, and filtered. The filtrate is concentrated to give A9b which is used as is in subsequent steps.

potassium carbonate (62.9 mg, 0.46 mmol), dioxane (1.5 mL) and water (0.5 mL) are charged in a microwave vial. The reaction mixture is degassed with argon for 5 min and Pd(PPh$_3$)$_4$ (26.3 mg, 0.023 mmol) is added. The vial is capped and heated in microwave at 120° C. for 20 min. After cooling to RT, the reaction mixture is diluted with water (15 mL) and extracted with EtOAc (2×20 mL). The organic layers are combined, washed with brine, dried over MgSO$_4$, filtered and concentrated. The crude product is purified by preparative HPLC. Pure fractions are pooled, frozen and lyophilized to give compound 1121.

Example A10

Preparation of Compounds 1114 and 1116

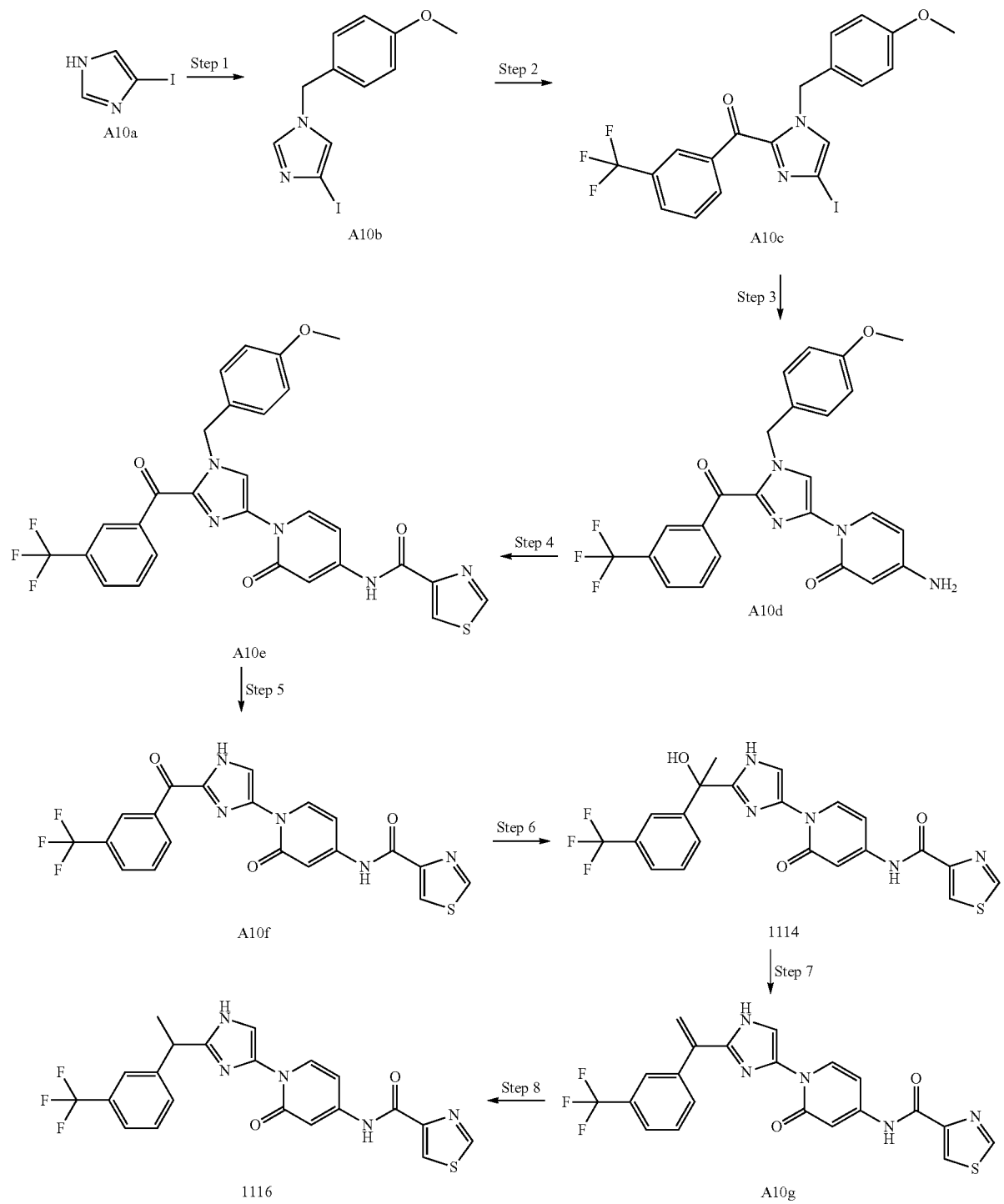

Step 1:

To a 0° C. mixture of 4-iodoimidazole A10a (5.0 g, 25.8 mmol) (Synthonix) in anhydrous THF (100 mL) is added NaH (60% in oil, 1.24 g, 30.9 mmol). The resulting mixture is stirred for 10 min before the addition of 4-methoxybenzyl chloride (4.37 mL, 32.2 mmol) (Aldrich). This mixture is allowed to warm to RT and is stirred overnight. An aqueous solution of saturated $NH_4Cl$ (50 mL) is added and this mixture is stirred for 10 min. The mixture is extracted with EtOAc (3×) and the layers are separated. The organic layer is washed with water and brine, dried with MgSO₄ and concentrated to provide crude material that is purified by Combiflash (20:80 to 80:20, EtOAc/hexanes) to provide A10b.

Step 2:

Intermediate A10b (2.0 g, 6.4 mmol) is dissolved in anhydrous MeCN (40 mL) and is treated with 3-(trifluoromethyl)benzoyl chloride (1.9 mL, 12.7 mmol) (Alfa Aesar) followed by Et₃N (1.8 mL, 12.7 mmol). The resulting mixture is heated to reflux for overnight, allowed to cool to RT and treated with water (15 mL). The resulting mixture is stirred for 5 min and then extracted with EtOAc (3×). The layers are separated and organic layer is washed with brine, dried with MgSO₄ and concentrated to provide crude material that is purified by Combiflash (0:100 to 50:50, EtOAc/hexanes) to provide A10c.

Step 3:

Intermediate A10c (971 mg, 2.0 mmol), 4-amino-2-hydroxypyridine (200 mg, 1.8 mmol) (Aconpharm), N,N-dimethylglycine (375 mg, 3.6 mmol) (Aldrich), CuI (86 mg, 0.45 mmol), K₂CO₃ (501 mg, 3.6 mmol) are dissolved into anhydrous DMSO (10 mL). The resulting mixture is bubbled under sonication using Ar(g) for 10 min before being heated to 130° C. for 10 h. The mixture is allowed to cool to RT, diluted with EtOAc (150 mL), washed with brine (3×), dried with MgSO₄ and concentrated to provide crude material that is triturated using t-BME to afford A10d.

Step 4:

Intermediate A10d (257 mg, 0.55 mmol) is dissolved into anhydrous MeCN (4 mL) before being treated with acid chloride A1b (113 mg, 0.77 mmol), and DIPEA (0.19 mL, 1.1 mmol). The resulting mixture is stirred for 2 h at RT, filtered and the residue is rinsed with MeCN to afford A10e.

Step 5:

Intermediate A10e (1.95 g, 3.4 mmol) is dissolved into anhydrous DCM (10 mL) before being treated with TFA (10 mL). The resulting mixture is stirred for overnight at 75° C., allowed to cool and concentrated to dryness. It is co-evaporated over toluene before being neutralized by addition of 1N NaOH. The resulting mixture is sonicated and filtered. The residue is rinsed with water and MeOH and dried under vacuum to afford A10f.

Step 6:

Intermediate A10f (100 mg, 0.22 mmol) is dissolved into anhydrous THF (2 mL) at RT before being treated with MeMgBr (0.47 mL, 0.65 mmol) (1.4M in THF/toluene (1:3)). The resulting mixture is stirred for 1 h, and then an aqueous solution of saturated NH₄Cl (2 mL) is added. The resulting mixture is stirred for 30 min, then water is added. This mixture is extracted with EtOAc (3×) and the layers are separated. The organic layer is washed with water, brine, dried with MgSO₄ and concentrated to provide crude material that is purified by preparative RP-HPLC to provide compound 1114.

Step 7:

A solution of compound 1114 (100 mg, 0.22 mmol) in TFA (3.0 ml) is placed in a sealed reaction vessel and is heated to 70° C. for 3 h and then is concentrated to dryness to give A10g.

Step 8:

A solution of A10g (100 mg, 0.22 mmol) in iPrOH (10 mL) is treated with ammonium formate (200 mg, 3.3 mmol) and Pd/C (5% w/w, 200 mg). The resulting mixture is stirred at 80° C. for 5 h, cooled to RT and filtered through an Acrodisc. The filtrate is used directly to purify the product by preparative HPLC to give compound 1116.

Example A11

Preparation of Compounds 1092 and 1087

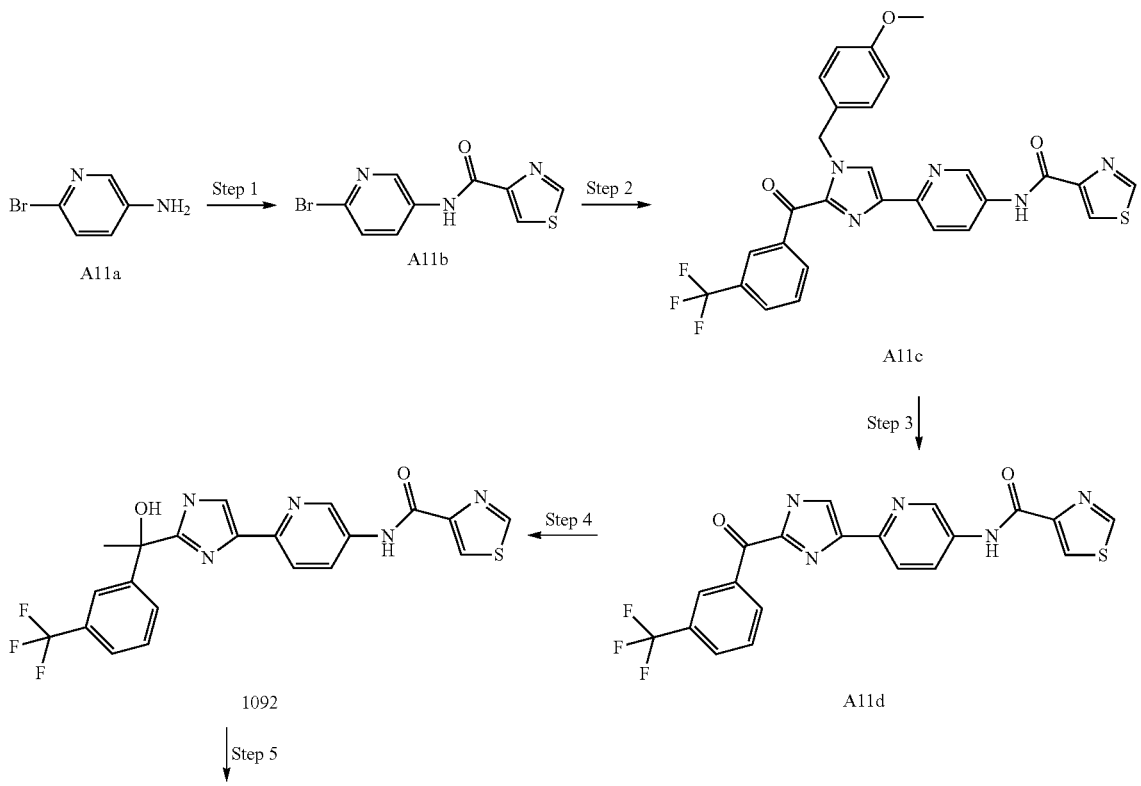

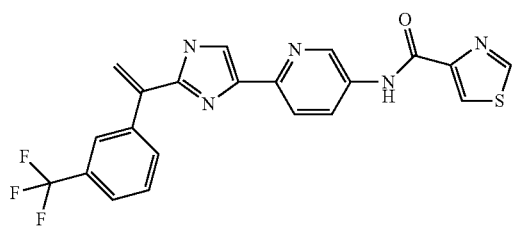

A11e

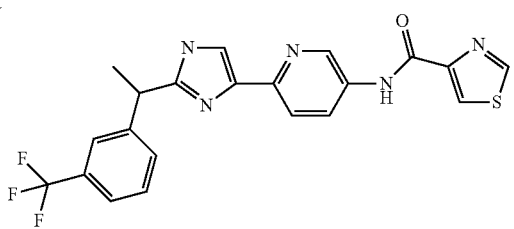

1087

Step 1:

5-amino-2-bromopyridine A11a (1.0 g, 5.8 mmol) (Oakwood) is suspended in DCM (15 mL) at RT before being treated with acid chloride A1b (981 mg, 6.6 mmol) and DIPEA (2.5 mL, 14.5 mmol). The resulting mixture is stirred overnight at RT, and then an aqueous solution of saturated NaHCO$_3$ (5 ml) is added. The mixture is extracted with EtOAc (3×) and the layers are separated. The organic layer is washed with brine, dried with MgSO$_4$ and concentrated to provide A11b.

Step 2:

Intermediate A11b (500 mg, 1.0 mmol) is dissolved in anhydrous dioxane (5 mL) and treated with PdCl$_2$(PPh$_3$)$_2$ (72 mg, 0.10 mmol) (Aldrich) and hexadimethyltin (0.43 mL, 2.1 mmol) (Aldrich). The resulting mixture is heated to 90° C. for 4 h, and then allowed to cool to RT before being treated with A10c (394 mg, 1.4 mmol) and Pd[(PPh$_3$)]$_4$. The resulting mixture is heated to 110° C. for 6 h, allowed to cool to RT, and then water (5 mL) is added. The mixture is extracted with EtOAc (3×) and the layers are separated. The organic layer is washed with brine, dried with MgSO$_4$ and concentrated to provide crude material that is triturated using MeOH to give A11c.

Step 3:

Intermediate A11c (50 mg, 0.09 mmol) is dissolved into anhydrous DCM (0.7 mL) before being treated with TFA (0.7 mL). The resulting mixture is stirred overnight at 75° C., then is allowed to cool to RT and is concentrated to dryness. The residue is dissolved in EtOAc, basified using 5N NaOH and extracted with EtOAc. The organic layer is washed with brine, dried with MgSO$_4$ and concentrated to dryness to provide A11d.

Step 4:

Intermediate A11d (40 mg, 0.09 mmol) is dissolved in anhydrous THF (2 mL) at RT before being treated with MeMgBr (0.26 mL, 0.36 mmol) (1.4M in THF/toluene (1:3)). The resulting mixture is stirred for 1 h, and then an aqueous solution of saturated NH$_4$Cl (2 mL) is added. This mixture is stirred for 30 min, and then water is added. The mixture is extracted with EtOAc (3×) and the layers are separated. The organic layer is washed with water, brine, dried with MgSO$_4$ and concentrated to provide crude material that is purified by preparative RP-HPLC to provide compound 1092.

Step 5:

Intermediate A11e is made from compound 1092 by analogy to intermediate A10g, following step 7 from Example A10.

Step 6:

Compound 1087 is made from A11e by analogy to compound 1116, following step 8 from Example A10.

Example A12

Preparation of Compounds 1129 and 1120

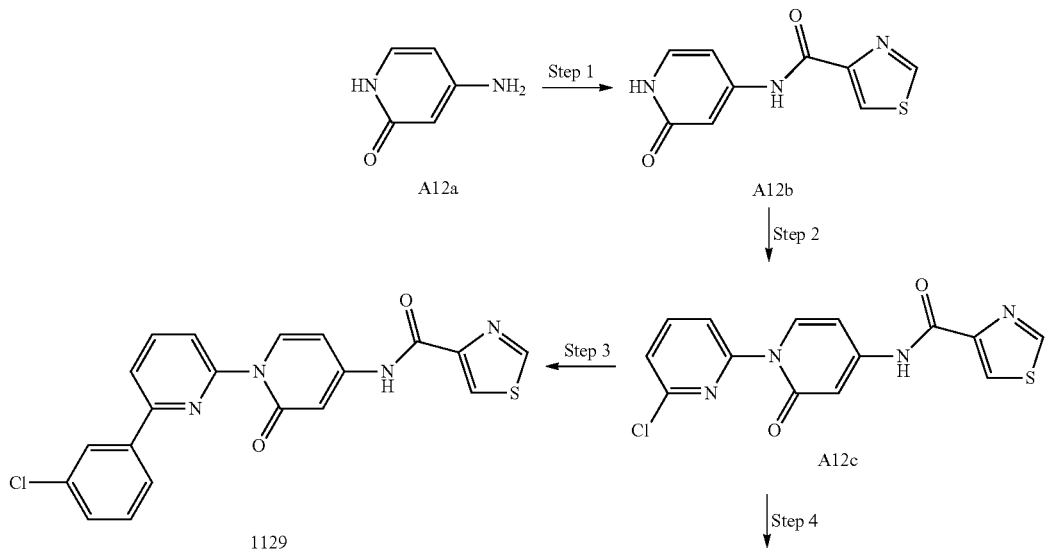

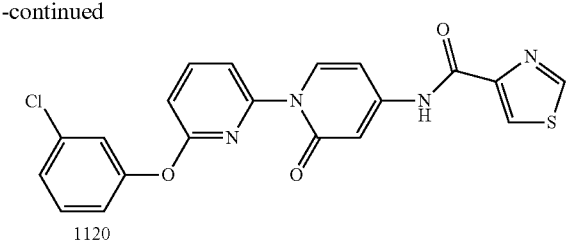

1120

Step 1:

4-amino-2-hydroxypyridine A12a (1.5 g, 14.0 mmol) (Aconpharm) is dissolved in anhydrous MeCN (50 mL) at RT before being treated with acid chloride A1b (10.1 g, 68.1 mmol) and DIPEA (23.7 mL, 136.2 mmol). The resulting mixture is stirred at RT overnight, and then diluted with THF (20 mL) and MeOH (10 mL). The resulting solution is treated with 10N NaOH (4.0 mL, 40 mmol) at RT and then is stirred for 20 min. The mixture is filtered and rinsed with water and acetone to afford A12b.

Step 2:

Intermediate A12b (1.3 g, 5.9 mmol) is dissolved in anhydrous DMF (13 mL) and is treated with $Cs_2CO_3$ (3.83 g, 11.8 mmol) and 2,6-dichloropyridine (1.0 g, 7.1 mmol). The resulting mixture is heated to 100° C. for 24 h, allowed to cool to RT and then diluted with EtOAc (70 mL), washed with brine, and with water. The organic layer with solid at the interface is collected and evaporated. The resulting mixture is triturated with MeOH and filtered to give A12c.

Step 3:

Intermediate A12c (50 mg, 0.15 mmol) is dissolved in DMF (2 mL) and treated with $K_2CO_3$ (82.9 mg, 0.60 mmol), 3-chlorophenyl boronic acid (30.5 mg, 0.20 mmol), $PdCl_2(PPh_3)_2$ (15.8 mg, 0.02 mmol) and water (0.2 mL). The resulting mixture is heated in a microwave for 20 min at 130° C., allowed to cool to RT, filtered with Acrodisc filters and directly purified by preparative RP-HPLC to provide compound 1129.

Step 4:

A mixture of A12c (40 mg, 0.12 mmol), $K_2CO_3$ (66 mg, 0.48 mmol) and m-chlorophenol (Aldrich, 20 mg, 0.16 mmol) in DMF (2 mL) is placed in a sealed reaction vessel and is heated to 160° C. and stirred overnight. The resulting mixture is cooled to RT, filtered through an Acrodisc and the filtrate is used directly to purify the product by preparative HPLC to give compound 1120.

Example A13

Preparation of compound 1130

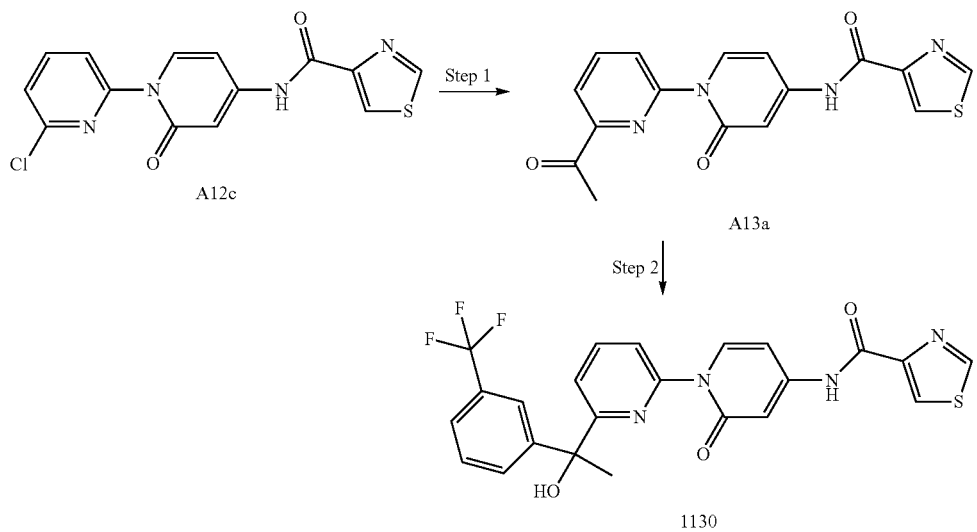

Step 1:

Intermediate A12c (401 mg, 1.2 mmol) is dissolved in anhydrous DMF (10 mL) and is treated with $PdCl_2(PPh_3)_2$ (126.9 mg, 0.18 mmol) and with 1-ethoxyvinyl-tri-n-butyltin (0.53 mL, 1.57 mmol). The resulting mixture is heated in a microwave for 25 min at 145° C., allowed to cool, treated with 1N HCl (3.6 mL, 3.6 mmol) and stirred at RT for 2 h. The mixture is then basified using 1N NaOH and filtered. The residue is washed with water, MeOH, triturated over EtOAc and filtered to afford A13a.

Step 2:

A solution of 1-iodo-trifluoromethylbenzene (400 mg, 1.47 mmol) (Aldrich) in anhydrous THF (5 mL) at RT is treated with isopropylmagnesium chloride, lithium chloride complex (1.80 mL, 2.35 mmol, 1.3 M solution in THF). The resulting mixture is stirred at RT for 15 min, and then 2 mL of this solution is added to a solution of intermediate A13a (50 mg, 0.15 mmol) in anhydrous THF (1 mL). This mixture is stirred for 30 min, and then an aqueous solution of saturated $NH_4Cl$ (2 ml) is added. This mixture is stirred for 10 min, and then water is added. The mixture is extracted with EtOAc (3×)

and the layers are separated. The organic layer is washed with water, brine, dried with MgSO4 and concentrated to provide crude material that is purified by preparative RP-HPLC to provide compound 1130.

Example A14

Preparation of compound 1059

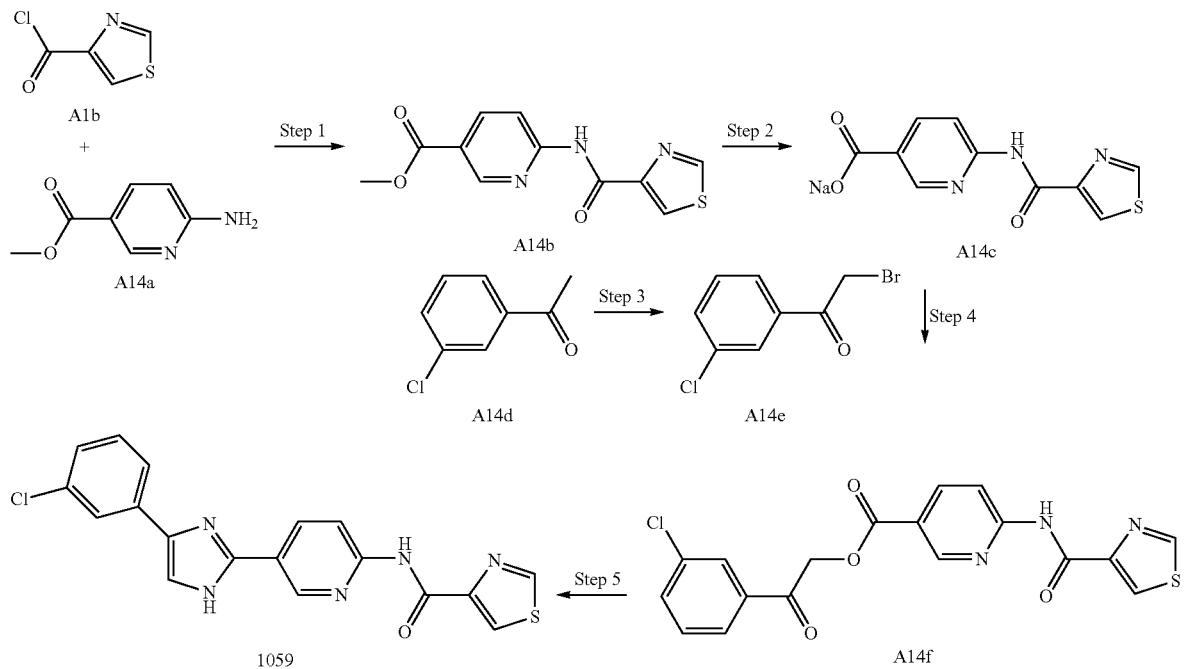

Step 1:
4-amino-2-hydroxypyridine A14a (1.5 g, 9.9 mmol) (Alfa) is dissolved in DCM (40 mL) at RT before being treated with acid chloride A1b (1.9 g, 13 mmol) and DIPEA (3.4 mL, 20 mmol). The resulting mixture is stirred at RT for 30 min and then is diluted with DCM and washed with saturated NaHCO3 and brine. The organic layer is dried over MgSO4 and evaporated to dryness. The residue is purified by Combiflash to give A14b.

Step 2:
A14b (2.1 g, 8.0 mmol) is dissolved in MeOH (8 mL), THF (25 mL), water (6 mL) and aqueous NaOH (5N, 1.8 mL, 8.8 mmol) is added. The reaction mixture is stirred at RT overnight. The organic solvents are removed by rotoevaporation and the resulting aqueous solution is frozen and lyophilized to give A14c.

Step 3:
A14d (5.0 g, 32 mmol) is dissolved in THF (170 mL) and treated with (PhMe3N)Br3 (12 g, 32 mmol). The reaction mixture is stirred at RT. After 30 min, the mixture is partitioned between EtOAc and water. The organic layer is separated and washed with brine. The product is purified by Combiflash and the resulting residue is re-crystallized from EtOAc/hexanes to give A14e.

Step 4:
A14e (100 mg, 0.44 mmol) and A14c (50 mg, 0.18 mmol) are dissolved in MeCN (2 mL) before the addition of DIPEA (0.06 mL, 0.4 mmol). The reaction mixture is heated to 50° C. and is stirred for 3 days. The mixture is cooled to RT and is then concentrated to dryness to give crude A14f, which is used as is in the next step.

Step 5:
In a sealable vessel, A14f and NH4OAc (280 mg, 3.7 mmol) are suspended in toluene (2 mL) and the mixture is sealed and heated to 100° C. The mixture is stirred overnight, cooled to RT and rotovapped to dryness. The residue is taken up in DMSO (2 mL) and purified by preparative HPLC. Fractions containing pure product are combined, frozen and lyophilized to give compound 1059.

Example A15

Preparation of Compound 1045

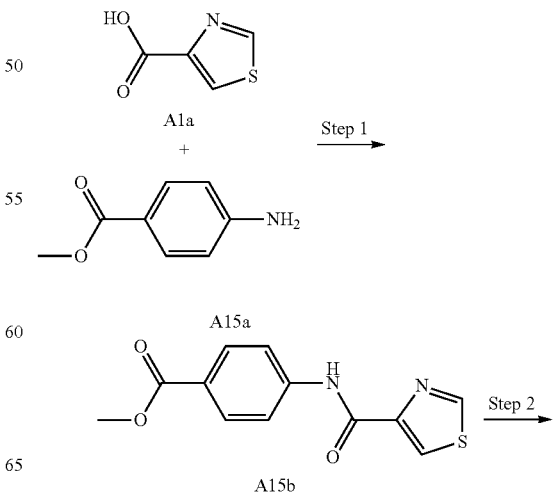

-continued

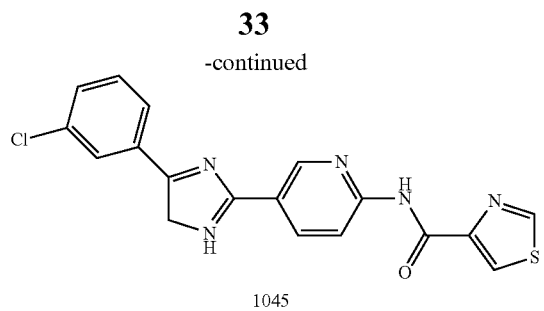

1045

Step 1:

A solution of DIPEA (1.2 mL, 7.0 mmol), A15a (Aldrich, 530 mg, 3.5 mmol) and A1a (300 mg, 2.3 mmol) in DMF (14 mL) is treated with HATU (1.3 g, 3.5 mmol). The mixture is stirred for 2 h and then is diluted with water and EtOAc. The organic layer is separated and washed with water (2×). The organic layer is passed through a phase separator and the filtrate evaporated to dryness. The product is purified by Combiflash to give A15b.

Step 2:

Compound 1045 is made from A15b by analogy to compound 1059, following steps 2-5 from Example A14.

Example A16

Preparation of Compound 1052

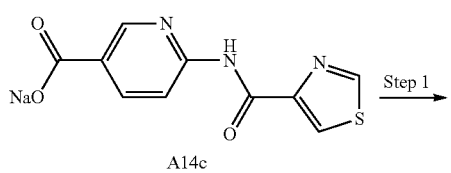

A14c

-continued

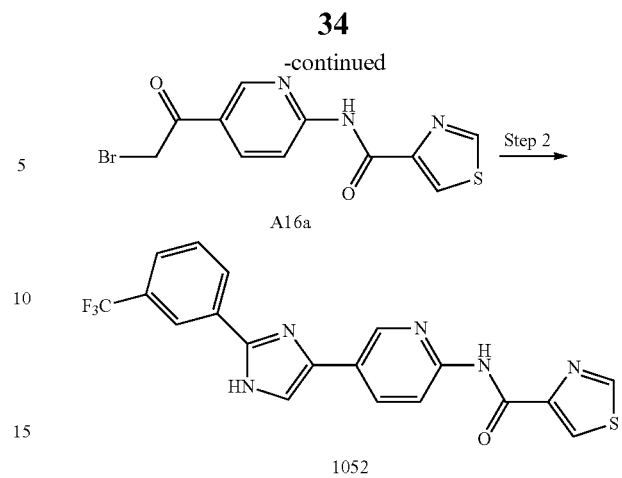

1052

Step 1:

Carboxylate A14c (1.0 g, 3.7 mmol) is dissolved in DCM (20 mL) and oxalyl chloride (4.6 mL, 9.2 mmol) is added along with a drop of DMF. The reaction mixture is stirred for 1 h and then is concentrated. DCM (20 mL) is added followed by diazomethane in ether (1.6 M, 25 mL, 40 mmol). The reaction mixture is stirred for 2 h before being concentrated. The mixture is taken up in DCM (20 mL) and HBr in AcOH (33%, 0.76 mL, 4.4 mmol) is added. The mixture is stirred for 20 min. The reaction mixture is partitioned between EtOAc and a saturated aqueous solution of sodium bicarbonate. The organic layer is washed with water and brine, dried over MgSO$_4$, filtered and concentrated. The product is purified by Combiflash to give A16a.

Step 2:

Compound 1052 is made from A16a by analogy to compound 1018, following steps 3 and 4 from Example A2.

Example A17

Preparation of Compound 1103

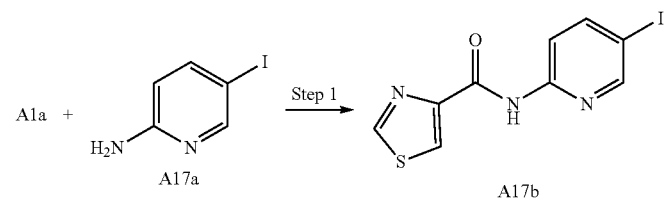

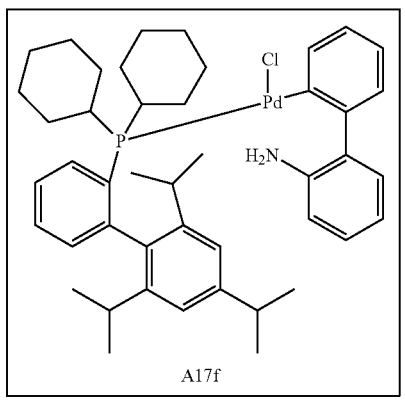

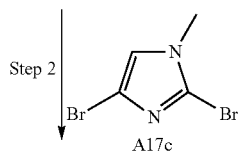

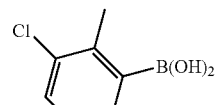

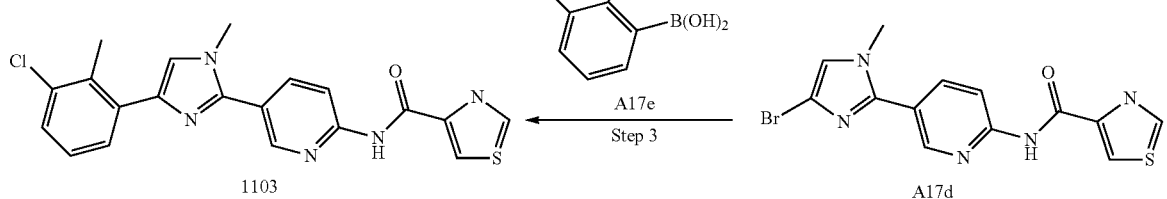

Step 1:

A solution of DIPEA (1.2 mL, 7.0 mmol), A17a (Aldrich, 530 mg, 3.5 mmol) and A1a (300 mg, 2.3 mmol) in DMF (14 mL) is treated with HATU (1.3 g, 3.5 mmol). The mixture is stirred for 2 h and then is diluted with water and EtOAc. The organic layer is separated, washed with water (2×) and passed through a phase separator. The filtrate is evaporated to dryness and the residue is purified by Combiflash to give A17b.

Step 2:

Bis(pinacolate)diboron (650 mg, 2.6 mmol), potassium acetate (580 mg, 5.9 mmol) and A17b (650 mg, 2.0 mmol) are mixed in DMSO (10 mL). The reaction mixture is purged with nitrogen for 10 min with sonication. Pd(dppf)Cl$_2$/DCM complex (160 mg, 0.20 mmol) is added and the mixture is stirred at 95° C. for 2 h. Water and EtOAc are added to the mixture and the insoluble matter is removed by filtration on borosilicate filters. The organic layer is separated, washed with water (3×) and brine, dried with MgSO$_4$ and concentrated. The residue is dissolved in DMF (10 mL) and a solution of Na$_2$CO$_3$ (2M, 2.9 mL, 5.9 mmol) and 2,4-dibromo-1-methyl-1H-imidazole A17c (Aldrich, 570 mg, 2.4 mmol) is added. The reaction mixture is purged with nitrogen while sonicating for 10 min. Pd[PPh$_3$]$_4$ (100 mg, 0.08 mmol) is added and the reaction mixture is heated to 110° C. for 6 h. The mixture is diluted in EtOAc and water and the phases are separated. The organic phase is washed with water (3×) and brine, dried over MgSO$_4$ and concentrated. The product is purified by Combiflash to give A17d.

Step 3:

Intermediate A17d (65 mg, 0.18 mmol), 3-chloro-2-methylphenylboronic acid A17e (46 mg, 0.27 mmol, Cuschem), potassium phosphate (0.5 M, 0.7 mL, 0.4 mmol), and THF (1.5 mL) are charged in a microwave vial. The reaction mixture is purged with nitrogen for 10 min and A17f (prepared according to *J. Am. Chem. Soc.* 2010, 132, 14073; 14 mg, 0.02 mmol) is added. The vial is capped and heated in a microwave at 120° C. for 15 min. After cooling to RT, the reaction mixture is concentrated to dryness, re-dissolved in MeOH/water and filtered through an Acrodisc. The residue is purified by preparative HPLC. Pure fractions are pooled, frozen and lyophilized to give compound 1103.

Example A18

Preparation of Compound 1097

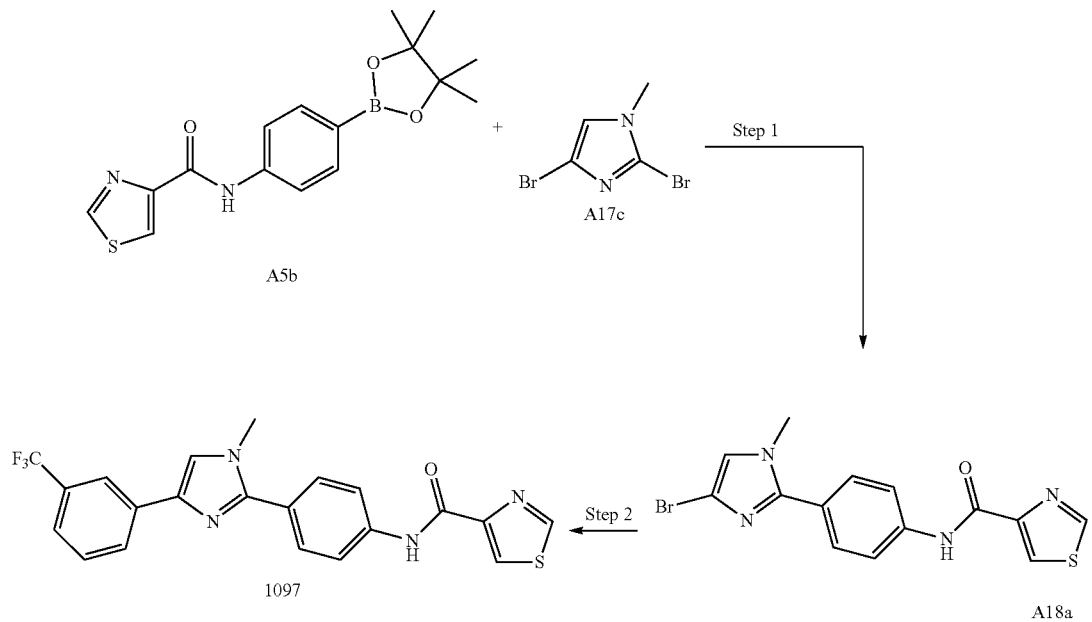

Step 1:

Intermediate A5b (740 mg, 2.3 mmol) is dissolved in dioxane (16 mL) and water (5.4 mL) and K$_2$CO$_3$ (520 mg, 3.8 mmol) and A17c (Aldrich, 450 mg, 1.9 mmol) are added. The reaction mixture is purged with nitrogen while sonicating for 10 min. Pd[PPh$_3$]$_4$ (220 mg, 0.19 mmol) is added and the reaction mixture is heated in a microwave to 120° C. for 20 min. The mixture is diluted in EtOAc and water and the phases are separated. The organic phase is washed with water (3×) and brine, dried over MgSO$_4$ and concentrated. The residue is purified by combiflash to give A18a.

Step 2:

Compound 1097 is made from A18a by analogy to compound 1103, following step 3 from Example A17.

Example A19

Preparation of Compound 1096

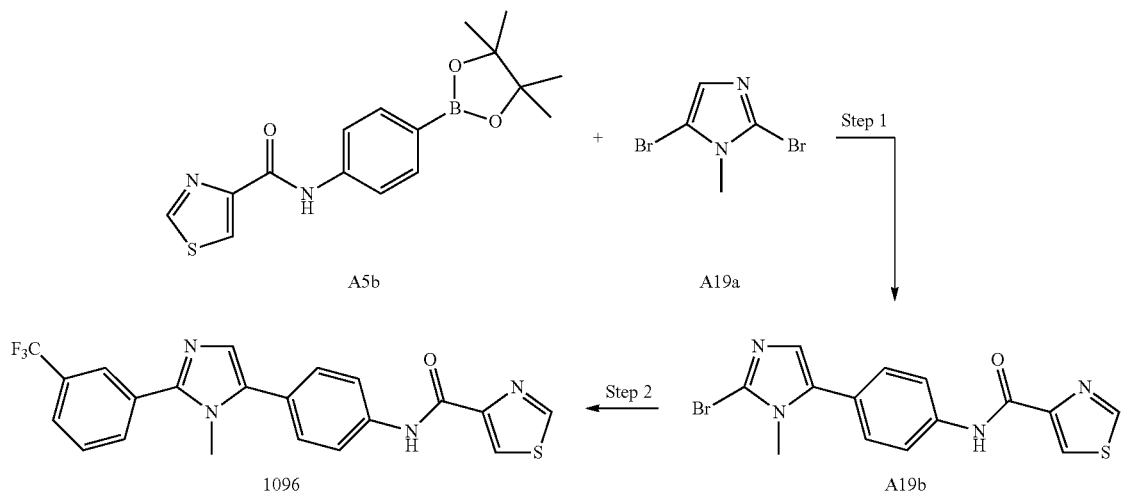

Step 1:
Intermediate A5b (170 mg, 0.50 mmol) is dissolved in dioxane (5.7 mL) and water (0.76 mL) and $K_2CO_3$ (120 mg, 0.83 mmol) and A19a (Combi-Blocks, 100 mg, 0.42 mmol) is added. The reaction mixture is purged with nitrogen while sonicating for 10 min. Pd[PPh$_3$]$_4$ (48 mg, 0.04 mmol) is added and the reaction mixture is heated in a microwave to 120° C. for 20 min. The mixture is diluted in EtOAc and water and the phases are separated. The organic phase is washed with water (3×) and brine, dried over MgSO$_4$ and concentrated. The product is purified by Combiflash to give A19b.

Step 2:
Compound 1096 is made from A19b by analogy to compound 1103, following step 3 from Example A17.

Example A20

Preparation of Compound 1098

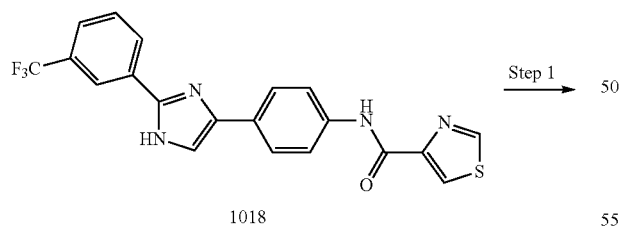

-continued

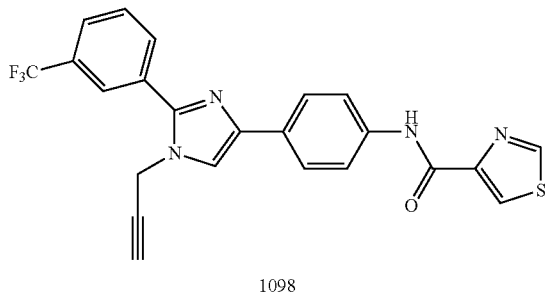

Step 1:
Compound 1018 (9 mg, 0.02 mmol) is dissolved in DMF (0.3 mL) and $K_2CO_3$ (6 mg, 0.04 mmol) followed by propargyl bromide (Alfa, 3 µL, 0.03 mmol) are added. After 6 h, the reaction mixture is diluted with MeOH (1 mL) followed by water (20 mL). The resulting solid is collected by filtration, re-dissolved in MeCN/water, frozen and lyophilized to give compound 1098.

Example A21

Preparation of Compound 1086

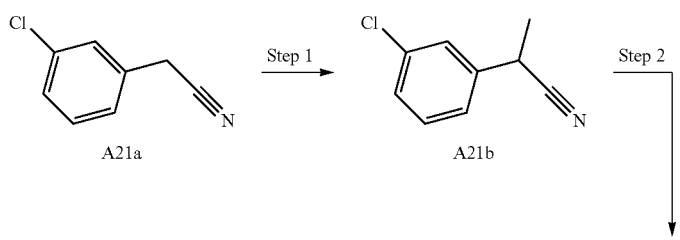

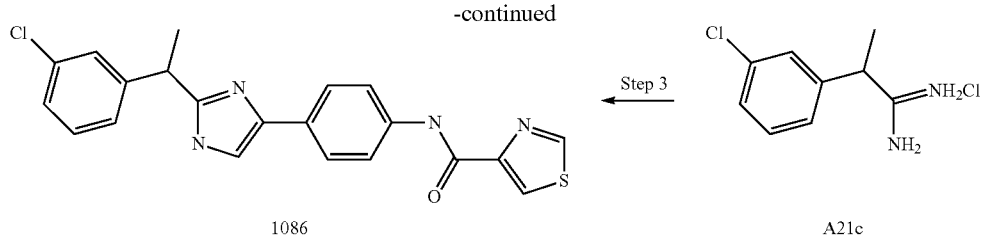

Step 1:

To a solution of the nitrile A21a (Alfa, 1.0 g, 6.6 mmol) in dry DMF (50 mL) at 0° C. is added solid NaH (100%, 174 mg, 7.3 mmol). The mixture is stirred for 1 h at 0° C. and then MeI (0.42 mL, 7.3 mmol) is added. The mixture is stirred overnight and then diluted with water and Et$_2$O. The organic layer is washed with water (2×), dried over MgSO$_4$ and concentrated. The residue is purified by Combiflash to give A21 b.

Step 2:

Ammonium chloride (0.62 g, 12 mmol) in PhMe (23 mL) at 0° C. is added to a solution of AlMe$_3$ (Aldrich 2M in toluene, 5.8 mL, 12 mmol) (Caution: evolution of gas). After stirring for 15 min, the mixture is warmed to RT and a solution of A21b (390 mg, 2.2 mmol) in toluene (5 mL) is added. The reaction mixture is heated to 80° C. After stirring overnight, the mixture is cooled to 0° C. and quenched with MeOH (40 mL). This mixture is stirred for 30 min and then filtered through borosilicate filterpaper. The filtrate is concentrated and the product A21c is purified by Combiflash using 10% MeOH/DCM as eluent.

Step 3:

To a suspension of the A21c (54 mg, 0.30 mmol) and A2c (80 mg, 0.15 mmol) in MeCN (1.5 mL) is added DIPEA (0.02 mL, 0.15 mmol) and the reaction is heated to 50° C. After stirring for 1 h, the reaction mixture is cooled to RT and diluted with 1:1 MeOH/water to a total volume of 2 mL. This mixture is filtered through an Acrodisc and the residue purified by preparative HPLC to give compound 1086.

Example A22

Preparation of Compounds 1118 and 1119

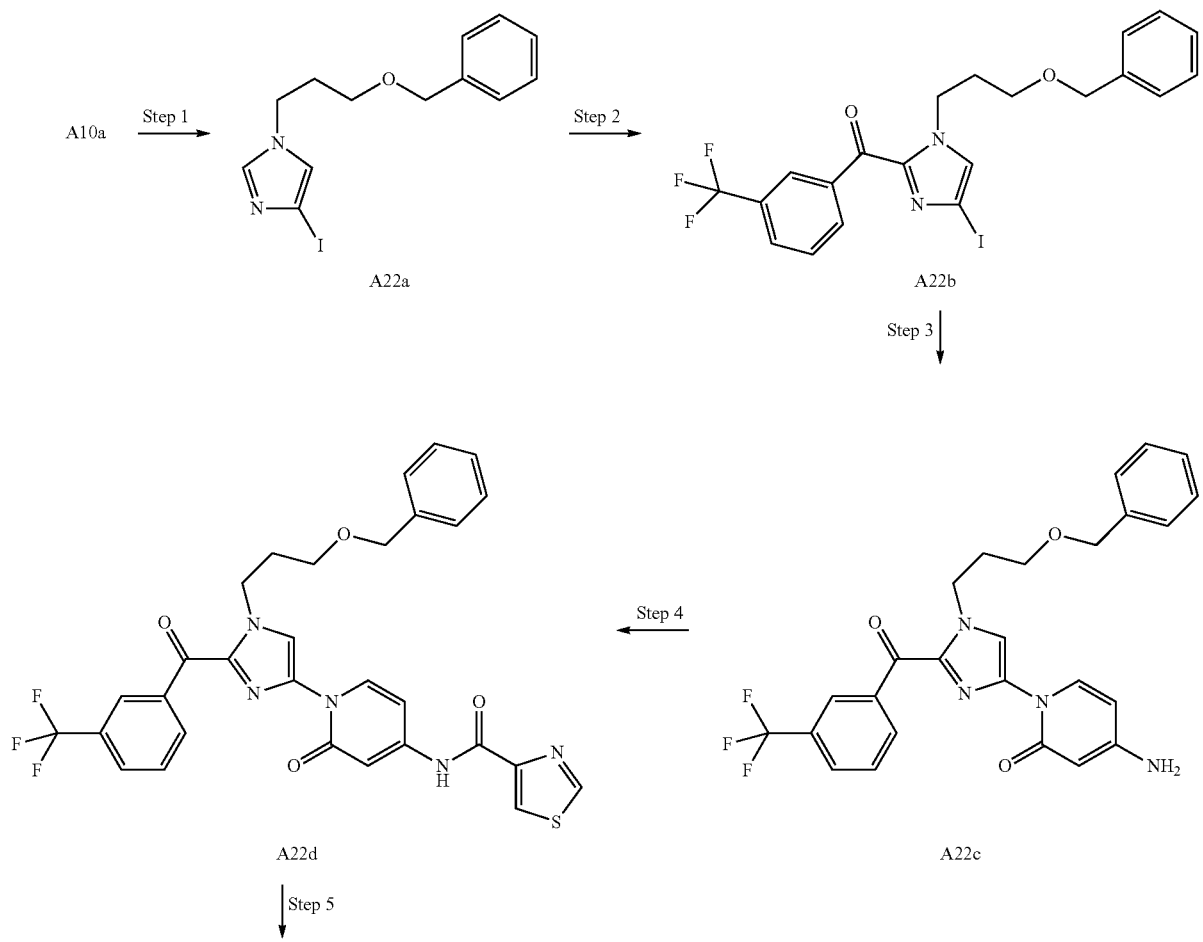

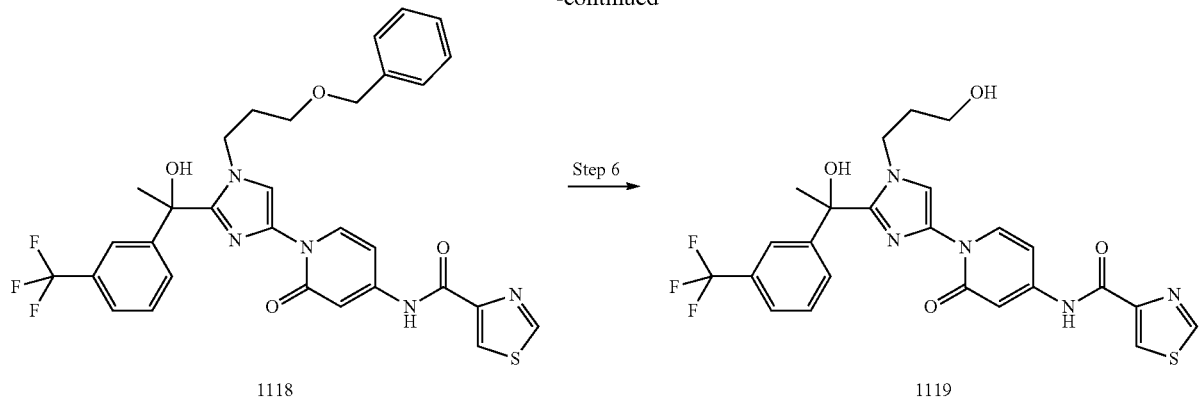

1118 → Step 6 → 1119

Step 1:

To a 0° C. mixture of A10a (2.0 g, 10.3 mmol) (Synthonix) in anhydrous THF (40 mL) is added NaH (60% in oil, 495 mg, 12.4 mmol). The resulting mixture is stirred for 10 min before the addition of (3-bromo-propoxymethyl)benzene (2.3 mL, 12.9 mmol) (Chembridge-BB). The resulting mixture is allowed to warm to RT, and then is stirred overnight. An aqueous solution of saturated NH₄Cl (20 mL) is added, and this mixture is stirred for 10 min. The mixture is extracted with EtOAc (3×) and the layers are separated. The organic layer is washed with water, brine, dried with MgSO₄ and concentrated to provide crude material that is purified by Combiflash (20:80 to 80:20, EtOAc/hexanes) to provide A22a.

Step 2:

Intermediate A22a (1.9 g, 5.5 mmol) is dissolved in anhydrous MeCN (40 mL) and is treated with 3-(trifluoromethyl)benzoyl chloride (1.6 mL, 11.0 mmol) (Alfa Aesar) followed by Et₃N (1.5 mL, 11.0 mmol) (Anachemia). The resulting mixture is heated to reflux for overnight, allowed to cool to RT and is treated with water (15 mL). The resulting mixture is stirred for 5 min, and then extracted with EtOAc (3×). The layers are separated and organic layer is washed with brine, dried with MgSO₄ and concentrated to provide crude material that is purified by Combiflash (0:100 to 50:50, EtOAc/hexanes) to provide A22b.

Step 3:

Intermediate A22b (514 mg, 1.0 mmol), 4-amino-2-hydroxypyridine (100 mg, 0.91 mmol) (Aconpharm), N,N-dimethylglycine (187 mg, 1.82 mmol) (Aldrich), CuI (43 mg, 0.23 mmol) (Aldrich), K₂CO₃ (251 mg, 1.82 mmol) (Fluka) are dissolved into anhydrous DMSO (10 mL). The resulting mixture is bubbled under sonication using Ar(g) for 10 min before being heated to 130° C. for 10 h. The mixture is allowed to cool to Rt, and is then diluted with EtOAc (150 mL), washed with brine (3×), dried with MgSO₄ and concentrated to provide A22c.

Step 4:

Intermediate A22c (441 mg, 0.89 mmol) is dissolved into anhydrous MeCN (8 mL) before being treated with A1b (197 mg, 1.33 mmol) and DIPEA (0.31 mL, 1.8 mmol) (Aldrich). The resulting mixture is stirred for 1 h at RT, and then diluted with EtOAc, washed with 1N NaOH, water then brine, dried with MgSO₄ and concentrated to provide crude material that is purified by Combiflash (80:20 to 100:0, EtOAc/hexanes) to provide A22d.

Step 5:

Intermediate A22d (145 mg, 0.24 mmol) is dissolved into anhydrous THF (2 mL) at RT before being treated with MeMgBr (0.51 mL, 0.72 mmol) (1.4M in THF/toluene (1:3), Aldrich). The resulting mixture is stirred for 30 min, and then an aqueous solution of saturated NH₄Cl (2 mL) is added. This mixture is stirred for 30 min and then water is added. The mixture is extracted with EtOAc (3×) and the layers are separated. The organic layer is washed with water, brine, dried with MgSO₄ and concentrated to provide crude material that is purified by preparative HPLC to afford compound 1118.

Step 6:

Compound 1118 (90 mg, 0.14 mmol) is dissolved into anhydrous DCM (3 mL) and cooled to 0° C. A solution of BBr₃ (0.43 mL, 0.43 mmol, 1M in DCM) (Aldrich) is added. The resulting mixture is stirred at RT for 1 h, and then water is added. The mixture is made basic using 5N NaOH, and then extracted with EtOAc. The layers are separated and organic layer is washed with water, brine, dried with MgSO₄ and concentrated to provide crude material that is purified by preparative HPLC to provide compound 1119.

Example A23

Preparation of Compounds 1115, 1113 and 1111

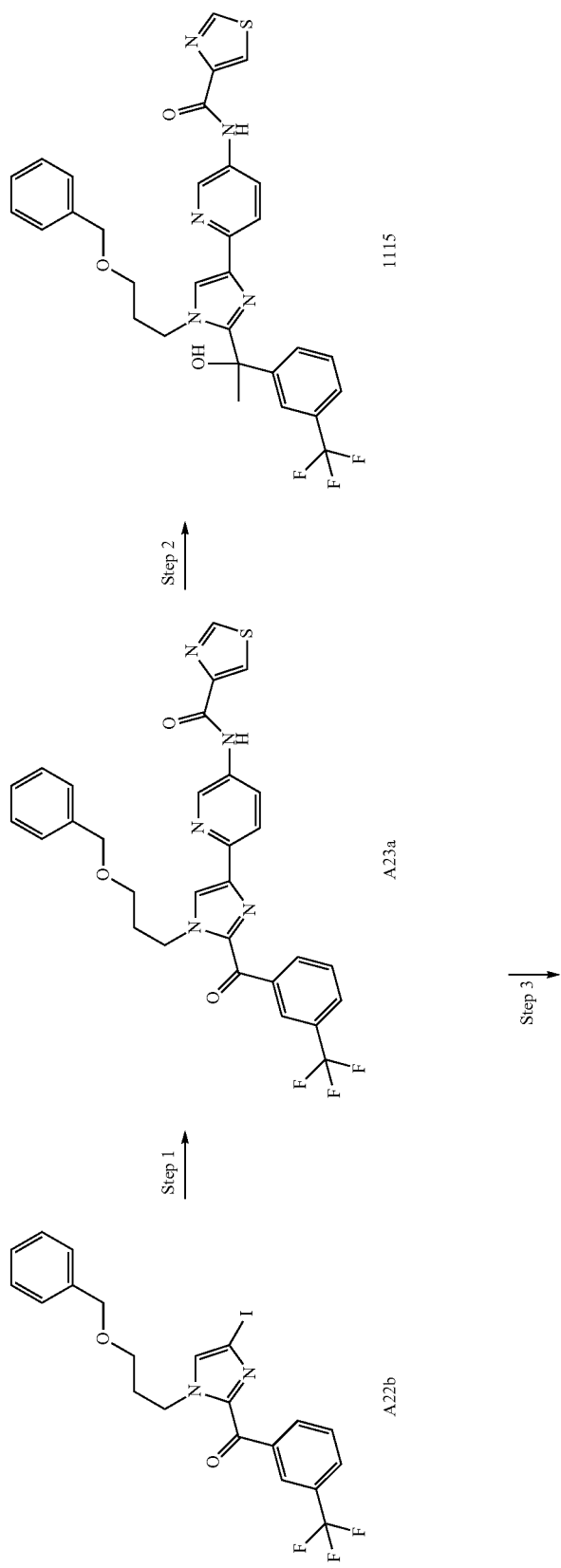

-continued
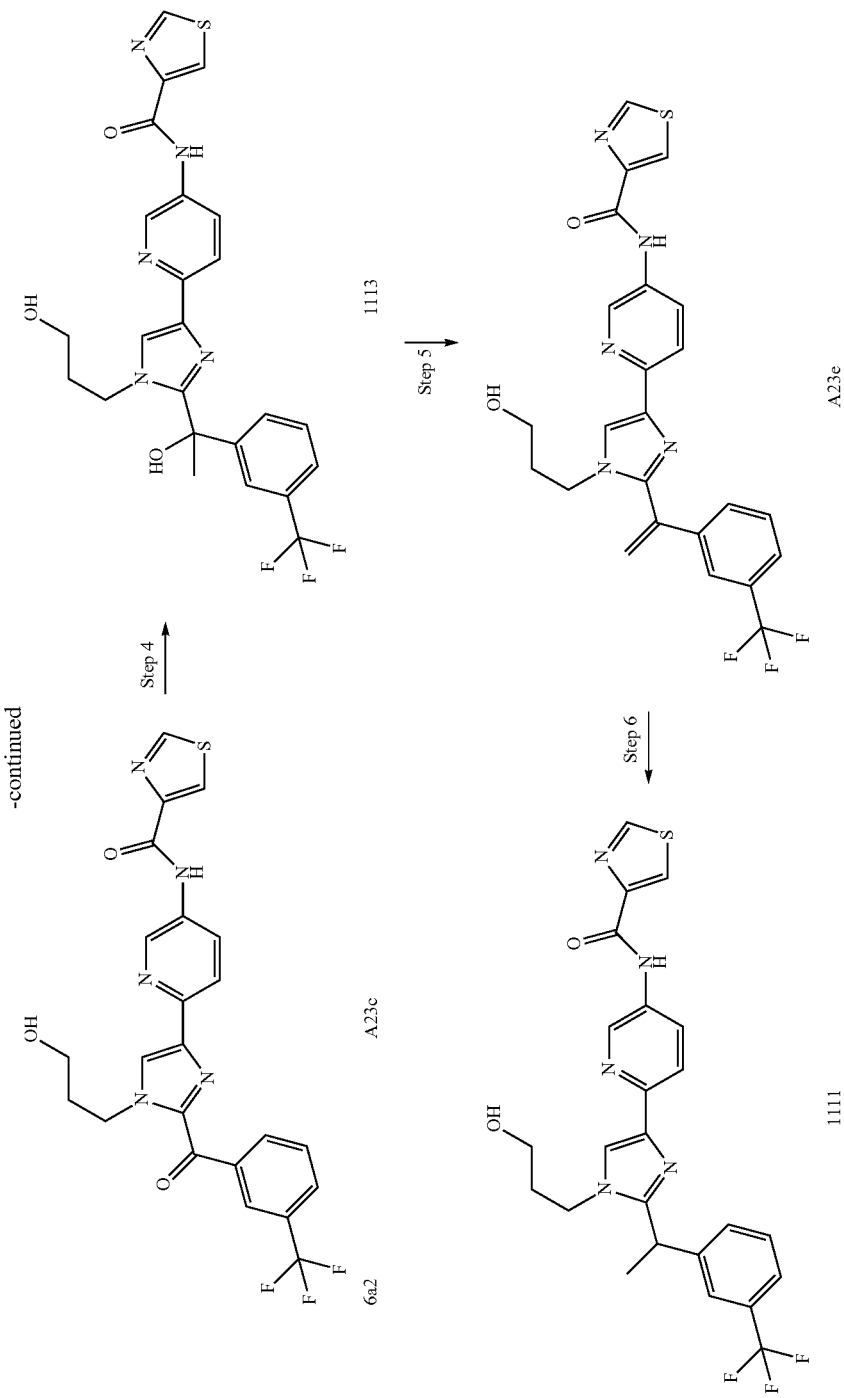

Step 1:

Intermediate A22b (700 mg, 1.4 mmol) is dissolved in anhydrous dioxane (10 mL) and treated with $PdCl_2(PPh_3)_2$ (96 mg, 0.14 mmol) (Aldrich) and hexadimethyltin (0.56 mL, 2.7 mmol) (Aldrich). The resulting mixture is heated to 90° C. for 4 h, and is then allowed to cool to RT before being treated with A11b (541 mg, 1.9 mmol) and $Pd[(PPh_3)]_4$ (236 mg, 0.20 mmol) (Strem Chemicals). The resulting mixture is heated to 110° C. for 6 h, and is then allowed to cool to RT. Water (5 mL) is added and the mixture is extracted with EtOAc (3×). The layers are separated and the organic layer is washed with brine, dried with $MgSO_4$ and concentrated to provide crude material that is purified by Combiflash (30:70 to 100:0, EtOAc/hexanes then 5% MeOH/DCM) to provide A23a.

Step 2:

Intermediate A23a (275 mg, 0.47 mmol) is dissolved into anhydrous THF (4 mL) at RT before being treated with MeMgBr (1.3 mL, 1.9 mmol) (1.4M in THF/toluene (1:3), Aldrich). The resulting mixture is stirred for 30 min and then an aqueous solution of saturated $NH_4Cl$ (2 mL) is added. This mixture is stirred for 30 min and then water is added. The mixture is extracted with EtOAc (3×) and the layers are separated. The organic layer is washed with water, brine, dried with $MgSO_4$ and concentrated to provide crude material that is purified by preparative HPLC to provide compound 1115.

Step 3:

Intermediate A23a (275 mg, 0.47 mmol) is dissolved into anhydrous DCM (4 mL) and cooled to 0° C. A solution of $BBr_3$ (1.5 mL, 1.5 mmol, 1M in DCM) (Aldrich) is added and the resulting mixture is stirred at RT for 1 h. Water is added. The mixture is made basic using 5N NaOH and then extracted with EtOAc. The layers are separated and organic layer is washed with water, brine, dried with $MgSO_4$ and concentrated to provide A23c.

Step 4:

Intermediate A23c (235 mg, 0.47 mmol) is dissolved into anhydrous THF (4 mL) at RT before being treated with MeMgBr (1.0 mL, 1.4 mmol) (1.4M in THF/toluene (1:3), Aldrich). The resulting mixture is stirred for 1 h, and then an aqueous solution of saturated $NH_4Cl$ (2 mL) is added. The mixture is stirred for 30 min and then water is added. The mixture is extracted with EtOAc (3×) and the layers are separated. The organic layer is washed with water, brine, dried with $MgSO_4$ and concentrated to provide crude material that is purified by preparative HPLC to provide compound 1113.

Step 5:

Compound 1113 (280 mg, 0.47 mmol) is dissolved into TFA (6 mL) at RT. The resulting solution is heated to 80° C. for overnight, allowed to cool and concentrated to afford A23e.

Step 6:

Intermediate A23e (270 mg, 0.54 mmol) is suspended into iPrOH (15 mL) at RT and then treated with ammonium formate (511 mg, 8.1 mmol) (Acros) followed by 5% Pd/C (500 mg) (Aldrich). The resulting mixture is stirred at 80° C. overnight, allowed to cool to RT and then filtered using an Acrodisc filter. The mixture is concentrated and purified by preparative RP-HPLC to provide compound 1111.

Example A24

Preparation of Compounds 1109 and 1041

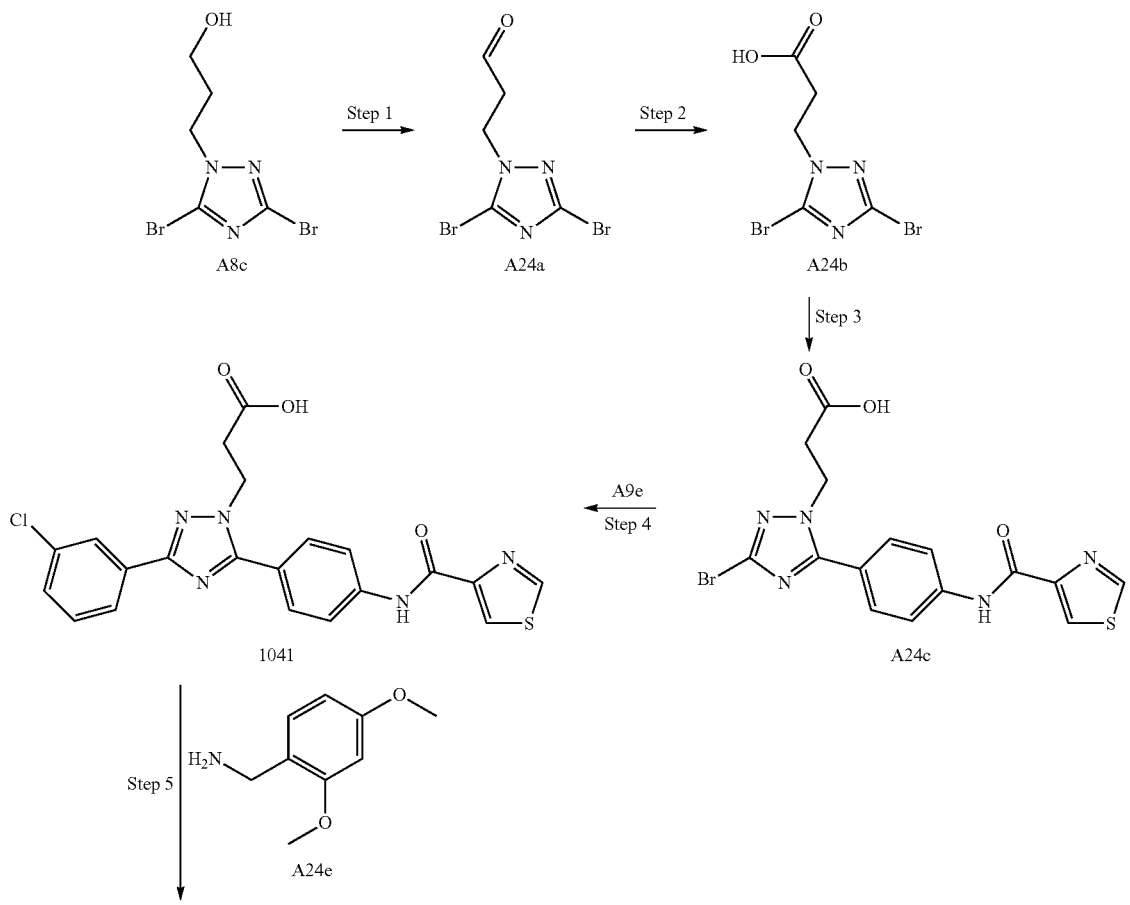

-continued

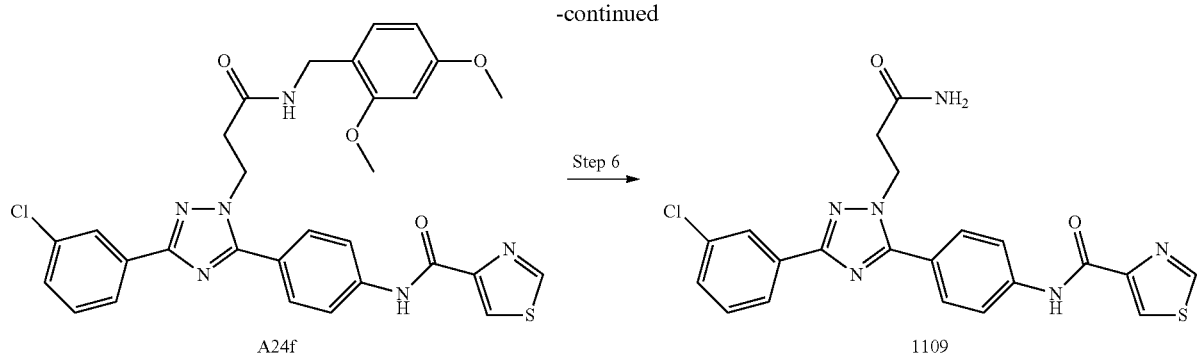

A24f

1109

Step 1:
Intermediate A8c (1.5 g, 5.3 mmol) is dissolved in DMF (30 mL) and Dess-Martin periodinane (3.3 g, 7.9 mmol) is added. The reaction mixture is stirred overnight and quenched with 10% aqueous sodium thiosulfate (15 mL) and saturated sodium bicarbonate (15 mL). The heterogeneous solution is stirred for 30 min, and then the aqueous layer is extracted with EtOAc (2×60 mL). The organic layers are combined, washed with brine, dried over MgSO$_4$, filtered and concentrated under reduced pressure to give crude intermediate A24a.

Step 2:
To a solution of intermediate A24a (1.4g, 4.9 mmol) in dioxane (60 mL) is added a solution of NaH$_2$PO$_4$ (2.7 g, 19.8 mmol) in water (15 mL) and NH$_2$SO$_3$H (720.7 mg, 7.4 mmol). The mixture is then cooled to 0° C. and a solution of NaClO$_2$ (581.8 mg, 6.4 mmol) in water (15 mL) is added. The mixture is stirred at 0° C. for 15 min. Na$_2$SO$_3$ (748.4 mg, 5.9 mmol) is added and the resulting mixture is stirred at 0° C. for 1 h, acidified with 1N HCl (75 mL) and extracted with EtOAc (2×100 mL). The organic layers are combined, washed with brine, dried over MgSO$_4$, filtered and concentrated to afford intermediate A24b which is used without further purification.

Step 3:
Intermediates A24b (200.0 mg, 0.67 mmol) and A4b (265.1 mg, 0.80 mmol), potassium carbonate (184.9 mg, 1.3 mmol), dioxane (6 mL) and water (2 mL) are charged in a microwave vial. The reaction mixture is degassed with argon for 5 min and Pd(PPh$_3$)$_4$ (77.3 mg, 0.067 mmol) is added. The vial is capped and heated in microwave at 120° C. for 20 min. After cooling at RT, the reaction mixture is quenched with 1N HCl (20 mL) and extracted with EtOAc (2×30 mL). The organic layers are combined, dried over MgSO$_4$, filtered and concentrated to provide A24c.

Step 4:
Intermediate A24c (70.0 mg, 0.17 mmol), 3-chlorophenylboronic acid A9e (31.1 mg, 0.20 mmol, Frontier Scientific), potassium carbonate (15.8 mg, 0.33 mmol), dioxane (3 mL) and water (1 mL) are charged in a microwave vial. The reaction mixture is degassed with argon for 5 min and Pd(PPh$_3$)$_4$ (19.2 mg, 0.017 mmol) is added. The vial is capped and heated in a microwave at 120° C. for 20 min. After cooling to RT, the reaction mixture is quenched with 1N HCl (10 mL) and extracted with EtOAc (2×15 mL). The organic layers are combined, dried over MgSO$_4$, filtered and concentrated to dryness. The product is purified by preparative HPLC to give compound 1041.

Step 5:
A solution of compound 1041 (75.3 mg, 0.17 mmol) in DMF (1 mL) is treated with A24e (32.4 µL, 0.22 mmol, Aldrich), DIPEA (72.2 µL, 0.42 mmol) and HATU (88.3 mg, 0.23 mmol). The reaction mixture is stirred for 1 h, and then partitioned between water (15 mL) and EtOAc (25 mL). The layers are separated. The organic layer is washed with brine (3×), dried over MgSO$_4$ and concentrated to provide A24f that is used without further purification.

Step 6:
Crude intermediate A24f (100.0 mg, 0.17 mmol) is dissolved in a mixture of DCM (2.5 mL) and TFA (2.5 mL). The reaction mixture is stirred at RT overnight. The solvents are removed in vacuo to give the crude product which is purified by preparative HPLC. The pure fractions are pooled, frozen and lyophilized to afford compound 1109.

Example A25

Preparation of Compound 1117

A6c + A12b + A9e  →Step 1→

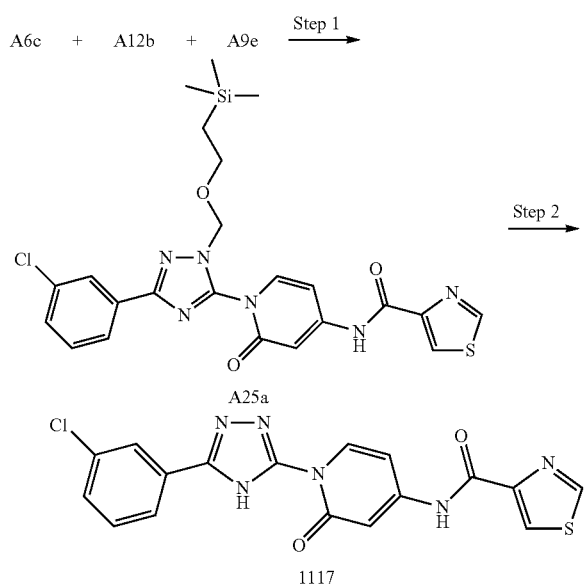

Step 1:
Intermediates A6c (50.0 mg, 0.14 mmol), A12b (31.0 mg, 0.14 mmol), potassium carbonate (38.7 mg, 0.28 mmol) and DMF (1 mL) are charged in a microwave vial which is capped and heated in microwave at 160° C. for 30 min. To the reaction mixture cooled to RT, water (0.5 mL), potassium carbonate (19.4 mg, 0.14 mmol), A9e (26.3 mg, 0.17 mmol, Matrix) and Pd(PPh$_3$)$_4$ (16.2 mg, 0.014 mmol) are added. The vial is capped and heated in a microwave at 120° C. for 20 min. The resulting mixture is partitioned between water (10 mL) and EtOAc (25 mL). The layers are separated and the organic layer is washed with brine, dried over MgSO$_4$ and filtered. The filtrate is concentrated under reduced pressure to afford A25a which is used as such.

Step 2:

Crude intermediate A25a (74.1 mg, 0.14 mmol) is dissolved in a mixture of DCM (2 mL) and TFA (2 mL). The reaction mixture is stirred at RT overnight. After completion, the solvents are removed in vacuo to give the crude product which is purified by preparative HPLC. The pure fractions are pooled, frozen and lyophilized to afford compound 1117.

Example A26

Preparation of Compound 1077

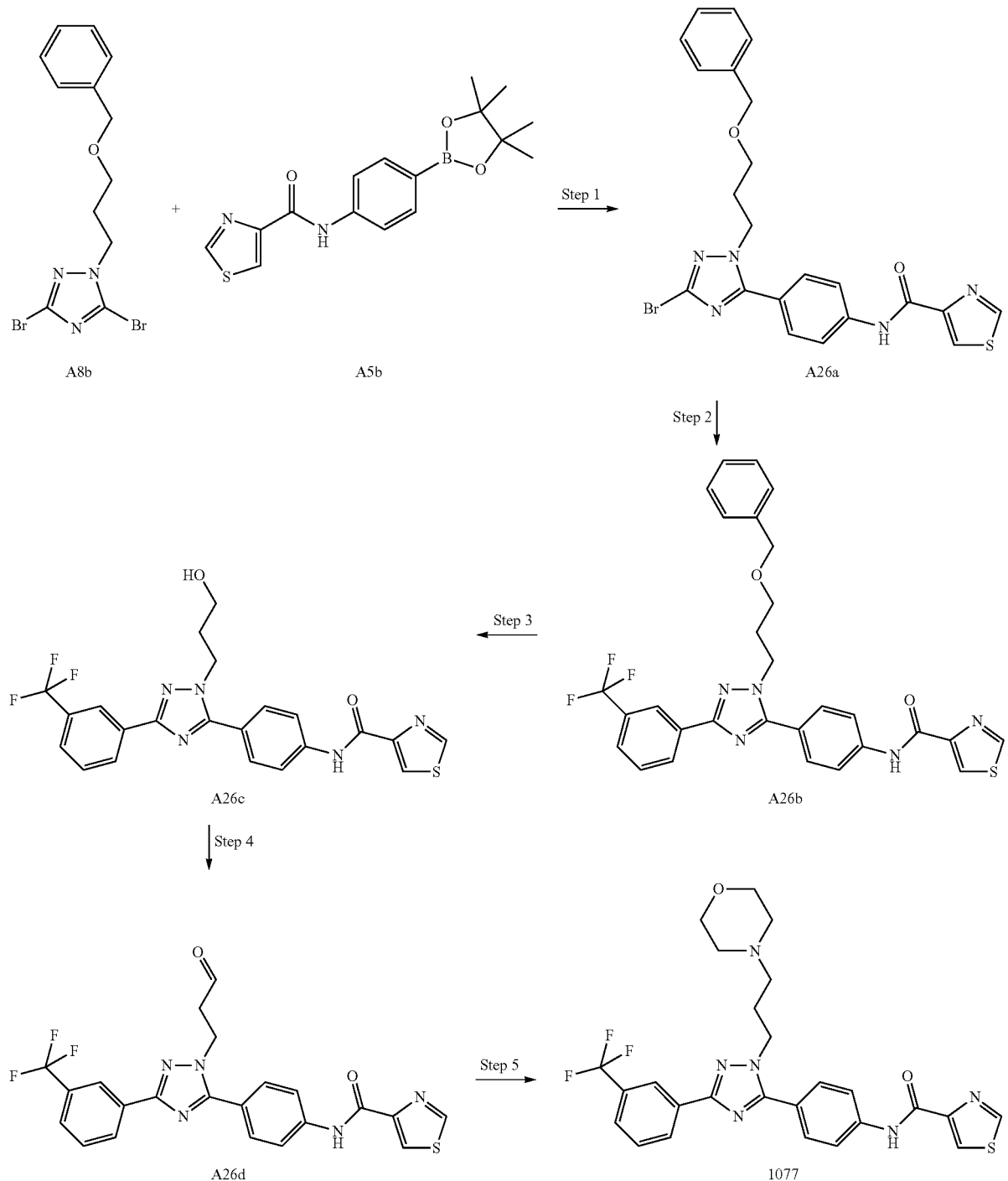

Step 1:

Intermediates A8b (165.3 mg, 0.44 mmol) and A5b (174.6 mg, 0.53 mmol), potassium carbonate (121.8 mg, 0.88 mmol), dioxane (1.5 mL) and water (0.5 mL) are charged in a microwave vial. The reaction mixture is degassed with argon for 5 min and Pd(PPh$_3$)$_4$ (50.9 mg, 0.044 mmol) is added. The vial is capped and heated in a microwave at 120° C. for 20 min. After cooling to RT, the reaction mixture is partitioned between water (15 mL) and EtOAc (35 mL). The organic layers are combined, washed with brine, dried over MgSO$_4$, filtered and concentrated. The crude residue is purified by CombiFlash (0% to 100% EtOAc/hexanes) to provide intermediate A26a.

Step 2:

Intermediate A26a (140.2 mg, 0.28 mmol), A8e (64.1 mg, 0.34 mmol, Frontier Scientific), potassium carbonate (77.8 mg, 0.56 mmol), dioxane (3.6 mL) and water (1.2 mL) are charged in a microwave vial. The reaction mixture is degassed with argon for 5 min and Pd(PPh$_3$)$_4$ (32.5 mg, 0.028 mmol) is added. The vial is capped and heated in microwave at 120° C. for 20 min. After cooling at RT, the reaction mixture is diluted with water (25 mL) and extracted with EtOAc (2×45 mL). The organic layers are combined, washed with brine, dried over MgSO$_4$, filtered and concentrated. The crude residue is purified by preparative HPLC. Pure fractions are pooled, frozen and lyophilized to afford compound A26b.

Step 3:

A solution of compound A26b (108.0 mg, 0.19 mmol) in DCM (10 mL) cooled at 0° C. is treated with boron tribromide (1 M in DCM, 632.4 µL, 0.63 mmol). The reaction mixture is stirred at RT for 3 days, and then partitioned between water (150 mL) and EtOAc (200 mL). The layers are separated and the organic layer is dried over MgSO$_4$, filtered and concentrated under reduced pressure to obtain crude intermediate A26c which is used without further purification.

Step 4:

Intermediate A26c (90.7 mg, 0.19 mmol) is dissolved in DCM (5 mL) at RT and Dess-Martin periodinane (121.9 mg, 0.29 mmol) is added. The reaction mixture is stirred overnight and quenched with 10% aqueous sodium thiosulfate (20 mL) and saturated sodium bicarbonate (30 mL). The heterogeneous solution is stirred for 30 min, and then the aqueous layer is extracted with EtOAc (75 mL). The organic layers are combined, dried over MgSO$_4$, filtered and concentrated under reduced pressure to give crude intermediate A26d.

Step 5:

A solution of intermediate A26d (45.0 mg, 0.095 mmol), glacial acetic acid (180.3 µL, 3.15 mmol) and morpholine (82.6 µL, 0.95 mmol, Aldrich) in DMF (6 mL) is stirred at RT for 45 min, and then triacetoxyborohydride (161.8 mg, 0.76 mmol) is added and the resulting mixture is stirred overnight. After completion, the mixture is partitioned between saturated sodium bicarbonate (20 mL) and EtOAc (50 mL). The layers are separated and the organic layer is dried over MgSO$_4$, filtered and concentrated to give crude product which is purified by preparative HPLC. Pure fractions are pooled, frozen and lyophilized to afford compound 1077.

Example A27

Preparation of Compounds 1004 and 1132

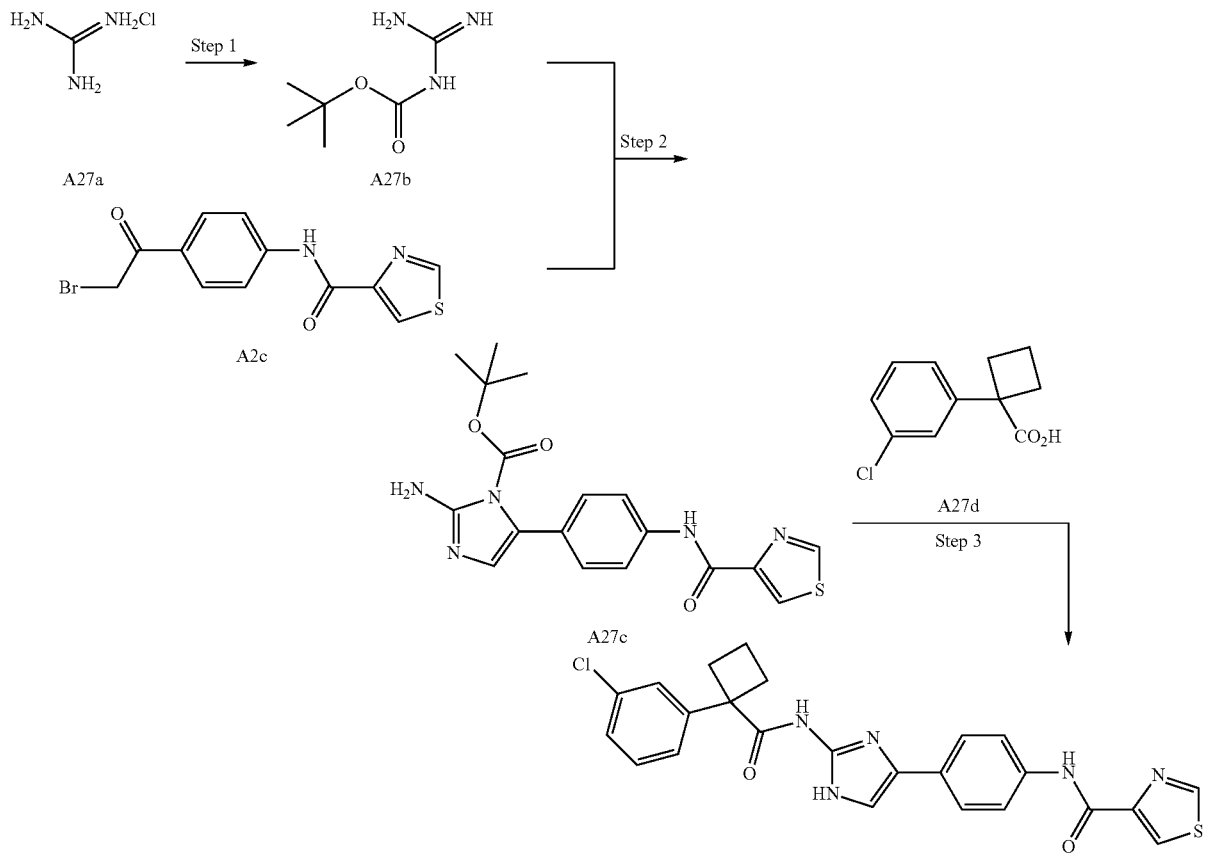

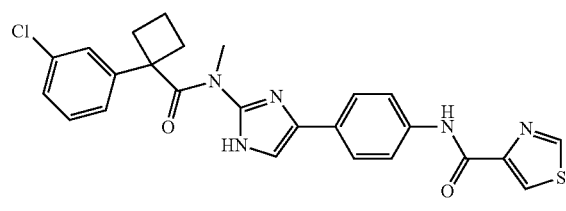

1132

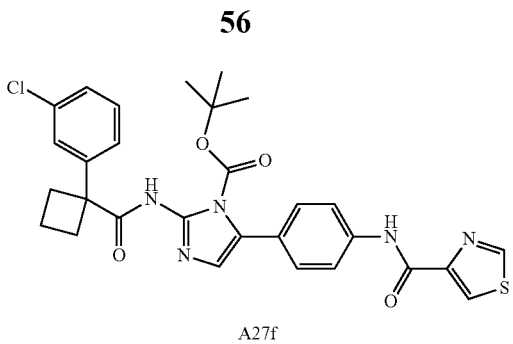

A27f

Step 1:
A solution of NaOH (7.3 g, 180 mmol) in water (18 mL) is cooled to 0° C. and A27a (Aldrich, 8.8 g, 92 mmol) is added. The solution is stirred for 10 min and then a solution of Boc$_2$O (5.0 g, 23 mmol) in acetone (17 mL) is added. The reaction mixture is stirred for 2.5 h and then concentrated to about one half volume. The solution is extracted with EtOAc and the organic layer is dried over MgSO$_4$ and concentrated to give A27b.

Step 2:
Carbamate A27b (1.5 g, 9.2 mmol) and bromoketone A2c (1.0 g, 3.1 mmol) are dissolved in DMF (22 mL) and the reaction is stirred overnight. The reaction is diluted with EtOAc and the mixture washed with water. The organic layer is dried over MgSO$_4$ and concentrated to dryness. The product is purified by Combiflash to give A27c.

Step 3:
A solution of HATU (384 mg, 1.0 mmol), A27d (Apollo, 200 mg, 0.93 mmol) and A27c (300 mg, 0.78 mmol) in DMF (5 mL) is treated with DIPEA (0.34 mL) at RT. The reaction mixture is stirred overnight and then is diluted with water and EtOAc. The organic layer is washed with saturated NaHCO$_3$ and saturated NH$_4$Cl, dried over MgSO$_4$ and evaporated. The residue is purified by Combiflash to provide compound 1004 and A27f.

Step 4:
A solution of A27f (36 mg, 0.062 mmol) in DMF (1 mL) is treated with a solution of MeI (10 μL, 0.1 mmol) in DMF (0.1 mL). The reaction mixture is stirred at RT overnight and then diluted with EtOAc and washed with saturated NaHCO$_3$. The organic layer is dried over MgSO$_4$ and concentrated to dryness. The residue is suspended in 4M HCl in dioxane (0.3 mL, 1.2 mmol) and the mixture is stirred overnight. The mixture is evaporated to dryness, and then is dissolved in water (0.2 mL) and MeOH (1.8 mL). The solution is filtered through an Acrodisc and is purified by preparative HPLC to give compound 1132.

Example A28

Preparation of Compound 1039

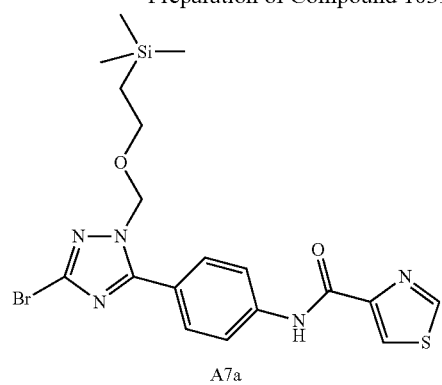

A7a

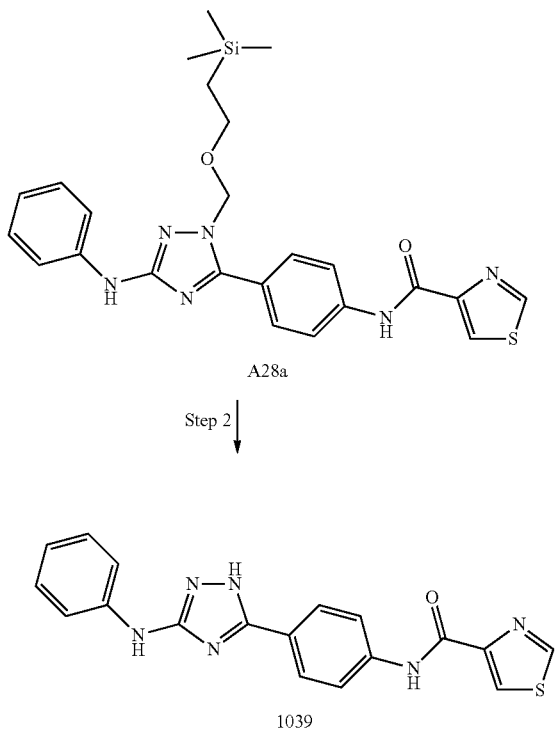

Step 1:
Intermediate A7a (25 mg, 0.052 mmol), aniline (7.1 μL, 0.078 mmol, Aldrich), Xantphos (3.0 mg, 0.005 mmol), sodium phenoxide (9.0 mg, 0.078 mmol), Pd$_2$(dba)$_3$ (4.8 mg, 0.005 mmol) and dioxane (1 mL) are charged in a microwave vial. The vial is capped and heated in microwave at 150° C. for 2 h. After cooling at RT, the reaction mixture is diluted with EtOAc (15 mL). The organic layer is washed with water, aqueous saturated solution of NH$_4$Cl and brine, dried over MgSO$_4$, filtered and concentrated under reduced pressure to give crude intermediate A28a.

Step 2:
Compound 1039 is made from A28a by analogy to compound 1070 from A7b, following step 3 from Example A7.

Example A29

Preparation of Compound 1089

A10a → Step 1 → A29a → Step 2

Step 1:

Compound A29a is made from A10a by analogy to compound A10b from A10a, following step 1 from Example A10.

Step 2:

Compound 1089 is made from A29a by analogy to compound A10e from A10c, following steps 3 and 4 from Example A10.

Example A30

Preparation of Compound 1133

A4a + A30a → Step 1 → A30b → Step 2 → A30c → Step 3 → 1133

1089

Step 1:

Compound A30b is prepared from compounds A4a and A30a (Maybridge) by analogy to the preparation of compound A5b in example A5.

Step 2:

Compound A30c is prepared from compound A30b by analogy to the preparation of compound A7a in example A7.

Step 3:

Compound 1133 is prepared from 3-chlorophenylboronic acid (Frontier) and A30c by analogy to the preparation of compound 1070 in example A7.

Example A31

Preparation of Compound 1143

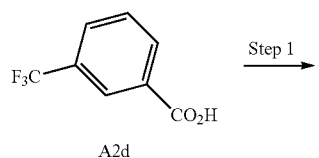

Step 1:
Compound A31a is prepared from compound A2d (Alfa Aesar) by analogy to the preparation of compound A3e in example A3.

Step 2:
Compound 1143 is prepared from compounds A31b (Aldrich) and A31a by analogy to the preparation of compound 1016 in example A3.

Example A32

Preparation of Compound 1139

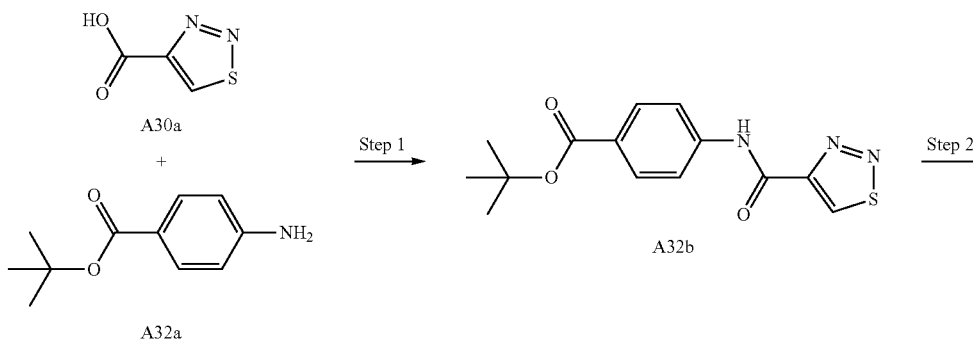

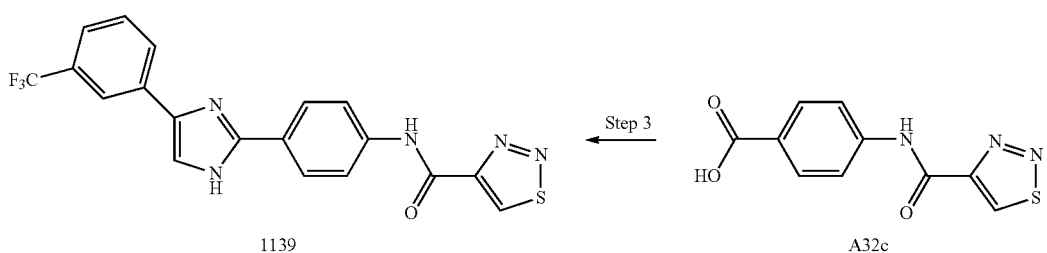

-continued

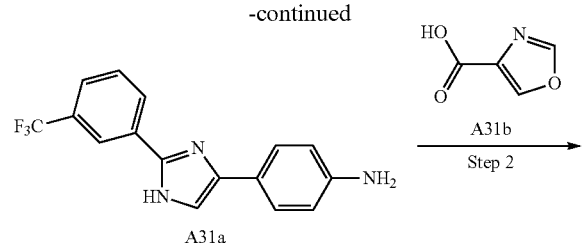

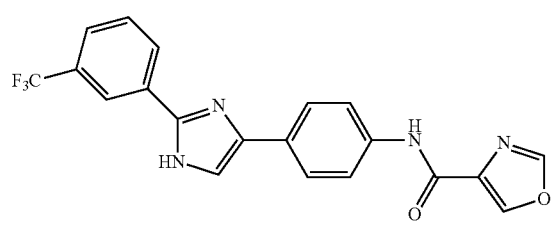

Step 1:
Compound A32b is prepared from compounds A30a (Maybridge) and A32a (Fluka) by analogy to the preparation of compound A15b in example A15.

Step 2:
Compound A32b (0.90 g, 2.9 mmol) is dissolved in DCM (3 mL) and TFA (3 mL) is added. The reaction mixture is stirred for 15 min, evaporated to dryness and the residue is partitioned between EtOAc and 10% HCl. The organic layer is dried over $MgSO_4$ and concentrated to dryness to give A32c.

Step 3:
Compound 1139 is made from A32c by analogy to compound 1059, following steps 2-5 from Example A14.

Example A33

Preparation of Compound 1038

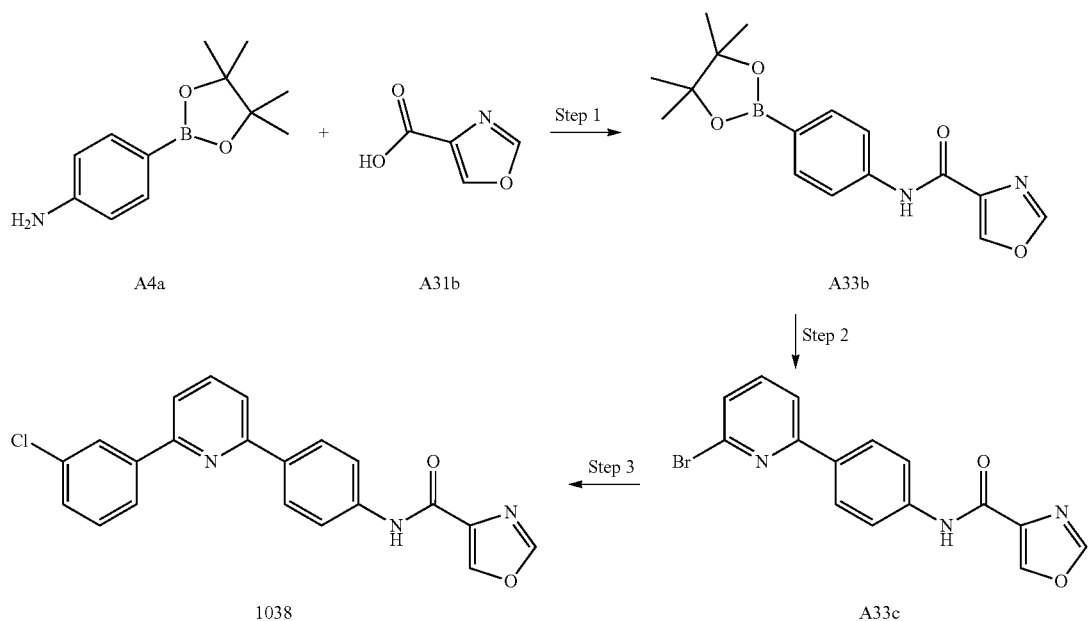

Step 1:

Compound A33b is prepared from compounds A4a and A31b (Aldrich) by analogy to the preparation of compound A5b in example A5.

Step 2:

Compound A33c is prepared from 2,6-dibromopyridine (Aldrich) and compound A33b by analogy to the preparation of compound A7a in example A7.

Step 3:

Compound 1038 is prepared from 3-chlorophenylboronic acid (Frontier) and A33c by analogy to the preparation of compound A7b in example A7.

Example A

HCMV AD169 CPE Assay

This assay format is a CPE (Cytopathic effect)-based assay that determines the ability of compounds to protect cells against infection with a dye reduction assay (MTS of CellTiter 96® AQueous Non-Radioactive Cell Proliferation Assay from Promega). The conversion of MTS into aqueous, soluble formazan is performed by dehydrogenase enzymes found in metabolically active cells. The quantity of formazan product determined by absorbance at 490 nm is directly proportional to the number of living cells in culture.

Reagents and Material:

| Product | Company | Catalog # | Storage |
| --- | --- | --- | --- |
| MRC-5 cells (Normal human lung fibroblast) | ATCC | CCL-171 | −80° C. |
| HCMV AD169 virus | ATCC | VR-538 | −80° C. |
| D-MEM cell culture medium | Invitrogen | 11995 | 4° C. |
| Dulbecco's PBS | Invitrogen | 14190-136 | RT |
| Fetal Bovine Serum | HyClone | SH30396-03 | 4° C. |
| Penicillin/Streptomycin 100X | Invitrogen | 15140 | 4° C. |
| Trypsin-EDTA | Invitrogen | 25300-054 | 4° C. |
| DMSO | VWR (EMD Chemicals) | CAMX1457-6 | RT |
| Clear 384-well assay plates | Greiner | 781182 | RT |
| TopSeal-Adhesive sealing film | PerkinElmer | 6005185 | RT |
| PMS (Phenazine methosulfate) | Sigma | P9625 | −20° C. |
| MTS (3-(4,5-dimethylthiazol-2-yl)-5-(3-carboxymethoxyphenyl)-2-(4-sulfophenyl)-2H-tetrazolium, inner salt) | Promega | G1111 | −20° C. |

Preparation of Compounds:

Serial dilutions of the DMSO stock compound solution are performed using DMSO in columns 2-11 and 14-23. DMSO alone is present in columns 1, 12, 13 and 24. Four µL of the DMSO serial dilutions is obtained and diluted using 964 of D-MEM 5% FBS culture medium to obtain 4% DMSO (7×).

CPE Assay:

To perform the assay, 104 of the freshly prepared 4% DMSO serial dilution plate is added to the assay plate containing 40 µL of MRC-5 cells plated the day before (10000 cells per well). Twenty µL of diluted virus is added to columns 2-12 and 14-24 and only D-MEM 5% FBS medium to uninfected control (columns 1 and 13) for a final DMSO concentration of 0.6%.

The virus dilution is based on the amount of virus required to obtain a Signal-to-Background of 3-4 (generally between 0.1 and 1 µL of virus stock per well or MOI=0.05). The assay plates are incubated at 37° C. with 5% $CO_2$ for 9 days in order to obtain 100% CPE in infected control without compound (columns 12 and 24). Ten µL of freshly mixed room temperature MTS/PMS (1:20 v/v) is added and the plates are incubated at 37° C. with 5% $CO_2$ for 4-5 h (until signal saturation at 2.3 in the 100% CPE control). The plates are sealed with TopSeal for biosafety and read on the Envision plate reader (Perkin-Elmer) or equivalent at OD 492 nm.

Example B

HCMV AD169-Bac Luciferase Assay

This assay format is a luciferase reporter-based assay that determines the ability of compounds to inhibit the infection by detecting a luciferase signal decrease following the addition of BIGlo substrate (preparation indicated below) directly in the culture media. Mono-oxygenation of luciferin is catalyzed by luciferase in the presence of $Mg_{2+}$, ATP and molecular oxygen. The generation of oxyluciferin is a luminescent reaction that can be detected with the proper platereader. Human Cytomegalovirus AD169-Bac is obtained from Dr. Thomas Shenk at Princeton University (reference paper Yu et al. 2002—J. Virol. 76 (5):2316-2328, herein incorpoarated by reference) and modified by recombineering to introduce a humanized firefly luciferase gene (Luc2) at the US2-US6 position in the HCMV genome. The virus is expanded in MRC-5 cells.

Reagents and Material:

| Product | Company | Catalog # | Storage |
| --- | --- | --- | --- |
| MRC-5 cells (Normal human lung fibroblast) | ATCC | CCL-171 | −80° C. |
| HCMV AD169-Bac-Luc2 US2-US6 clone #26 virus | Homemade | | −80° C. |
| D-MEM cell culture medium | Invitrogen | 11995 | 4° C. |
| Dulbecco's PBS | Invitrogen | 14190-136 | RT |
| Fetal Bovine Serum | HyClone | SH30396-03 | 4° C. |
| Penicillin/Streptomycin 100X | Invitrogen | 15140 | 4° C. |
| Trypsin-EDTA | Invitrogen | 25300-054 | 4° C. |
| DMSO | VWR (EMD Chemicals) | CAMX1457-6 | RT |
| Black clear bottom 384-well assay plates | Greiner | 781091 | RT |
| TopSeal-Adhesive sealing film | Perkin Elmer | 6005185 | RT |
| Backing tape white | Perkin Elmer | 6005199 | RT |

For BIGlo Luciferase Buffer:

| Product | Company | Catalog # | Storage |
| --- | --- | --- | --- |
| Tricine | Sigma | T0377-250G | RT |
| EDTA 0.5M | Gibco-BRL | 15575-038 | RT |
| NaTPP (Na Triphosphate) | Sigma | T5633-1G | RT |
| MgSO4 | Sigma | M5921-500G | RT |
| ATP | Sigma | A2383-25G | −20° C. |
| Beta-mercaptoethanol | Sigma | M6250-500 ml | RT |
| D-Luciferin Potassium salt | GOLD BioTechnology | LUCK-500 or 1G | −20° C. |
| Triton X-100 | Sigma | T9285 | RT |

Final Concentrations:

| | |
| --- | --- |
| Tricine | 25 mM |
| EDTA | 0.5 mM |
| NaTPP (Na Triphosphate) | 0.54 mM |
| MgSO4 | 16.3 mM |
| **ATP | 1.2 mM |
| **Beta-mercapto. | 56.8 mM |
| **Luciferin | 0.05 mM |
| Triton X-100 | 0.10% |
| pH 7.8 (adjusted with NaOH 10N) | |

**add only after pH adjustment
Stored at −80° C.

Preparation of Compounds:

Serial dilutions of the DMSO stock compound solution are performed using DMSO in columns 2-11 and 14-23. DMSO alone is present in columns 1, 12, 13 and 24. Four µL of the DMSO serial dilutions is obtained and diluted using 964 of D-MEM 5% FBS culture medium to obtain 4% DMSO (7×).

AD169 Luciferase Assay:

To perform the assay, 7 µL of the freshly prepared 4% DMSO serial dilution plate is added to the assay plate containing 254 of MRC-5 cells plated the day before (10000 cells per well). Seventeen µL of diluted virus is added to columns 2-12 and 14-24 and only D-MEM 5% FBS medium to uninfected control (columns 1 and 13) for a final DMSO concentration of 0.6%. The virus dilution is based on the amount of virus required to obtain the highest luciferase signal possible without CPE (generally between 0.05 and 1 µL of virus stock per well or MOI=0.02). The assay plates are incubated at 37° C. with 5% $CO_2$ for 3 days. Fifteen µL of room temperature BIGlo buffer is added to room temperature assay plates also incubated at room temperature for 15 minutes. The plates are sealed with TopSeal for biosafety and the luminescence signal is read on the TopCount plate reader (Perkin-Elmer) or equivalent.

Example C

HCMV AD169 qPCR 96-Well Assay

The hCMV quantitative PCR (qPCR) assay evaluates the ability of a compound to inhibit, directly or indirectly, the replication of hCMV viral DNA during the first 72 h following the infection. Compounds that inhibit either entry or the hCMV polymerase are active in this assay. Compounds are tested in the qPCR assay in 96-well plates, using a 9-point dose-response with 8 compounds for each 96-well plate. The assay was adapted from the method described by Schnepf et al., Rapid determination of antiviral drug susceptibility of human cytomegalovirus by real-time PCR, Antiviral Research 81 (2009) 64-67.

Reagents and Material:

| Product | Company | Catalog # | Storage |
|---|---|---|---|
| MRC-5 cells (Normal human lung fibroblast) | ATCC | CCL-171 | −80° C. |
| HCMV AD169 virus | ATCC | VR-538 | −80° C. |
| D-MEM cell culture medium | Invitrogen | 11995 | 4° C. |
| Dulbecco's PBS | Invitrogen | 14190-136 | RT |
| Fetal Bovine Serum | HyClone | SH30396-03 | 4° C. |
| Trypsin-EDTA | Invitrogen | 25300-054 | 4° C. |
| Penicillin/Streptomycin | Invitrogen | 15140 | 4° C. |
| DMSO | VWR (EMD Chemicals) | CAMX1457-6 | RT |
| Proteinase K >600 mAU/ml | Qiagen | 19131 | RT |
| TaqMan Universal PCR Master mix | AppliedBiosystems | 4326708 | 4° C. |
| TaqMan Fast Advanced Master mix | AppliedBiosystems | 4444558 | 4° C. |
| 384-well clear reaction plate | AppliedBiosystems | 4309849 | RT |
| Optical adhesive covers | AppliedBiosystems | 4311971 | RT |
| Breathable seal | Corning | 80081-122 | RT |
| 384-well microplates | Greiner | 781280 | RT |
| 384-well tissue culture plates | Greiner | 781182 | RT |

For Cell Lysis Buffer:

| Product | Company | Catalog # | Storage |
|---|---|---|---|
| Tris | Gibco-BRL | 15506-017 | RT |
| KCl | Sigma | P9541 | RT |
| $MgCl_2$ | OmniPur | 5980 | RT |
| Tween20 | Sigma | P7949 | RT |
| Nonidet P40 | Sigma | I3021 | RT |

Final Concentrations:
10 mM Tris-HCl pH8.0
50 mM KCl
2 mM MgCl2
0.45% Tween20
0.45% Nonidet P40
Primers and Probes:

```
qHCMV7 = US17 Forward primer,
                               (SEQ ID NO: 1)
5' GAA GGT GCA GGT GCC CTG 3',
synthesis by IDT.

qHCMV8 = US17 Reverse primer,
                               (SEQ ID NO: 2),
5' GTG TCG ACG AAC GAC GTA CG 3'
synthesis by IDT.

qHCMV9 = US17 probe, FAM probe with ZEN internal
quencher and Iowa Black FQ quencher,
                               (SEQ ID NO: 3),
5'-FAM-ACG GTG CTG/ZEN/TAG ACC CGC ATA CAA A-
IABkFQ-3'
synthesis by IDT RP8LL = mitochodrial Forward primer,
                               (SEQ ID NO: 4),
5' ACC CAC TCC CTC TTA GCC AAT ATT 3'
synthesis by IDT RP9LL = mitochodrial Reverse primer,
                               (SEQ ID NO: 5),
5' GTA GGG CTA GGC CCA CCG 3'
synthesis by IDT RP11LL = mitochodrial probe with JOE probe with
Iowa Black FQ quencher,
                               (SEQ ID NO: 6),
5' JOE-CTA GTC TTT GCC GCC TGC GAA GCA-IABkFQ-3'
synthesis by IDT
```

Preparation of Compounds:

Serial dilutions of the DMSO stock compound solution are performed using DMSO in columns 2-10. DMSO alone is present in columns 1 and 11. Column 12 remains empty. Diluted compounds are further diluted with DMEM 5% FBS cell culture medium.

AD169 qPCR Assay:

To perform the assay, 25 μL of inhibitor dilutions freshly prepared is added to the assay plate containing 50 μL of MRC-5 cells plated the day before (30000 cells per well). In a 9 point dose-response, column 1 contains mock infected cells and serves at negative control, with the appropriate concentration of DMSO, columns 2 to 10 contain compound dilutions and column 11 contains infected cells, with the appropriate concentration of DMSO and serves as the positive control. Column 12 serves for the standard curve in the qPCR process. Twenty-five μL of virus diluted in DMEM 5% FBS medium (to infect at MOI=0.05) is added to columns 2-11 and only D-MEM 5% FBS medium to uninfected control (column 1) for a final DMSO concentration of 0.6%. Incubate plates at 37° C. in 5% $CO_2$ incubator for 3 days. Whole cell lysates are then obtained by adding 100 μL of Cell lysis buffer to each well including freshly added Proteinase K at a ratio of 1:5 (i.e. 200 μL Proteinase K:1000 μL Cell Lysis buffer) and incubating the assay plate at 56° C. for 1 h. Plates are centrifuged at 1300 rpm for 2 minutes to remove any condensation before proceeding with the qPCR.

The cell lysate is carefully pipetted up and down to mix well and diluted 1:40 in $H_2O$ to give a final dilution of 1:80 relative to the 100 μL of lysis buffer that Is added to the cells. 5 μL of diluted lysate is used for the qPCR reaction. An incubation of 5 minutes at 95° C. in a PCR machine is required to inactivate the Proteinase K. The cell lysates can be stored at −20° C. or used to perform qPCR immediately.

Preparation of Standard Curve:

A 81 bp fragment of US17 gene from AD169 is amplified by PCR using primers qHCMV7 and qHCMV8. The PCR product is cloned into pCR4 TOPO vector (Invitrogen) and a clone harboring the insert is selected. A mitochondrial DNA is also added to normalize the HCMV copy number. Serial dilutions of the US17 plasmid and mitochondrial DNA are performed in heat-inactivated lysis buffer at the same dilution as the cell lysates (1:80). Usually, a standard curve ranging from 10E6 to 10E2 copies (per well) is suitable.

A typical qPCR reaction consists of the following:

| Diluted whole cell lysate | 5 μL |
|---|---|
| TaqMan Universal PCR Master mix | 12.5 μL |
| qHCMV7 and qHCMV8 at 10 μM | 0.5 μL I |
| Probe qHCMV9 at 10 μM | 0.5 μL |
| RP8LL and RP9II at 10 μM | 0.25 μL |
| Probe RP11LL at 10 μM | 0.25 μL |
| Rox reference dye | 0.5 μL |
| H2O | 5.5 μL |
| | 25 μL final volume |

A qPCR cycle consists of an initial denaturation of DNA and activation of the Taq enzyme at 95° C. for 10 min followed by 45 cycles of 15 seconds at 95° C. and 1 min at 60° C. Fluorescence is measured at each cycle, following the elongation step at 60° C. The reaction, data acquisition and analysis are performed using AppliedBiosystems 7500 Real time PCR system or other suitable real-time PCR system.

All compounds of the invention are tested in at least one of the assays described in Examples A, B and C and show $EC_{50}$ values in the range of 6 μM or less. Representative data is shown below:

| Compound # | EC50 Example A | EC50 Example B | EC50 Example C |
|---|---|---|---|
| 1004 | 98 | 7 | |
| 1016 | 135 | 35 | |
| 1018 | 380 | 100 | 270 |
| 1034 | 275 | 59 | |
| 1038 | 3100 | 1190 | |
| 1039 | 550 | 103 | 390 |
| 1041 | 4100 | 645 | |
| 1045 | 345 | 66 | |
| 1052 | 4200 | 450 | 1800 |
| 1059 | | 425 | |
| 1070 | 510 | 93 | |
| 1077 | 903 | 180 | |
| 1086 | 355 | 118 | |
| 1087 | | 87 | |
| 1092 | | 203 | 620 |
| 1096 | | 665 | |
| 1097 | 280 | 60 | |
| 1098 | | 100 | |
| 1103 | | 1170 | 5800 |
| 1109 | | 185 | 455 |
| 1111 | | 1258 | 665 |
| 1113 | | 620 | 2100 |
| 1114 | | 150 | 596 |
| 1115 | | 535 | 1160 |
| 1116 | | 27 | 160 |
| 1117 | | 1450 | 3200 |
| 1118 | | 460 | 970 |
| 1119 | | 770 | 2050 |
| 1120 | | 92 | |
| 1121 | | 63 | 275 |
| 1129 | | | 145 |
| 1130 | | | 375 |
| 1132 | | 290 | |
| 1133 | 2050 | | |
| 1139 | 260 | 111 | |
| 1143 | 1225 | 245 | |

Tables of Compounds

The following tables list compounds representative of the invention. Retention times ($t_R$) for each compound are measured using the standard analytical HPLC or UPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions.

All of the compounds in Table 1 are synthesized analogously to the Examples described above.

For each compound in the tables, the analogous synthetic route to prepare each compound is identified by Example number. It will be apparent to a skilled person that the analogous synthetic routes may be used, with appropriate modifications, to prepare the compounds of the invention as described herein.

TABLE 1

| Cmpd # | Structure | Example # for synthesis | [M + H]+ | $t_R$ (min) |
|---|---|---|---|---|
| 1000 | (structure shown) | A2 | 577.1 | 1.33 |

TABLE 1-continued

| Cmpd # | Structure | Example # for synthesis | [M + H]+ | $t_R$ (min) |
|---|---|---|---|---|
| 1001 | 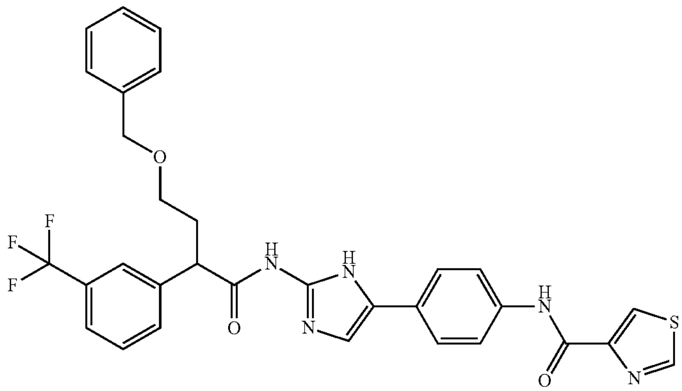 [SMILES: O=C(Nc1ccc(-c2cnc(NC(=O)C(CCOCc3ccccc3)c3cccc(C(F)(F)F)c3)[nH]2)cc1)c1cscn1] | A27 | 606 | 1.3 |
| 1002 | 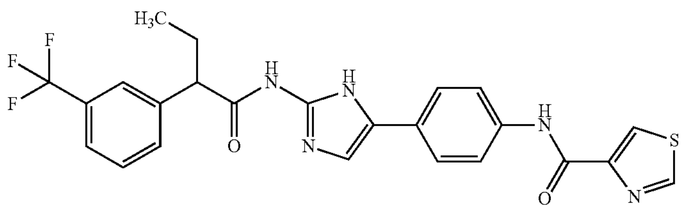 [SMILES: CCC(C(=O)Nc1ncc(-c2ccc(NC(=O)c3cscn3)cc2)[nH]1)c1cccc(C(F)(F)F)c1] | A27 | 500 | 1.15 |
| 1003 | 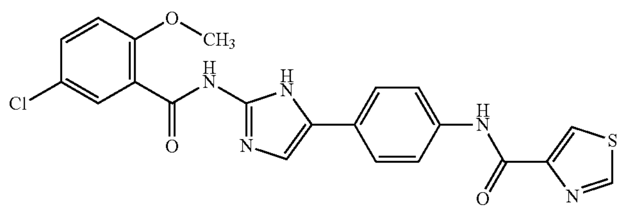 [SMILES: COc1ccc(Cl)cc1C(=O)Nc1ncc(-c2ccc(NC(=O)c3cscn3)cc2)[nH]1] | A27 | 454.0 455.9 | 0.98 |
| 1004 | 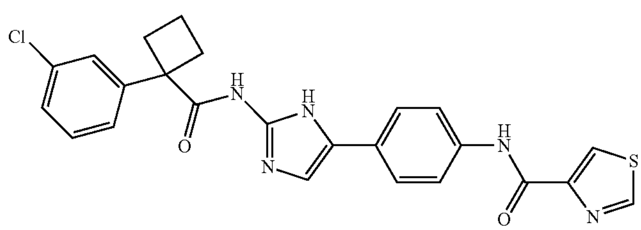 [SMILES: O=C(Nc1ccc(-c2cnc(NC(=O)C3(c4cccc(Cl)c4)CCC3)[nH]2)cc1)c1cscn1] | A27 | 478 | 1.08 |
| 1005 | 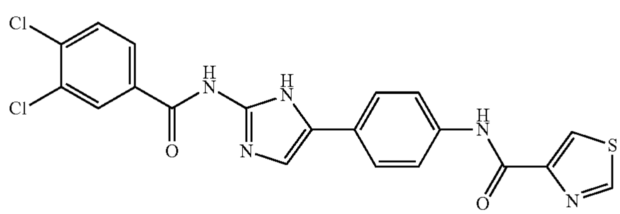 [SMILES: O=C(Nc1ncc(-c2ccc(NC(=O)c3cscn3)cc2)[nH]1)c1ccc(Cl)c(Cl)c1] | A27 | 457.9 459.9 | 1.08 |
| 1006 | 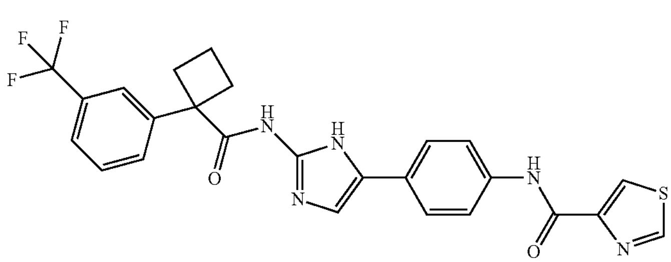 [SMILES: O=C(Nc1ccc(-c2cnc(NC(=O)C3(c4cccc(C(F)(F)F)c4)CCC3)[nH]2)cc1)c1cscn1] | A27 | 512 | 1.55 |

TABLE 1-continued

| Cmpd # | Structure | Example # for synthesis | [M + H]+ | $t_R$ (min) |
|---|---|---|---|---|
| 1007 | 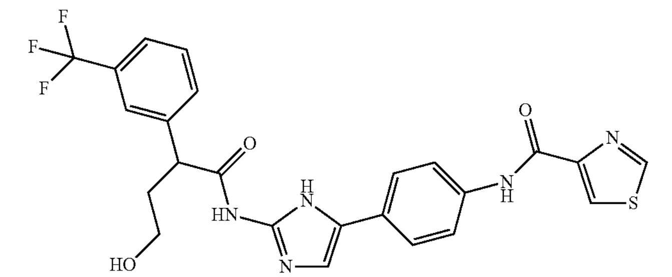 [SMILES: O=C(Nc1ccc(-c2cnc(NC(=O)C(CCO)c3cccc(C(F)(F)F)c3)[nH]2)cc1)c1cscn1] | A27 | 516 | 1.25 |
| 1008 | 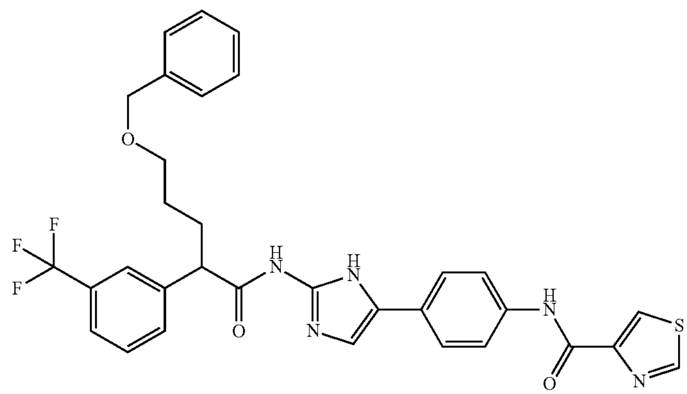 [SMILES: O=C(Nc1ccc(-c2cnc(NC(=O)C(CCCOCc3ccccc3)c3cccc(C(F)(F)F)c3)[nH]2)cc1)c1cscn1] | A27 | 620.1 | 1.74 |
| 1009 | 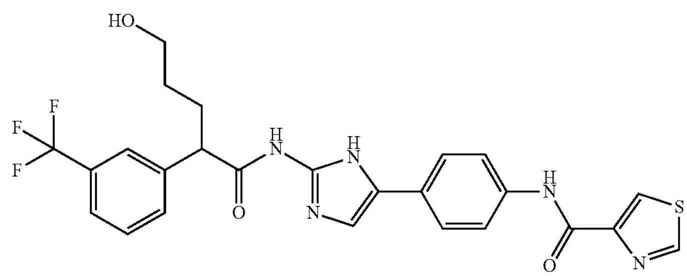 [SMILES: O=C(Nc1ccc(-c2cnc(NC(=O)C(CCCO)c3cccc(C(F)(F)F)c3)[nH]2)cc1)c1cscn1] | A27 | 530 | 1.27 |
| 1010 | 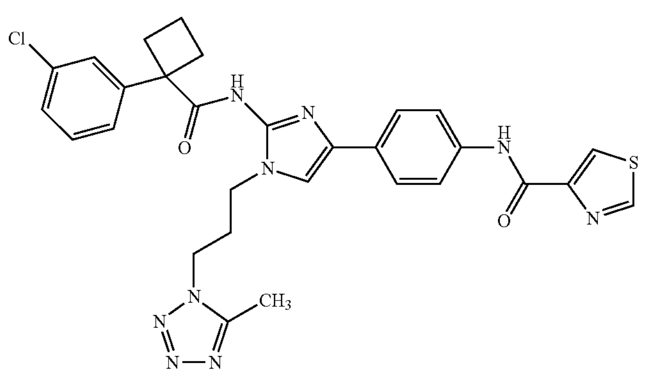 [SMILES: Cc1nnnn1CCCn1cc(-c2ccc(NC(=O)c3cscn3)cc2)nc1NC(=O)C1(c2cccc(Cl)c2)CCC1] | A27 | 602 | 1.09 |
| 1011 | 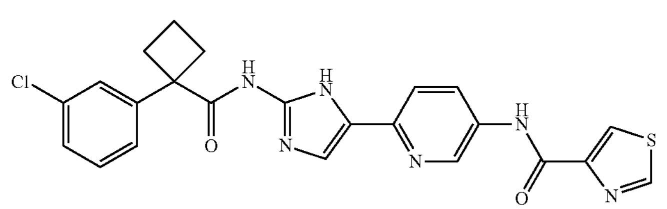 [SMILES: O=C(Nc1ccc(-c2cnc(NC(=O)C3(c4cccc(Cl)c4)CCC3)[nH]2)nc1)c1cscn1] | A27 | 479.0 481.0 | 1.37 |

TABLE 1-continued

| Cmpd # | Structure | Example # for synthesis | [M + H]+ | $t_R$ (min) |
|---|---|---|---|---|
| 1012 | 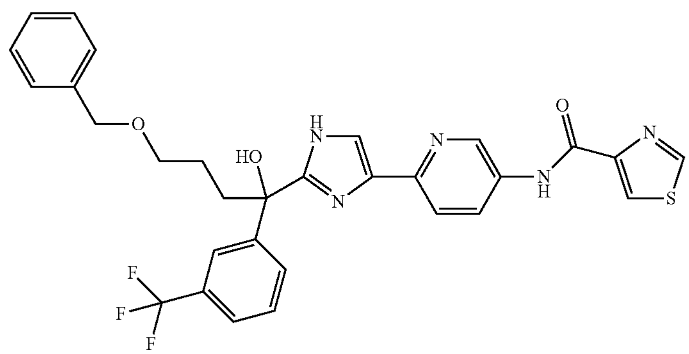 [SMILES: O=C(Nc1ccc(-c2c[nH]c(C(O)(CCCOCc3ccccc3)c3cccc(C(F)(F)F)c3)n2)nc1)c1cscn1] | A11 | 594.4 | 1.3 |
| 1013 | 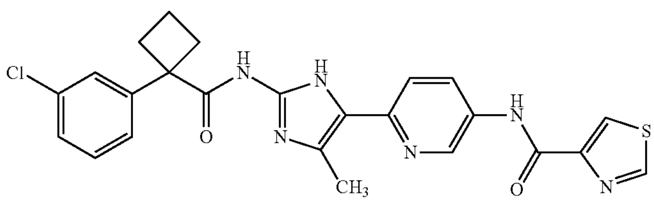 [SMILES: Cc1nc(NC(=O)C2(c3cccc(Cl)c3)CCC2)[nH]c1-c1ccc(NC(=O)c2cscn2)cn1] | A27 | 493.1 495.0 | 0.96 |
| 1014 | 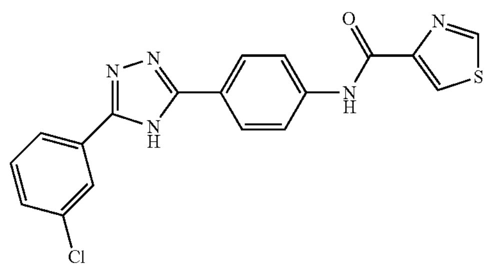 [SMILES: O=C(Nc1ccc(-c2nnc(-c3cccc(Cl)c3)[nH]2)cc1)c1cscn1] | A7 | 381.8 384.1 | 1.3 |
| 1015 | 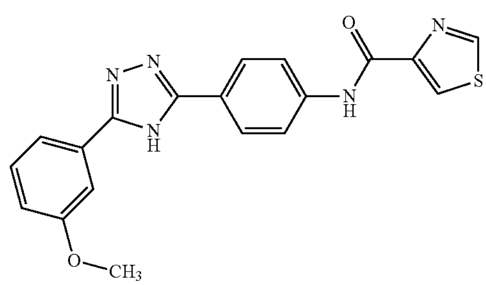 [SMILES: COc1cccc(-c2nnc(-c3ccc(NC(=O)c4cscn4)cc3)[nH]2)c1] | A7 | 377.8 | 1.10 |
| 1016 | 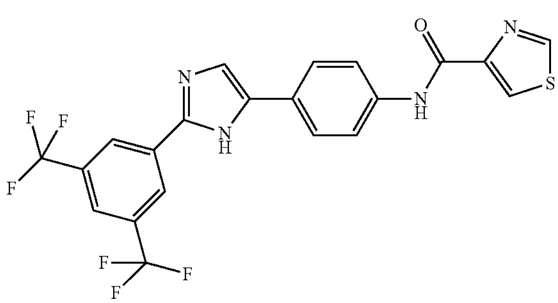 [SMILES: O=C(Nc1ccc(-c2cnc(-c3cc(C(F)(F)F)cc(C(F)(F)F)c3)[nH]2)cc1)c1cscn1] | A3 | 483.1 | 1.26 |

TABLE 1-continued

| Cmpd # | Structure | Example # for synthesis | [M + H]+ | $t_R$ (min) |
|---|---|---|---|---|
| 1017 | 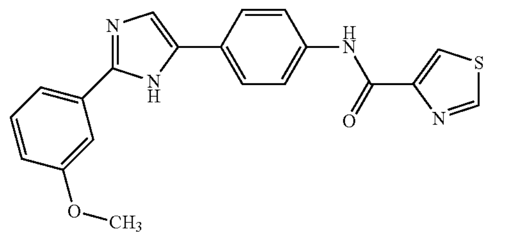 [SMILES: COc1cccc(-c2ncc(-c3ccc(NC(=O)c4cscn4)cc3)[nH]2)c1] | A2 | 377 | 1.0 |
| 1018 | 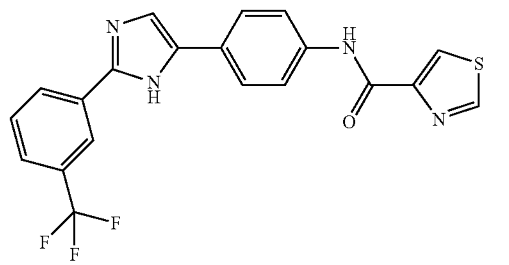 [SMILES: O=C(Nc1ccc(-c2cnc(-c3cccc(C(F)(F)F)c3)[nH]2)cc1)c1cscn1] | A2 | 415 | 1.33 |
| 1019 | 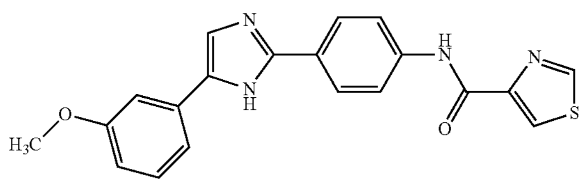 [SMILES: COc1cccc(-c2cnc(-c3ccc(NC(=O)c4cscn4)cc3)[nH]2)c1] | A15 | 377.1 | 0.89 |
| 1020 | 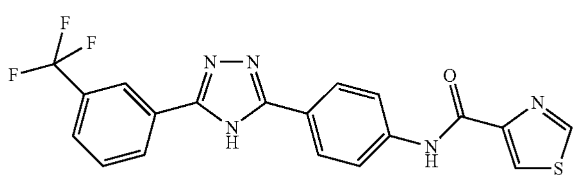 [SMILES: O=C(Nc1ccc(-c2nnc(-c3cccc(C(F)(F)F)c3)[nH]2)cc1)c1cscn1] | A7 | 416.1 | 1.37 |
| 1021 | 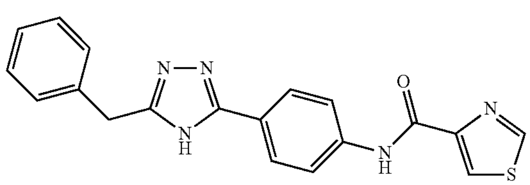 [SMILES: O=C(Nc1ccc(-c2nnc(Cc3ccccc3)[nH]2)cc1)c1cscn1] | A7 | 362.1 | 0.98 |
| 1022 | 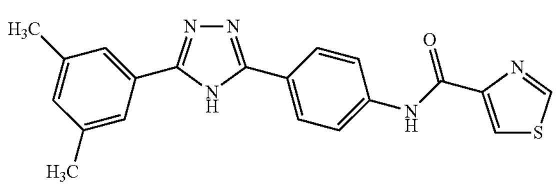 [SMILES: Cc1cc(C)cc(-c2nnc(-c3ccc(NC(=O)c4cscn4)cc3)[nH]2)c1] | A7 | 376.1 | 1.28 |
| 1023 | 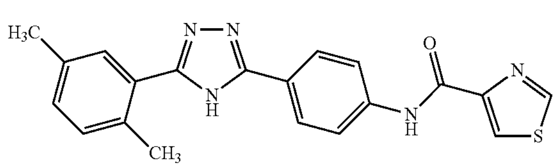 [SMILES: Cc1ccc(C)c(-c2nnc(-c3ccc(NC(=O)c4cscn4)cc3)[nH]2)c1] | A7 | 376.0 | 1.23 |

TABLE 1-continued

| Cmpd # | Structure | Example # for synthesis | [M + H]+ | t_R (min) |
|---|---|---|---|---|
| 1024 | 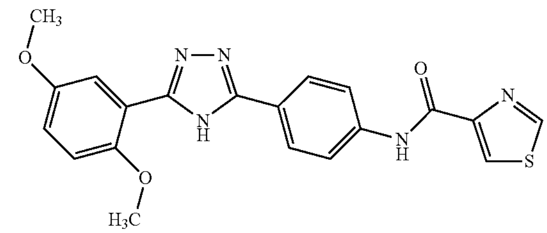 [SMILES: COc1ccc(OC)c(-c2nnc(-c3ccc(NC(=O)c4cscn4)cc3)[nH]2)c1] | A7 | 408.1 | 1.17 |
| 1025 | 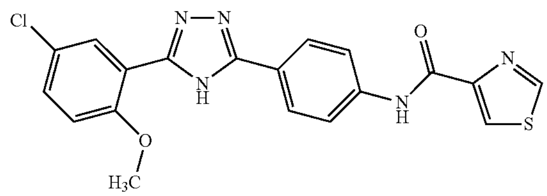 [SMILES: COc1ccc(Cl)cc1-c1nnc(-c2ccc(NC(=O)c3cscn3)cc2)[nH]1] | A7 | 412.0 414.0 | 1.38 |
| 1026 | 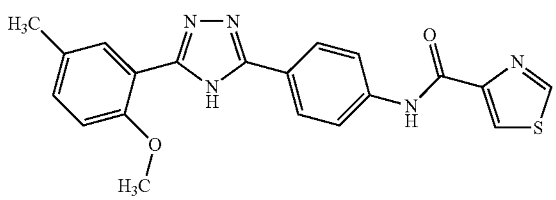 [SMILES: COc1ccc(C)cc1-c1nnc(-c2ccc(NC(=O)c3cscn3)cc2)[nH]1] | A7 | 392.1 | 1.26 |
| 1027 | 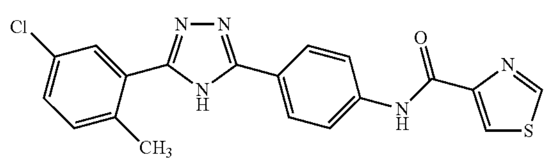 [SMILES: Cc1ccc(Cl)cc1-c1nnc(-c2ccc(NC(=O)c3cscn3)cc2)[nH]1] | A7 | 396.0 398.1 | 1.38 |
| 1028 | 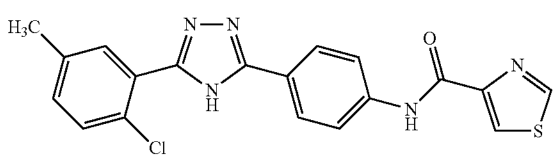 | A7 | 396.1 398.2 | 1.25 |
| 1029 | 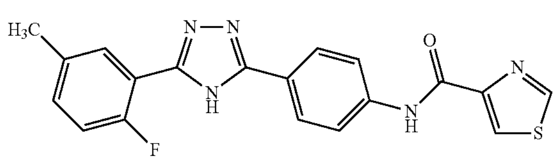 [SMILES: Cc1ccc(Cl)c(-c2nnc(-c3ccc(NC(=O)c4cscn4)cc3)[nH]2)c1] | A7 | 380.1 | 1.22 |
| 1030 | 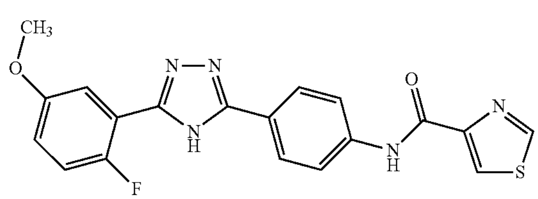 [SMILES: COc1ccc(F)c(-c2nnc(-c3ccc(NC(=O)c4cscn4)cc3)[nH]2)c1] | A7 | 396.1 | 1.14 |
| 1031 | 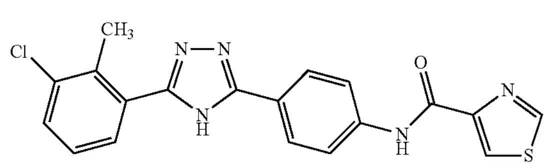 [SMILES: Cc1c(Cl)cccc1-c1nnc(-c2ccc(NC(=O)c3cscn3)cc2)[nH]1] | A7 | 396.0 398.1 | 1.32 |

TABLE 1-continued

| Cmpd # | Structure | Example # for synthesis | [M + H]+ | $t_R$ (min) |
|---|---|---|---|---|
| 1032 | 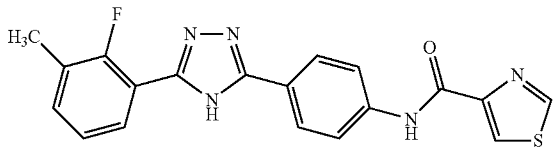 [SMILES: Cc1cccc(-c2nnc(-c3ccc(NC(=O)c4cscn4)cc3)[nH]2)c1F] | A7 | 380.1 | 1.21 |
| 1033 | 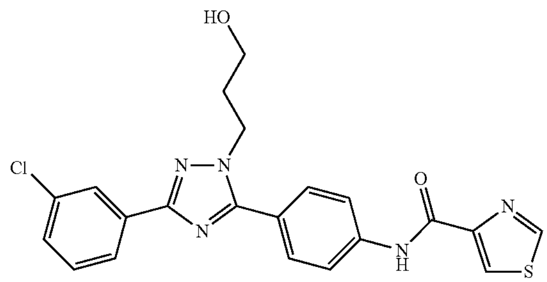 [SMILES: O=C(Nc1ccc(-c2nc(-c3cccc(Cl)c3)nn2CCCO)cc1)c1cscn1] | A8 | — | 1.28 |
| 1034 | 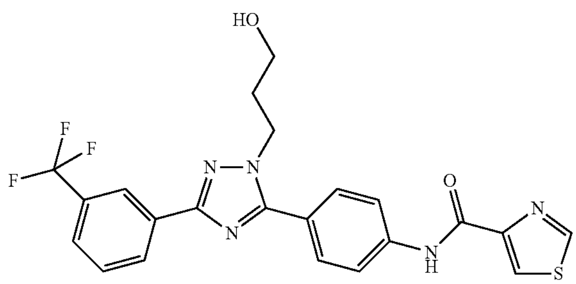 [SMILES: O=C(Nc1ccc(-c2nc(-c3cccc(C(F)(F)F)c3)nn2CCCO)cc1)c1cscn1] | A8 | — | 1.35 |
| 1035 | 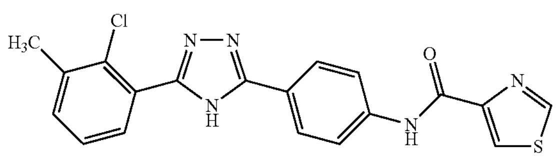 [SMILES: Cc1cccc(-c2nnc(-c3ccc(NC(=O)c4cscn4)cc3)[nH]2)c1Cl] | A7 | 396.0 398.0 | 1.22 |
| 1036 | 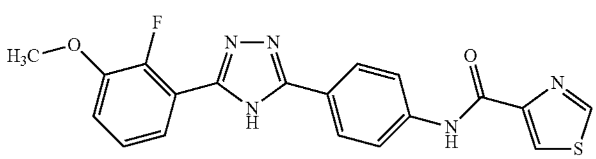 [SMILES: COc1cccc(-c2nnc(-c3ccc(NC(=O)c4cscn4)cc3)[nH]2)c1F] | A7 | 396 | 1.11 |
| 1037 | 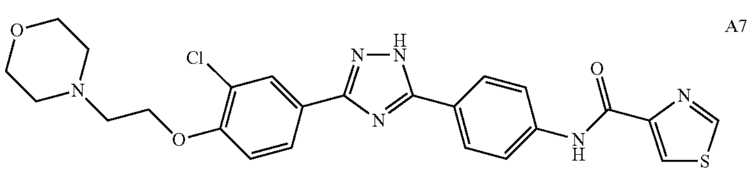 | A7 | 511.0 513.0 | 0.8 |
| 1038 | 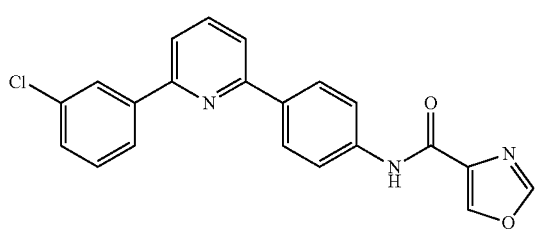 [SMILES: O=C(Nc1ccc(-c2cccc(-c3cccc(Cl)c3)n2)cc1)c1cocn1] | A33 | 376.0 378.0 | 1.67 |

TABLE 1-continued

| Cmpd # | Structure | Example # for synthesis | [M + H]+ | $t_R$ (min) |
|---|---|---|---|---|
| 1039 | 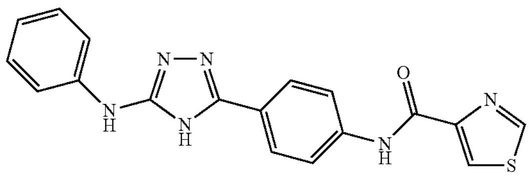 [SMILES: O=C(Nc1ccc(-c2nnc(Nc3ccccc3)[nH]2)cc1)c1cscn1] | A28 | 363.1 | 1.0 |
| 1040 | 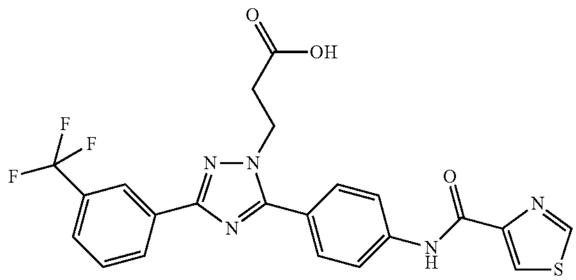 [SMILES: O=C(O)CCn1nc(-c2cccc(C(F)(F)F)c2)nc1-c1ccc(NC(=O)c2cscn2)cc1] | A24 | 488.1 | 1.34 |
| 1041 | 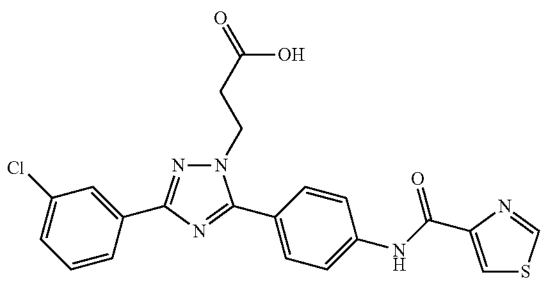 [SMILES: O=C(O)CCn1nc(-c2cccc(Cl)c2)nc1-c1ccc(NC(=O)c2cscn2)cc1] | A24 | 454.1 456.1 | 1.27 |
| 1042 | 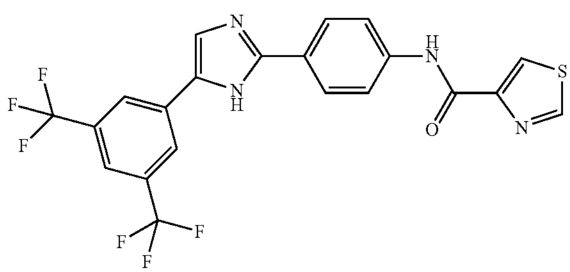 [SMILES: O=C(Nc1ccc(-c2ncc(-c3cc(C(F)(F)F)cc(C(F)(F)F)c3)[nH]2)cc1)c1cscn1] | A15 | 483.1 | 2.14 |
| 1043 | 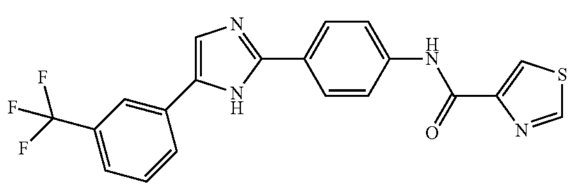 [SMILES: O=C(Nc1ccc(-c2ncc(-c3cccc(C(F)(F)F)c3)[nH]2)cc1)c1cscn1] | A15 | 415.1 | 1.9 |
| 1044 | 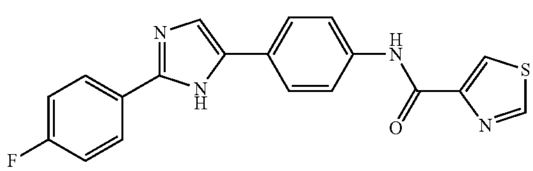 [SMILES: O=C(Nc1ccc(-c2cnc(-c3ccc(F)cc3)[nH]2)cc1)c1cscn1] | A2 | 364.6 | 0.62 |
| 1045 | 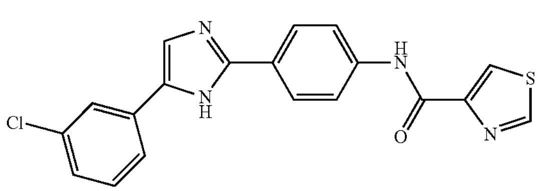 [SMILES: O=C(Nc1ccc(-c2ncc(-c3cccc(Cl)c3)[nH]2)cc1)c1cscn1] | A15 | 381 | 1.3 |

TABLE 1-continued

| Cmpd # | Structure | Example # for synthesis | [M + H]+ | $t_R$ (min) |
|---|---|---|---|---|
| 1046 | 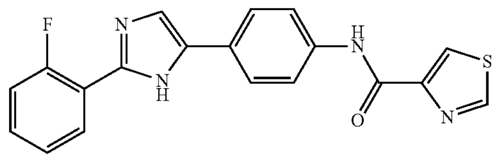 [SMILES: O=C(Nc1ccc(-c2cnc(-c3ccccc3F)[nH]2)cc1)c1cscn1] | A2 | 364.7 | 1.08 |
| 1047 | 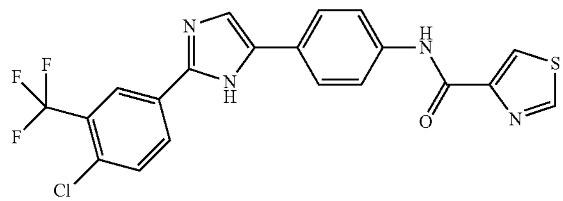 [SMILES: O=C(Nc1ccc(-c2cnc(-c3ccc(Cl)c(C(F)(F)F)c3)[nH]2)cc1)c1cscn1] | A2 | 448.7 450.3 | 1.13 |
| 1048 | 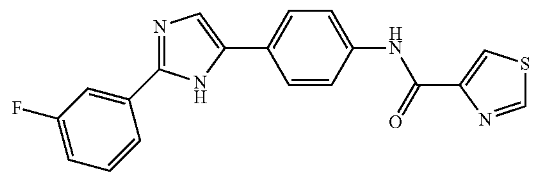 [SMILES: O=C(Nc1ccc(-c2cnc(-c3cccc(F)c3)[nH]2)cc1)c1cscn1] | A2 | 364.5 | 1.11 |
| 1049 | 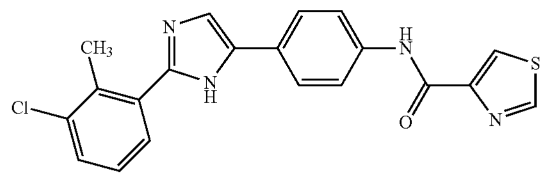 [SMILES: Cc1c(Cl)cccc1-c1ncc(-c2ccc(NC(=O)c3cscn3)cc2)[nH]1] | A2 | 394.8 | 1.19 |
| 1050 | 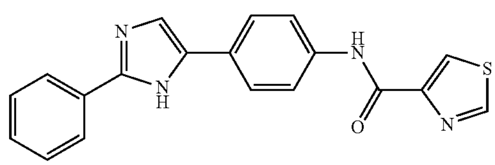 [SMILES: O=C(Nc1ccc(-c2cnc(-c3ccccc3)[nH]2)cc1)c1cscn1] | A2 | 346.7 | 0.92 |
| 1051 | 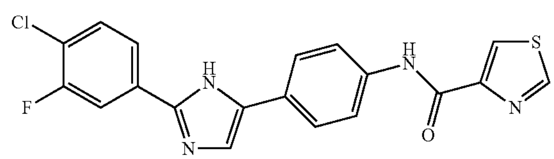 [SMILES: O=C(Nc1ccc(-c2cnc(-c3ccc(Cl)c(F)c3)[nH]2)cc1)c1cscn1] | A2 | 398.6 400.1 | 0.89 |
| 1052 | 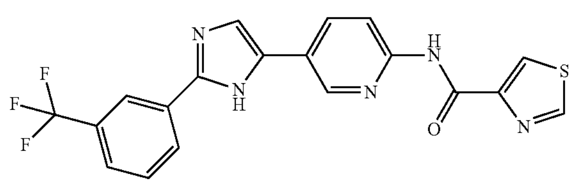 [SMILES: O=C(Nc1ccc(-c2cnc(-c3cccc(C(F)(F)F)c3)[nH]2)cn1)c1cscn1] | A16 | 415.6 | 1.37 |
| 1053 | 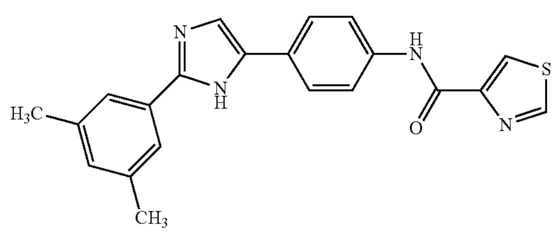 [SMILES: Cc1cc(C)cc(-c2ncc(-c3ccc(NC(=O)c4cscn4)cc3)[nH]2)c1] | A2 | 375 | 0.99 |

TABLE 1-continued
| Cmpd # | Structure | Example # for synthesis | [M + H]+ | $t_R$ (min) |
|---|---|---|---|---|
| 1054 | 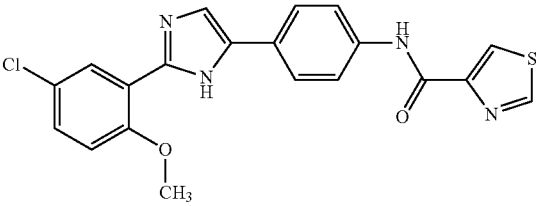 [SMILES: COc1ccc(Cl)cc1-c1ncc(-c2ccc(NC(=O)c3cscn3)cc2)[nH]1] | A2 | 410.6 412.6 | 0.79 |
| 1055 | 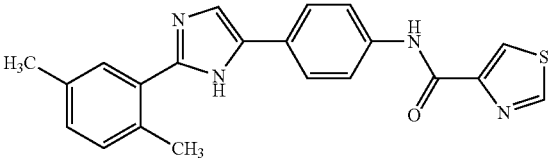 [SMILES: Cc1ccc(C)c(-c2ncc(-c3ccc(NC(=O)c4cscn4)cc3)[nH]2)c1] | A2 | 374.7 | 0.65 |
| 1056 | 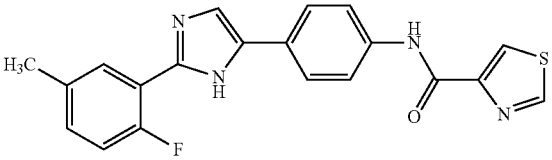 [SMILES: Cc1ccc(F)c(-c2ncc(-c3ccc(NC(=O)c4cscn4)cc3)[nH]2)c1] | A2 | 379 | 0.87 |
| 1057 | 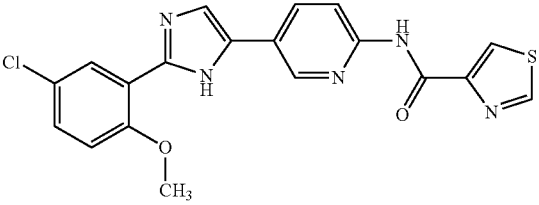 [SMILES: COc1ccc(Cl)cc1-c1ncc(-c2ccc(NC(=O)c3cscn3)nc2)[nH]1] | A16 | 411.5 | 1.41 |
| 1058 | 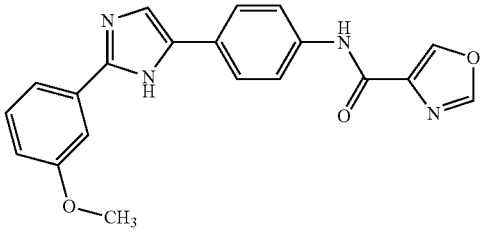 [SMILES: COc1cccc(-c2ncc(-c3ccc(NC(=O)c4cocn4)cc3)[nH]2)c1] | A31 | 361.1 | 0.91 |
| 1059 | 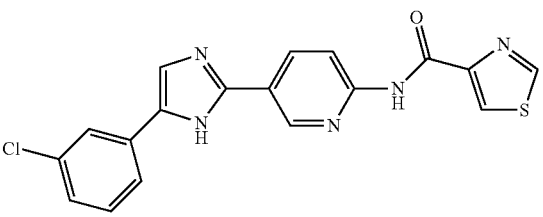 [SMILES: O=C(Nc1ccc(-c2ncc(-c3cccc(Cl)c3)[nH]2)cn1)c1cscn1] | A14 | 382 | 1.35 |
| 1060 | 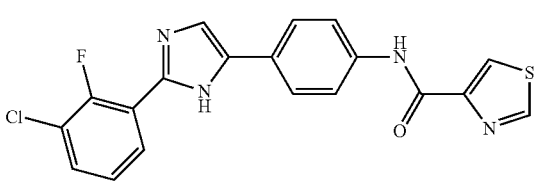 [SMILES: O=C(Nc1ccc(-c2cnc(-c3cccc(Cl)c3F)[nH]2)cc1)c1cscn1] | A2 | 398.9 | 1.32 |

TABLE 1-continued

| Cmpd # | Structure | Example # for synthesis | [M + H]+ | $t_R$ (min) |
|---|---|---|---|---|
| 1061 | 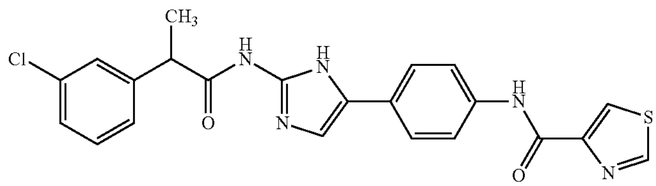 [SMILES: CC(C(=O)Nc1ncc(-c2ccc(NC(=O)c3cscn3)cc2)[nH]1)c1cccc(Cl)c1] | A27 | 452 | 1.36 |
| 1062 | 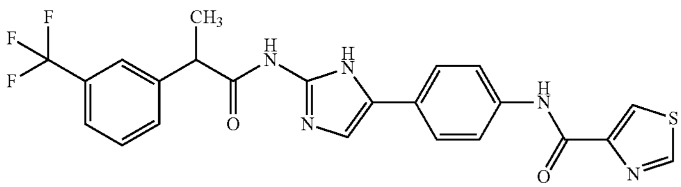 [SMILES: CC(C(=O)Nc1ncc(-c2ccc(NC(=O)c3cscn3)cc2)[nH]1)c1cccc(C(F)(F)F)c1] | A27 | 486 | 1.06 |
| 1063 | 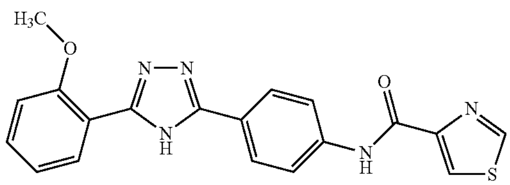 [SMILES: COc1ccccc1-c1nnc(-c2ccc(NC(=O)c3cscn3)cc2)[nH]1] | A7 | 378.1 | 1.15 |
| 1064 | 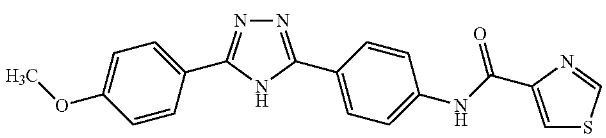 [SMILES: COc1ccc(-c2nnc(-c3ccc(NC(=O)c4cscn4)cc3)[nH]2)cc1] | A7 | 378.1 | 1.05 |
| 1065 | 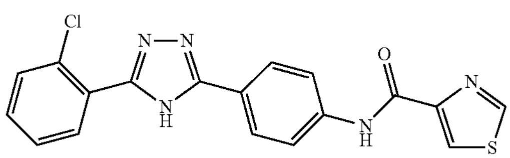 | A7 | 382.1<br>384.1 | 1.12 |
| 1066 | 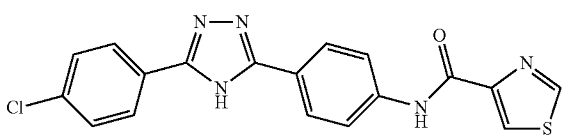 [SMILES: O=C(Nc1ccc(-c2nnc(-c3ccc(Cl)cc3)[nH]2)cc1)c1cscn1] | A7 | 382.0<br>384.1 | 1.28 |
| 1067 | 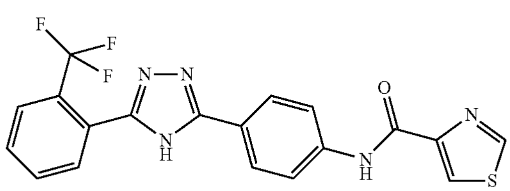 [SMILES: O=C(Nc1ccc(-c2nnc(-c3ccccc3C(F)(F)F)[nH]2)cc1)c1cscn1] | A7 | 416.1 | 1.17 |
| 1068 | 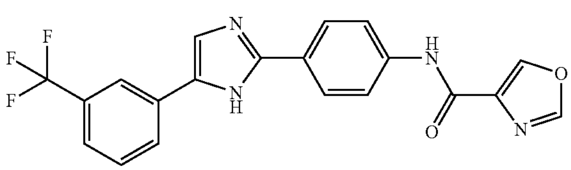 [SMILES: O=C(Nc1ccc(-c2ncc(-c3cccc(C(F)(F)F)c3)[nH]2)cc1)c1cocn1] | A32 | 399.4 | 1.84 |
| 1069 | 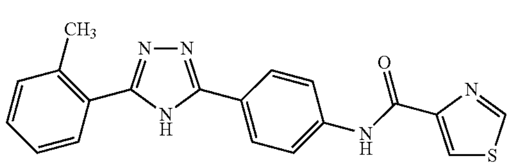 | A7 | 362.1 | 1.13 |

TABLE 1-continued

| Cmpd # | Structure | Example # for synthesis | [M + H]+ | $t_R$ (min) |
|---|---|---|---|---|
| 1070 | 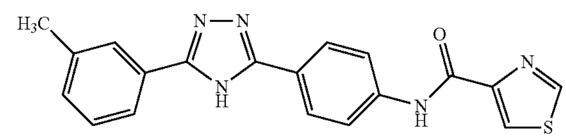 [SMILES: Cc1cccc(-c2nnc(-c3ccc(NC(=O)c4cscn4)cc3)[nH]2)c1] | A7 | 362.1 | 1.17 |
| 1071 | 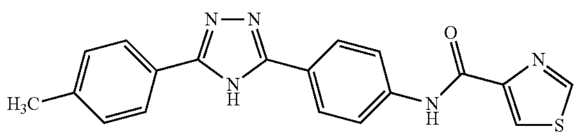 [SMILES: Cc1ccc(-c2nnc(-c3ccc(NC(=O)c4cscn4)cc3)[nH]2)cc1] | A7 | 362.1 | 1.16 |
| 1072 | 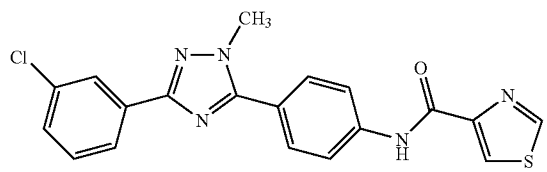 [SMILES: Cn1nc(-c2cccc(Cl)c2)nc1-c1ccc(NC(=O)c2cscn2)cc1] | A7 | 396.1 398.2 | 1.44 |
| 1073 | 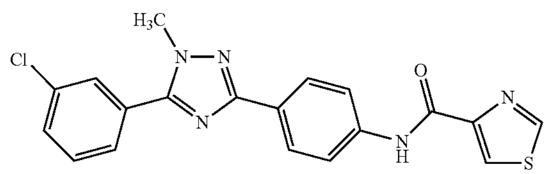 [SMILES: Cn1nc(-c2ccc(NC(=O)c3cscn3)cc2)nc1-c1cccc(Cl)c1] | A7 | 396.1 398.1 | 1.34 |
| 1074 | 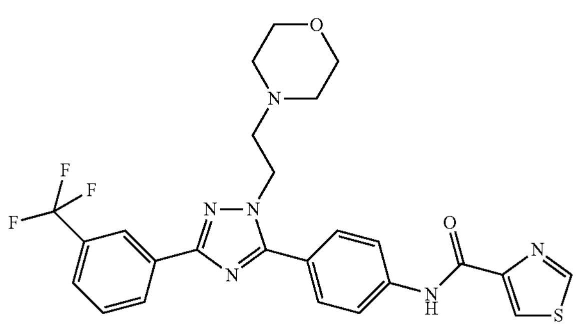 [SMILES: O=C(Nc1ccc(-c2nc(-c3cccc(C(F)(F)F)c3)nn2CCN2CCOCC2)cc1)c1cscn1] | A26 | 529.2 | 1.14 |
| 1075 | 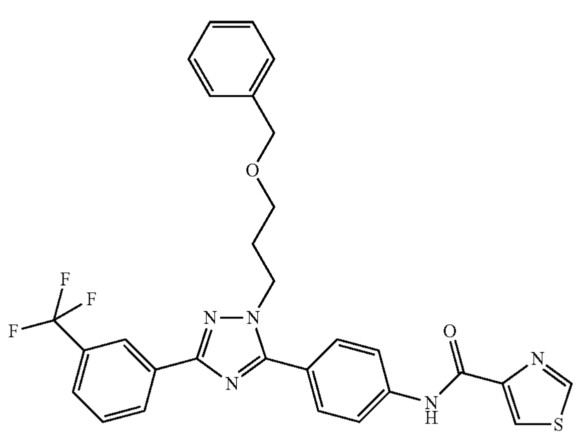 [SMILES: O=C(Nc1ccc(-c2nc(-c3cccc(C(F)(F)F)c3)nn2CCCOCc2ccccc2)cc1)c1cscn1] | A26 | 564.2 | 1.93 |

TABLE 1-continued

| Cmpd # | Structure | Example # for synthesis | [M + H]+ | $t_R$ (min) |
|---|---|---|---|---|
| 1076 | 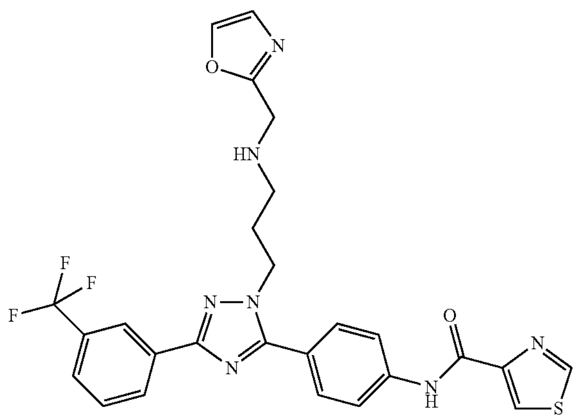 [SMILES: O=C(Nc1ccc(-c2nc(-c3cccc(C(F)(F)F)c3)nn2CCCNCc2ncco2)cc1)c1cscn1] | A26 | 554.1 | 1.14 |
| 1077 | 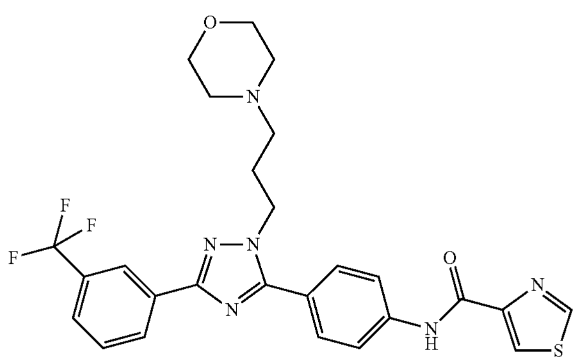 [SMILES: O=C(Nc1ccc(-c2nc(-c3cccc(C(F)(F)F)c3)nn2CCCN2CCOCC2)cc1)c1cscn1] | A26 | 543.2 | 1.15 |
| 1078 | 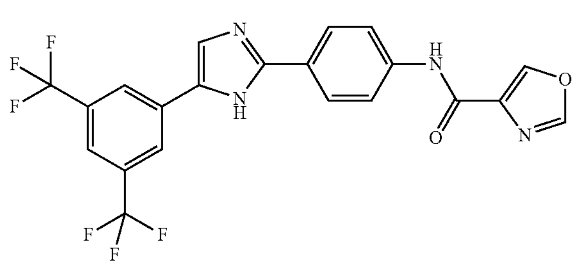 [SMILES: O=C(Nc1ccc(-c2ncc(-c3cc(C(F)(F)F)cc(C(F)(F)F)c3)[nH]2)cc1)c1cocn1] | A32 | 467.1 | 2.1 |
| 1079 | 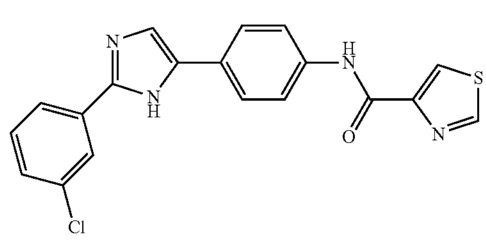 [SMILES: O=C(Nc1ccc(-c2cnc(-c3cccc(Cl)c3)[nH]2)cc1)c1cscn1] | A2 | 381 | 1.25 |

TABLE 1-continued

| Cmpd # | Structure | Example # for synthesis | [M + H]+ | $t_R$ (min) |
|---|---|---|---|---|
| 1080 | 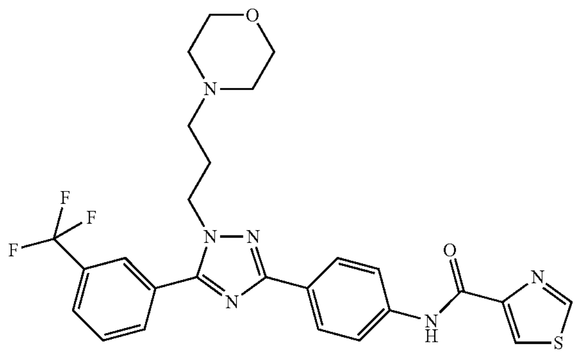 [SMILES: O=C(Nc1ccc(-c2nc(-c3cccc(C(F)(F)F)c3)n(CCCN3CCOCC3)n2)cc1)c1cscn1] | A26 | 543.1 | 1.04 |
| 1081 | 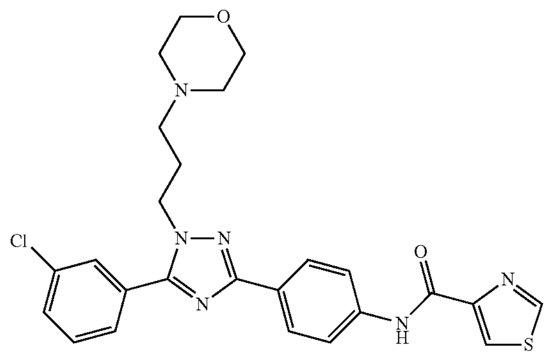 [SMILES: O=C(Nc1ccc(-c2nc(-c3cccc(Cl)c3)n(CCCN3CCOCC3)n2)cc1)c1cscn1] | A26 | 509.1<br>511.1 | 0.97 |
| 1082 | 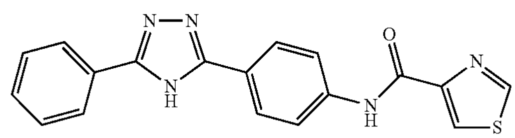 [SMILES: O=C(Nc1ccc(-c2nnc(-c3ccccc3)[nH]2)cc1)c1cscn1] | A2 | 348.0 | 1.08 |
| 1083 | 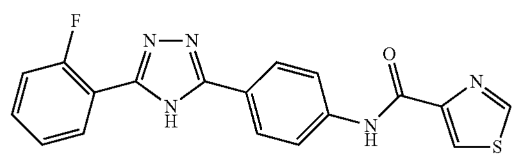 | A2 | 366 | 1.1 |
| 1084 | 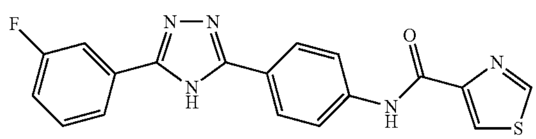 [SMILES: O=C(Nc1ccc(-c2nnc(-c3cccc(F)c3)[nH]2)cc1)c1cscn1] | A2 | 366.1 | 1.19 |
| 1085 | 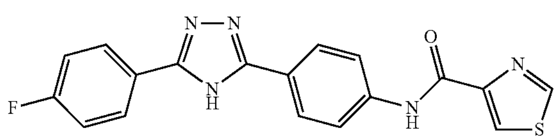 [SMILES: O=C(Nc1ccc(-c2nnc(-c3ccc(F)cc3)[nH]2)cc1)c1cscn1] | A2 | 366.1 | 1.15 |
| 1086 | 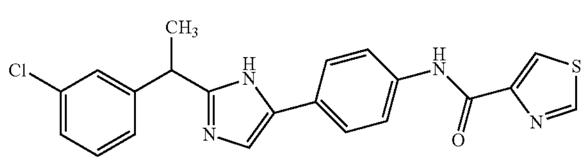 [SMILES: CC(c1cccc(Cl)c1)c1ncc(-c2ccc(NC(=O)c3cscn3)cc2)[nH]1] | A21 | 409.1 | 0.99 |

TABLE 1-continued

| Cmpd # | Structure | Example # for synthesis | [M + H]+ | $t_R$ (min) |
|---|---|---|---|---|
| 1087 | 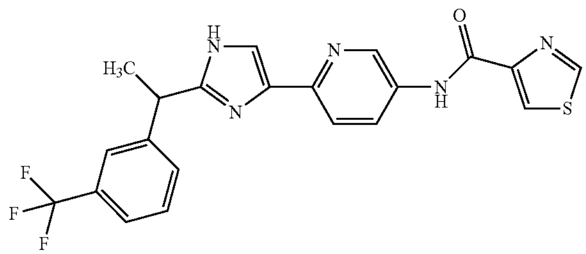 [SMILES: CC(c1cccc(C(F)(F)F)c1)c1nc(-c2ccc(NC(=O)c3cscn3)cn2)c[nH]1] | A11 | 444.2 | 1.0 |
| 1088 | 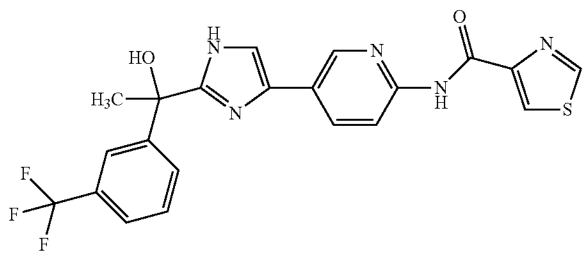 [SMILES: CC(O)(c1cccc(C(F)(F)F)c1)c1nc(-c2ccc(NC(=O)c3cscn3)nc2)c[nH]1] | A11 | 460.2 | 1.0 |
| 1089 | 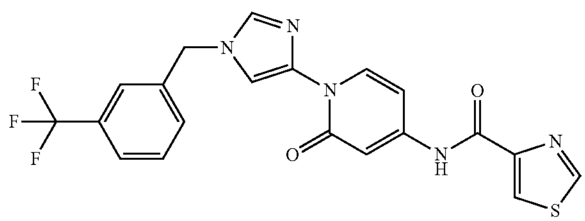 [SMILES: O=C(Nc1ccn(-c2cn(Cc3cccc(C(F)(F)F)c3)cn2)c(=O)c1)c1cscn1] | A29 | 446.1 | 1.1 |
| 1091 | 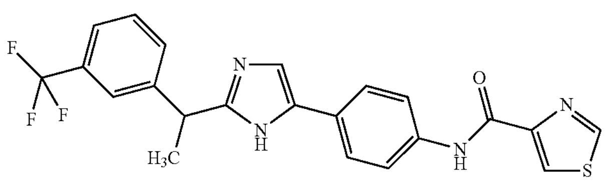 [SMILES: CC(c1cccc(C(F)(F)F)c1)c1ncc(-c2ccc(NC(=O)c3cscn3)cc2)[nH]1] | A21 | 443.2 | 1.05 |
| 1092 | 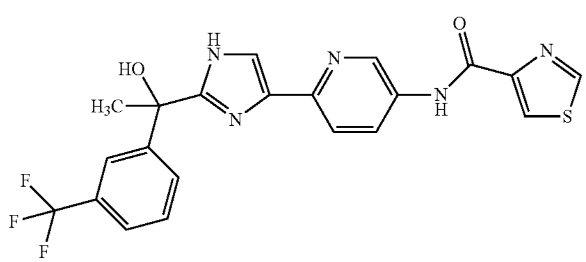 [SMILES: CC(O)(c1cccc(C(F)(F)F)c1)c1nc(-c2ccc(NC(=O)c3cscn3)cn2)c[nH]1] | A11 | 460.3 | 1 |
| 1093 | 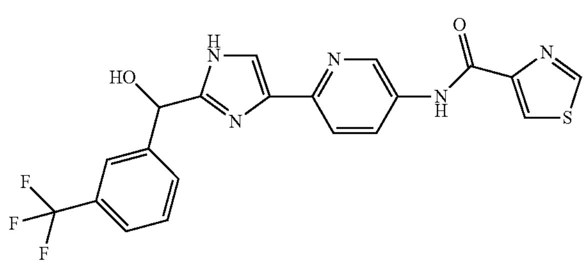 [SMILES: O=C(Nc1ccc(-c2c[nH]c(C(O)c3cccc(C(F)(F)F)c3)n2)nc1)c1cscn1] | A11 | 446.2 | 0.9 |

TABLE 1-continued

| Cmpd # | Structure | Example # for synthesis | [M + H]+ | $t_R$ (min) |
|---|---|---|---|---|
| 1094 | 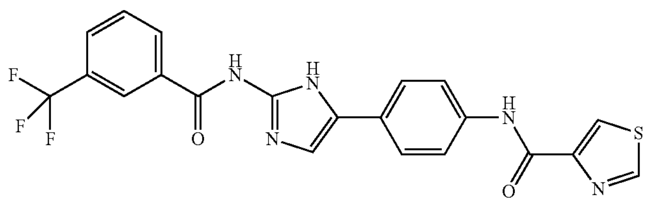 [SMILES: O=C(Nc1ncc(-c2ccc(NC(=O)c3cscn3)cc2)[nH]1)c1cccc(C(F)(F)F)c1] | A27 | 458 | 1.24 |
| 1095 | 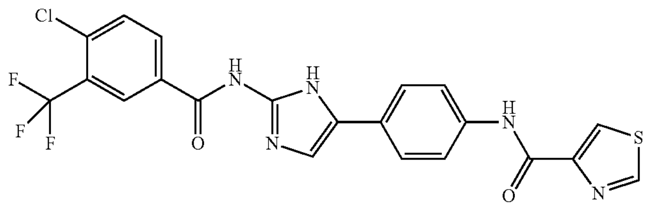 [SMILES: O=C(Nc1ncc(-c2ccc(NC(=O)c3cscn3)cc2)[nH]1)c1ccc(Cl)c(C(F)(F)F)c1] | A27 | 491.9 | 1.46 |
| 1096 | 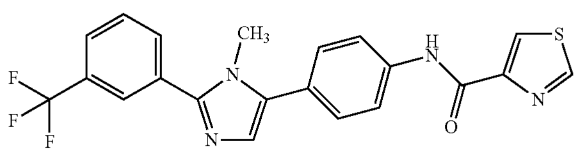 [SMILES: Cn1c(-c2ccc(NC(=O)c3cscn3)cc2)cnc1-c1cccc(C(F)(F)F)c1] | A19 | 429.1 | 1.31 |
| 1097 | 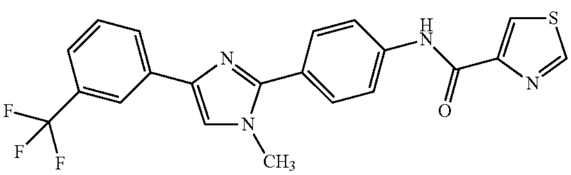 [SMILES: Cn1cc(-c2cccc(C(F)(F)F)c2)nc1-c1ccc(NC(=O)c2cscn2)cc1] | A18 | 429.1 | 1.5 |
| 1098 | 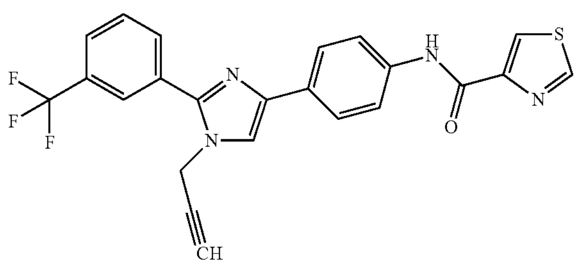 [SMILES: C#CCn1cc(-c2ccc(NC(=O)c3cscn3)cc2)nc1-c1cccc(C(F)(F)F)c1] | A20 | 453 | 1.5 |
| 1099 | 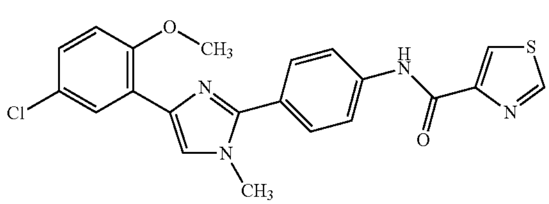 [SMILES: COc1ccc(Cl)cc1-c1cn(C)c(-c2ccc(NC(=O)c3cscn3)cc2)n1] | A18 | 425.0 427.0 | 1.34 |
| 1100 | 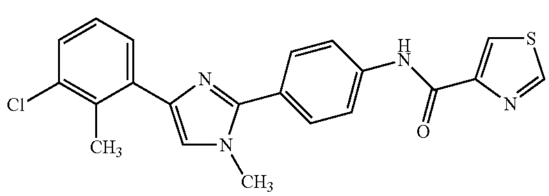 [SMILES: Cc1c(Cl)cccc1-c1cn(C)c(-c2ccc(NC(=O)c3cscn3)cc2)n1] | A18 | 409.0 411.0 | 0.75 |

TABLE 1-continued

| Cmpd # | Structure | Example # for synthesis | [M + H]+ | $t_R$ (min) |
|---|---|---|---|---|
| 1101 | 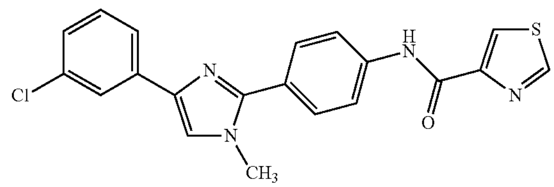 [SMILES: Cn1cc(-c2cccc(Cl)c2)nc1-c1ccc(NC(=O)c2cscn2)cc1] | A18 | 395.0 396.9 | 1.35 |
| 1102 | 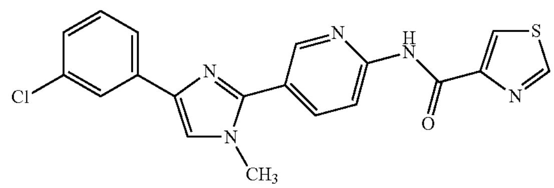 [SMILES: Cn1cc(-c2cccc(Cl)c2)nc1-c1ccc(NC(=O)c2cscn2)nc1] | A17 | 396.0 397.9 | 1.43 |
| 1103 | 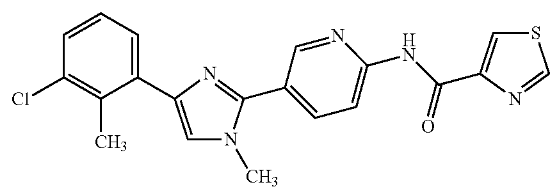 [SMILES: Cc1c(Cl)cccc1-c1cn(C)c(-c2ccc(NC(=O)c3cscn3)nc2)n1] | A17 | 410.0 411.9 | 1.45 |
| 1104 | 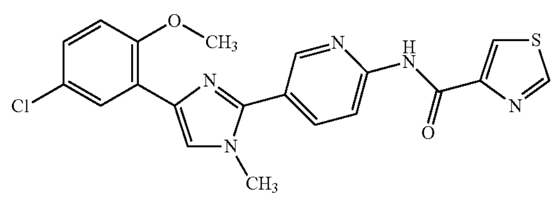 [SMILES: COc1ccc(Cl)cc1-c1cn(C)c(-c2ccc(NC(=O)c3cscn3)nc2)n1] | A17 | 426.0 427.9 | 1.48 |
| 1105 | 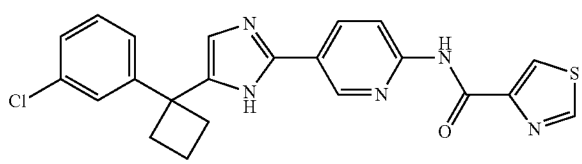 [SMILES: O=C(Nc1ccc(-c2ncc(C3(c4cccc(Cl)c4)CCC3)[nH]2)cn1)c1cscn1] | A14 | 436.0 438.0 | 1.43 |
| 1106 | 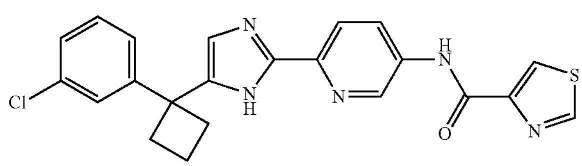 [SMILES: O=C(Nc1ccc(-c2ncc(C3(c4cccc(Cl)c4)CCC3)[nH]2)nc1)c1cscn1] | A14 | 436.0 438.0 | 1.41 |
| 1107 | 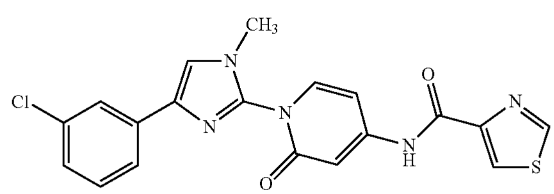 [SMILES: Cn1cc(-c2cccc(Cl)c2)nc1-n1ccc(NC(=O)c2cscn2)cc1=O] | A12 | 412 | 1.38 |
| 1108 | 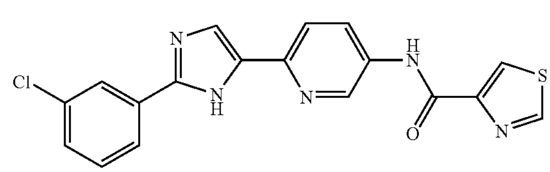 [SMILES: O=C(Nc1ccc(-c2cnc(-c3cccc(Cl)c3)[nH]2)nc1)c1cscn1] | A16 | 382.0 384.0 | 0.77 |

TABLE 1-continued

| Cmpd # | Structure | Example # for synthesis | [M + H]+ | t_R (min) |
|---|---|---|---|---|
| 1109 | 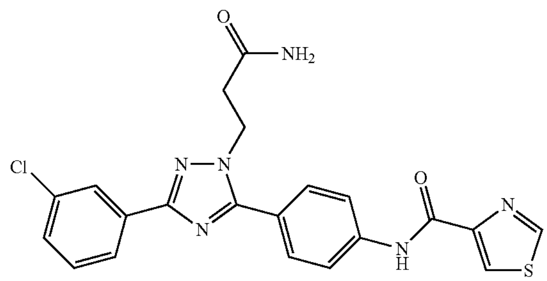 [SMILES: NC(=O)CCn1nc(-c2cccc(Cl)c2)nc1-c1ccc(NC(=O)c2cscn2)cc1] | A24 | 453.2 455.2 | 1.14 |
| 1110 | 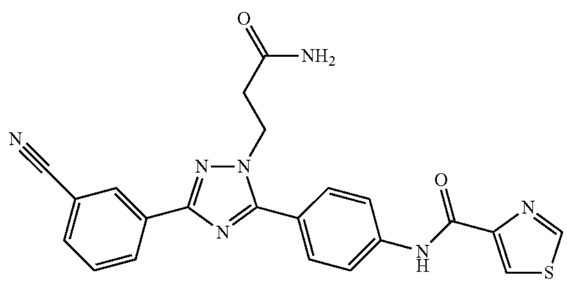 [SMILES: N#Cc1cccc(-c2nc(-c3ccc(NC(=O)c4cscn4)cc3)n(CCC(N)=O)n2)c1] | A24 | 444.2 | 0.98 |
| 1111 | 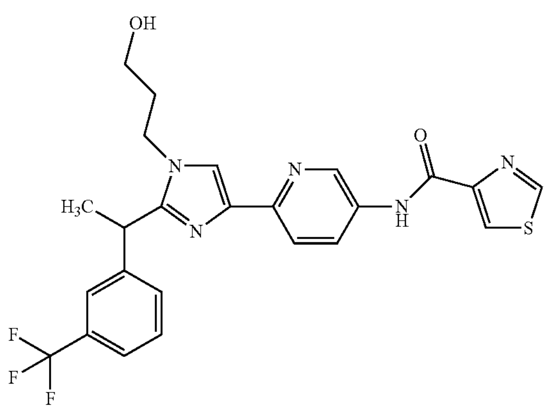 [SMILES: CC(c1cccc(C(F)(F)F)c1)c1nc(-c2ccc(NC(=O)c3cscn3)cn2)cn1CCCO] | A23 | 502.2 | 1.0 |
| 1112 | 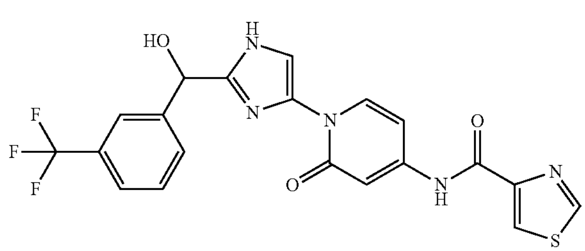 [SMILES: O=C(Nc1ccn(-c2c[nH]c(C(O)c3cccc(C(F)(F)F)c3)n2)c(=O)c1)c1cscn1] | A10 | 462.2 | 1.0 |

TABLE 1-continued

| Cmpd # | Structure | Example # for synthesis | [M + H]+ | $t_R$ (min) |
|---|---|---|---|---|
| 1113 | 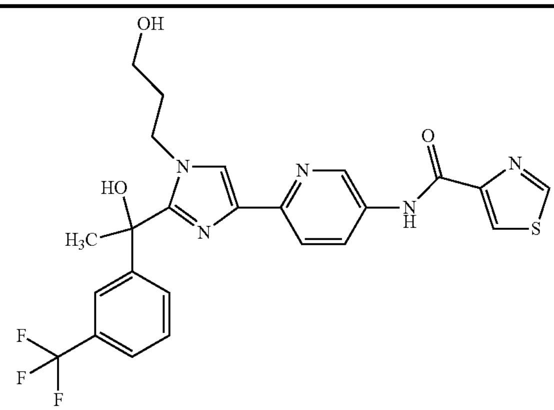 | A23 | 518.3 | 1.0 |
| 1114 | 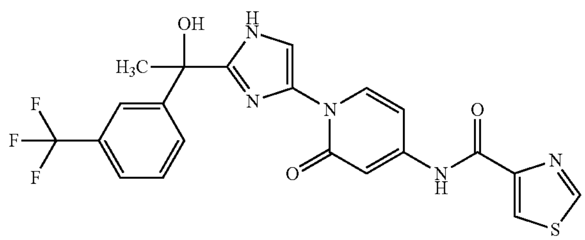 [SMILES: CC(O)(c1cccc(C(F)(F)F)c1)c1nc(-n2ccc(NC(=O)c3cscn3)cc2=O)c[nH]1] | A10 | 476.2 | 1.1 |
| 1115 | 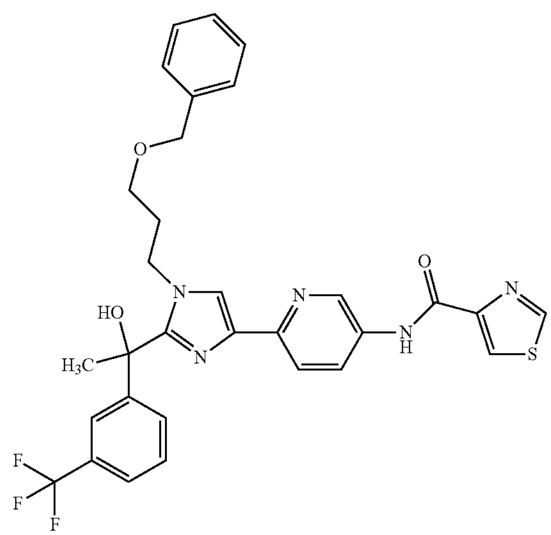 [SMILES: CC(O)(c1cccc(C(F)(F)F)c1)c1nc(-c2ccc(NC(=O)c3cscn3)cn2)cn1CCCOCc1ccccc1] | A23 | 608.4 | 1.4 |
| 1116 | 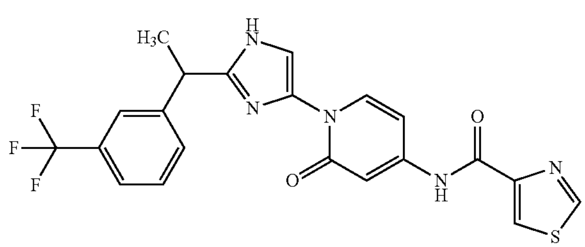 | A10 | 460 | 1.1 |
| 1117 | 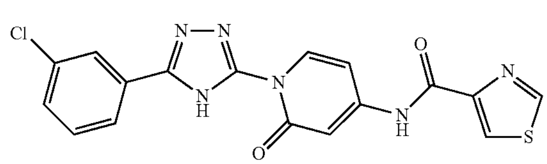 [SMILES: O=C(Nc1ccn(-c2nnc(-c3cccc(Cl)c3)[nH]2)c(=O)c1)c1cscn1] | A25 | 399.2 401.2 | 0.86 |

TABLE 1-continued

| Cmpd # | Structure | Example # for synthesis | [M + H]+ | $t_R$ (min) |
|---|---|---|---|---|
| 1118 | 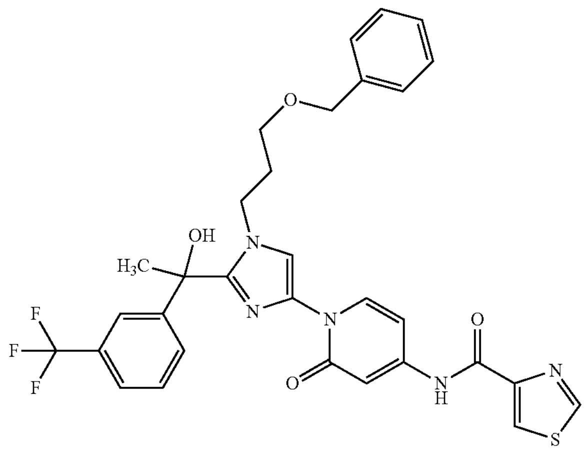 [SMILES: CC(O)(c1cccc(C(F)(F)F)c1)c1nc(-n2ccc(NC(=O)c3cscn3)cc2=O)cn1CCCOCc1ccccc1] | A22 | 624.4 | 1.6 |
| 1119 | 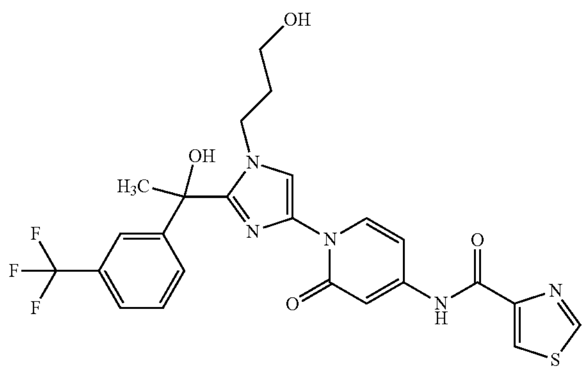 [SMILES: CC(O)(c1cccc(C(F)(F)F)c1)c1nc(-n2ccc(NC(=O)c3cscn3)cc2=O)cn1CCCO] | A22 | 534.3 | 1.1 |
| 1120 | 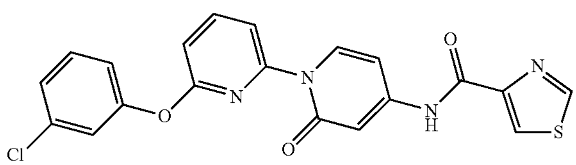 [SMILES: O=C(Nc1ccn(-c2cccc(Oc3cccc(Cl)c3)n2)c(=O)c1)c1cscn1] | A12 | 425.2 427.1 | 1.3 |
| 1121 | 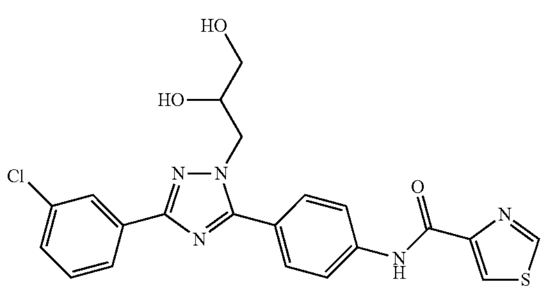 [SMILES: O=C(Nc1ccc(-c2nc(-c3cccc(Cl)c3)nn2CC(O)CO)cc1)c1cscn1] | A9 | 456.3 458.4 | 1.16 |
| 1122 | 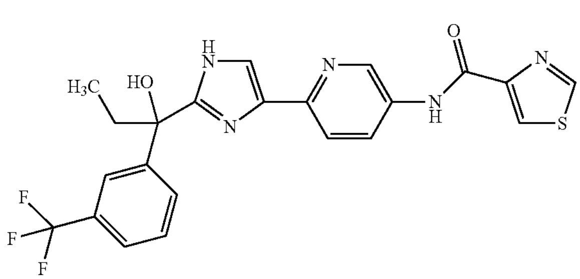 [SMILES: CCC(O)(c1cccc(C(F)(F)F)c1)c1nc(-c2ccc(NC(=O)c3cscn3)cn2)c[nH]1] | A11 | 474.3 | 1.0 |

TABLE 1-continued

| Cmpd # | Structure | Example # for synthesis | [M + H]+ | t_R (min) |
|---|---|---|---|---|
| 1123 | 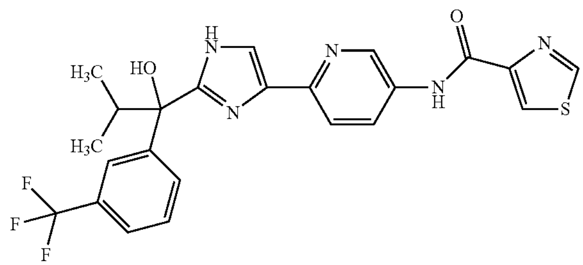 [SMILES: CC(C)C(O)(c1cccc(C(F)(F)F)c1)c1nc(-c2ccc(NC(=O)c3cscn3)cn2)c[nH]1] | A11 | 488.3 | 1.1 |
| 1124 | 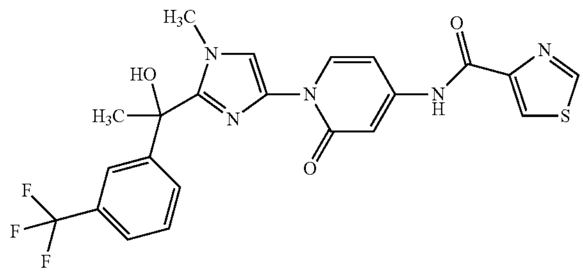 [SMILES: Cn1cc(-n2ccc(NC(=O)c3cscn3)cc2=O)nc1C(C)(O)c1cccc(C(F)(F)F)c1] | A10 | 490.4 | 1.2 |
| 1125 | 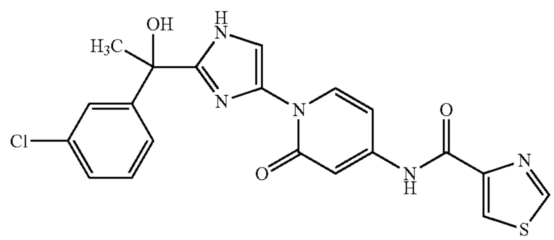 [SMILES: CC(O)(c1cccc(Cl)c1)c1nc(-n2ccc(NC(=O)c3cscn3)cc2=O)c[nH]1] | A10 | 441.9 444.0 | 1.0 |
| 1126 | 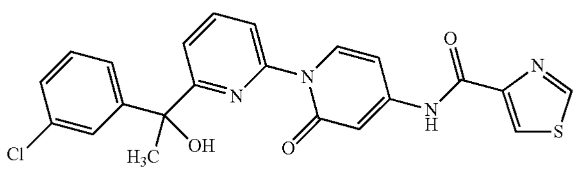 [SMILES: CC(O)(c1cccc(Cl)c1)c1cccc(-n2ccc(NC(=O)c3cscn3)cc2=O)n1] | A13 | 453.0 455.0 | 1.2 |
| 1127 | 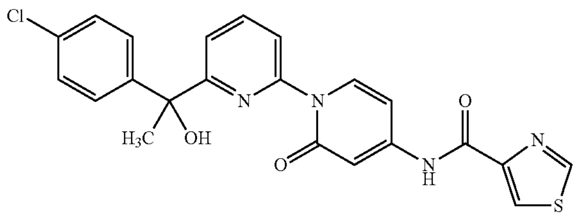 [SMILES: CC(O)(c1ccc(Cl)cc1)c1cccc(-n2ccc(NC(=O)c3cscn3)cc2=O)n1] | A13 | 453.0 455.0 | 1.2 |
| 1128 | 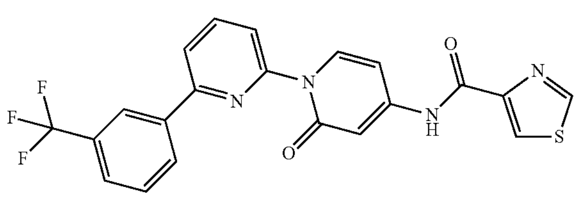 [SMILES: O=C(Nc1ccn(-c2cccc(-c3cccc(C(F)(F)F)c3)n2)c(=O)c1)c1cscn1] | A12 | 443 | 1.4 |
| 1129 | 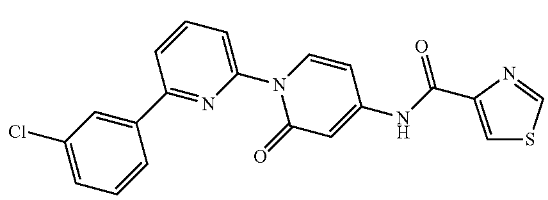 [SMILES: O=C(Nc1ccn(-c2cccc(-c3cccc(Cl)c3)n2)c(=O)c1)c1cscn1] | A12 | 409.0 411.0 | 1.3 |

TABLE 1-continued
| Cmpd # | Structure | Example # for synthesis | [M + H]+ | $t_R$ (min) |
|---|---|---|---|---|
| 1130 | 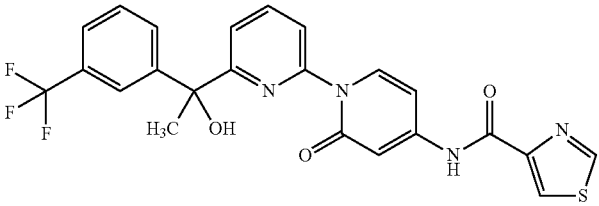 [SMILES: CC(O)(c1cccc(C(F)(F)F)c1)c1cccc(-n2ccc(NC(=O)c3cscn3)cc2=O)n1] | A13 | 487 | 1.3 |
| 1131 | 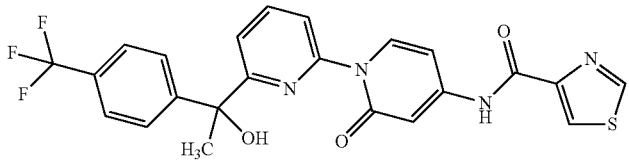 [SMILES: CC(O)(c1ccc(C(F)(F)F)cc1)c1cccc(-n2ccc(NC(=O)c3cscn3)cc2=O)n1] | A13 | 487 | 1.3 |
| 1132 | 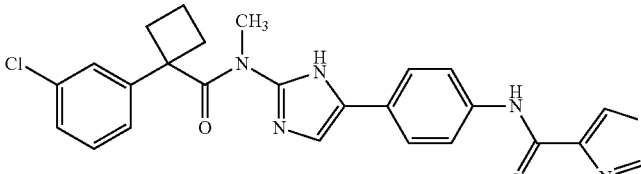 | A27 | 506.2 | 1.5 |
| 1133 | 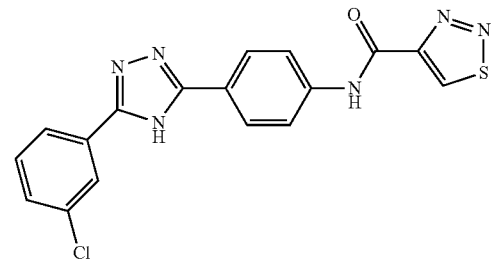 [SMILES: O=C(Nc1ccc(-c2nnc(-c3cccc(Cl)c3)[nH]2)cc1)c1csnn1] | A30 | 382.6 384.7 | 1.29 |
| 1134 | 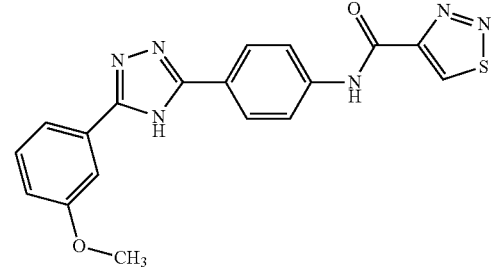 [SMILES: COc1cccc(-c2nnc(-c3ccc(NC(=O)c4csnn4)cc3)[nH]2)c1] | A30 | 379 | 1.1 |
| 1135 | 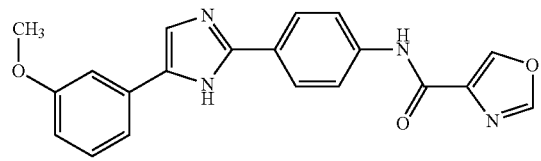 [SMILES: COc1cccc(-c2cnc(-c3ccc(NC(=O)c4cocn4)cc3)[nH]2)c1] | A32 | 361.2 | 1.5 |

TABLE 1-continued

| Cmpd # | Structure | Example # for synthesis | [M + H]+ | $t_R$ (min) |
|---|---|---|---|---|
| 1136 | 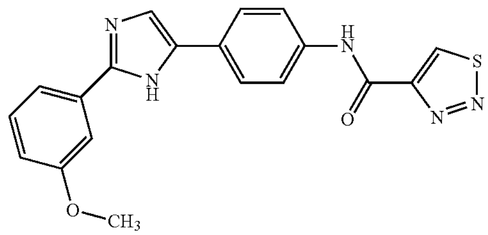 [SMILES: COc1cccc(-c2ncc(-c3ccc(NC(=O)c4csnn4)cc3)[nH]2)c1] | A31 | 378 | 1.0 |
| 1137 | 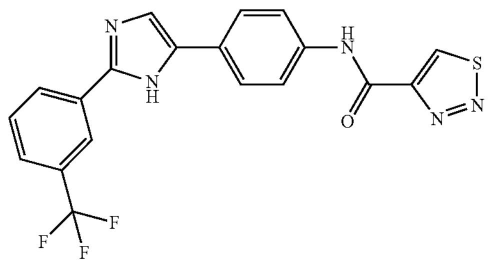 [SMILES: O=C(Nc1ccc(-c2cnc(-c3cccc(C(F)(F)F)c3)[nH]2)cc1)c1csnn1] | A31 | 416 | 1.35 |
| 1138 | 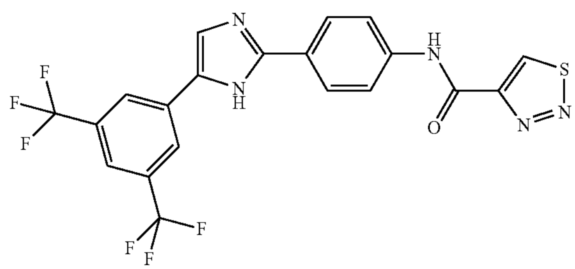 [SMILES: O=C(Nc1ccc(-c2ncc(-c3cc(C(F)(F)F)cc(C(F)(F)F)c3)[nH]2)cc1)c1csnn1] | A32 | 484.1 | 2.13 |
| 1139 | 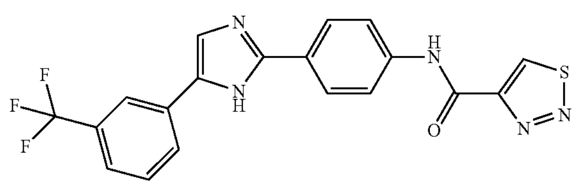 [SMILES: O=C(Nc1ccc(-c2ncc(-c3cccc(C(F)(F)F)c3)[nH]2)cc1)c1csnn1] | A32 | 416.1 | 1.9 |
| 1140 | 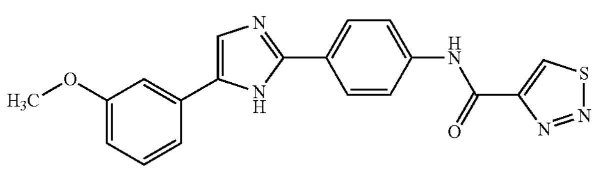 [SMILES: COc1cccc(-c2cnc(-c3ccc(NC(=O)c4csnn4)cc3)[nH]2)c1] | A32 | 378.1 | 1.58 |
| 1141 | 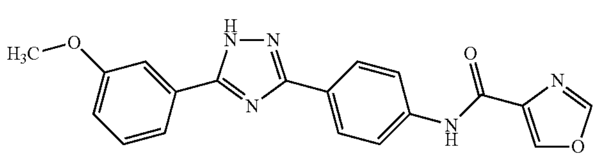 [SMILES: COc1cccc(-c2nc(-c3ccc(NC(=O)c4cocn4)cc3)n[nH]2)c1] | A33 | 362.2 | 1.69 |
| 1142 | 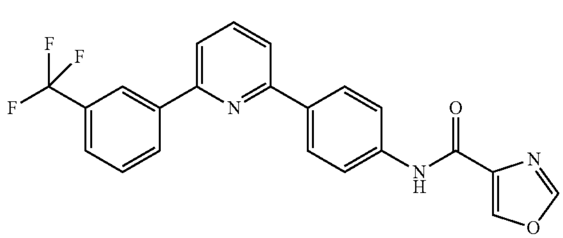 [SMILES: O=C(Nc1ccc(-c2cccc(-c3cccc(C(F)(F)F)c3)n2)cc1)c1cocn1] | A33 | 410.1 | 1.69 |

TABLE 1-continued

| Cmpd # | Structure | Example # for synthesis | [M + H]+ | $t_R$ (min) |
|---|---|---|---|---|
| 1143 | 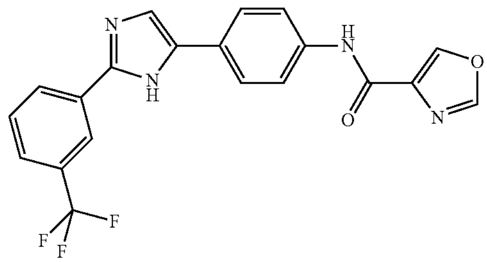 [SMILES: O=C(Nc1ccc(-c2cnc(-c3cccc(C(F)(F)F)c3)[nH]2)cc1)c1cocn1] | A31 | 399.1 | 1.27 |
| 1144 | 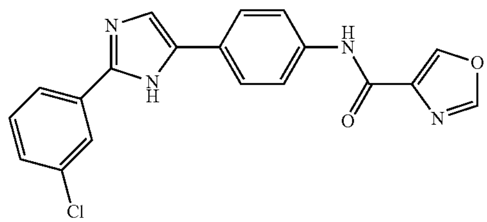 [SMILES: O=C(Nc1ccc(-c2cnc(-c3cccc(Cl)c3)[nH]2)cc1)c1cocn1] | A31 | 365 | 1.16 |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of Formula (I) or racemate, enantiomer, diastereomer or tautomer thereof:

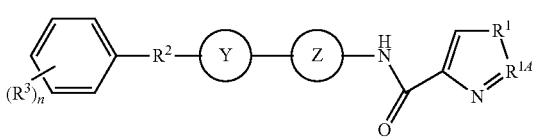

wherein
$R^1$ is S or O;
$R^{14}$ is CH or N;
Ring Z is selected from the group consisting of phenyl, pyridine and pyridinone, wherein said phenyl, pyridine and pyridinone are each optionally mono-, di- or tri-substituted with $(C_{1-6})$alkyl or —O—$(C_{1-6})$alkyl;
Ring Y is selected from the group consisting of imidazole, triazole and pyridine, wherein said imidazole, triazole and pyridine are each optionally mono-, di- or tri-substituted with halo, —CN, OH, —O—$(C_{1-6})$alkyl, —C(=O)NH$_2$, $(C_{1-6})$haloalkyl, $(C_{2-6})$alkenyl, $(C_{2-6})$alkynyl or $(C_{1-6})$alkyl optionally mono- or di-substituted with OH, —C(=O)NH$_2$, —C(=O)OH, $Y^1$, —O—$(C_{1-6})$alkyl-$Y^1$ or —N(H)—$(C_{1-6})$alkyl)-$Y^1$;
$Y^1$ is aryl, heterocycle or heteroaryl, wherein said aryl, heterocycle or heteroaryl are each optionally mono-, di- or tri-substituted with halo, —CN, OH, —O—$(C_{1-6})$alkyl, $(C_{1-6})$haloalkyl or $(C_{1-6})$alkyl;
$R^2$ is absent, $(C_{1-6})$alkyl, $(C_{3-7})$cycloalkyl, —O, *—N$(R^{2A})$—C(=O)— §, *—N$(R^{2A})$—C(=O)—$(C_{3-7})$cycloalkyl-§, *—N$(R^{2A})$—C(=O)—$(C_{1-6})$alkyl-§ (wherein, when necessary, the site of attachment to the Y ring is indicated with an * and the site of attachment to the phenyl ring is indicated with a §);
wherein each said alkyl is optionally mono-, di- or tri-substituted with substituents independently selected from the group consisting of OH, —O—$(C_{1-6})$alkyl, —O-aryl and —O—$(C_{1-6})$alkyl-aryl;
$R^{2A}$ is H or $(C_{1-6})$alkyl;
$R^3$ is halo, $(C_{1-6})$haloalkyl, —CN, OH, —O—$(C_{1-6})$alkyl or $(C_{1-6})$alkyl,
wherein each said alkyl is optionally mono- or di-substituted with OH, C(=O)OH, aryl, heterocycle or heteroaryl;
n is 0, 1, 2 or 3;
or a salt thereof.

2. The compound according to claim 1, wherein Ring Z is selected from the group consisting of phenyl, pyridine and pyridinone;

or a pharmaceutically acceptable salt thereof.

3. The compound according to claim 1, having the formula:

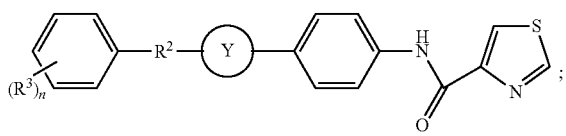

or a pharmaceutically acceptable salt thereof.

4. The compound according to claim 1, having the formula:

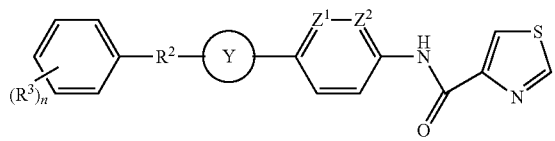

wherein one of $Z^1$ and $Z^2$ is CH and the other of $Z^1$ and $Z^2$ is N;
or a pharmaceutically acceptable salt thereof.

5. The compound according to claim 1, having the formula:

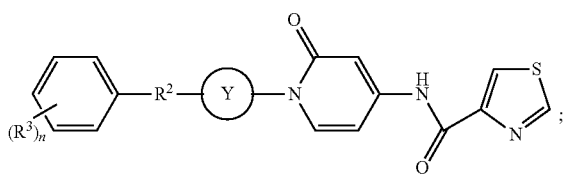

or a pharmaceutically acceptable salt thereof.

6. The compound according to claim 1, wherein Ring Y is selected from the group consisting of imidazole, triazole and pyridine;
or a pharmaceutically acceptable salt thereof.

7. The compound according to claim 6, wherein Ring Y is imidazole;
or a pharmaceutically acceptable salt thereof.

8. The compound according to claim 6, wherein Ring Y is triazole;
or a pharmaceutically acceptable salt thereof.

9. The compound according to claim 6, wherein Ring Y is pyridine;
or a pharmaceutically acceptable salt thereof.

10. The compound according to claim 1, wherein $R^2$ is absent or $(C_{1-6})$alkyl, optionally mono-, di- or tri-substituted with substituents independently selected from the group consisting of OH, —O—$(C_{1-6})$alkyl, —O-aryl and —O—$(C_{1-6})$alkyl-aryl;
or a pharmaceutically acceptable salt thereof.

11. The compound according to claim 10, wherein $R^2$ is absent;
or a pharmaceutically acceptable salt thereof.

12. The compound according to claim 1, wherein $R^3$ is halo, $(C_{1-6})$haloalkyl, —CN or $(C_{1-6})$alkyl;
or a pharmaceutically acceptable salt thereof.

13. The compound according to claim 12, wherein $R^3$ is halo or $(C_{1-6})$haloalkyl;
or a pharmaceutically acceptable salt thereof.

14. The compound according to claim 1, wherein n is 0, 1 or 2;
or a pharmaceutically acceptable salt thereof.

15. The compound according to claim 14, wherein n is 1 or 2;
or a pharmaceutically acceptable salt thereof.

16. A method for the treatment of CMV disease and/or invention comprising administering a therapeutically effective amount of a compound according to claim 1 to a patient in need thereof.

17. A pharmaceutical composition comprising a compound according to claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,284,310 B2 | Page 1 of 1 |
| APPLICATION NO. | : 14/440086 | |
| DATED | : March 15, 2016 | |
| INVENTOR(S) | : Lee Fader et al. | |

It is certified that error appears in the above-identified patent and that said Letters Patent is hereby corrected as shown below:

In the Claims

In claim 16, column 118, lines 32-33, change the text reading

"16. A method for the treatment of CMV disease and/or invention comprising"

to

-- 16. A method for the treatment of CMV disease and/or infection comprising --

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggtgcag gtgccctg                                                 18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgtcgacga acgacgtacg                                               20

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-ZEN
<220> FEATURE:
<223> OTHER INFORMATION: 3'-IABkFQ
```

```
<400> SEQUENCE: 3
tagacccgca tacaaa                                                    16

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acccactccc tcttagccaa tatt                                           24

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtagggctag gcccaccg                                                  18

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-JOE
<220> FEATURE:
<223> OTHER INFORMATION: 3'-IABkFQ

<400> SEQUENCE: 6
ctagtctttg ccgcctgcga agca                                           24
```